US012146169B2

(12) United States Patent
Bosch Tubert et al.

(10) Patent No.: US 12,146,169 B2
(45) Date of Patent: Nov. 19, 2024

(54) ADENOASSOCIATED VIRUS VECTORS FOR THE TREATMENT OF MUCOPOLYSACCHARIDOSES TYPE IV A

(71) Applicants: ESTEVE PHARMACEUTICALS, S.A., Barcelona (ES); UNIVERSITAT AUTÓNOMA DE BARCELONA, Cerdanyola del Valles (ES)

(72) Inventors: Maria Fátima Bosch Tubert, Cerdanyola del Valles (ES); Victor Sanchez Clares, Sabadell (ES); Albert Ribera Sanchez, Santa Eulàlia de Ronçana (ES); Virginia A. Haurigot, Barcelona (ES)

(73) Assignees: ESTEVE PHARMACEUTICALS, S.A., Barcelona (ES); UNIVERSITAT AUTÓNOMA DE BARCELONA, Cerdanyola del Vallès (ES)

( * ) Notice: Subject to any disclaimer, the term of this patent is extended or adjusted under 35 U.S.C. 154(b) by 921 days.

(21) Appl. No.: 17/059,723

(22) PCT Filed: May 27, 2019

(86) PCT No.: PCT/EP2019/063582

§ 371 (c)(1),
(2) Date: Nov. 30, 2020

(87) PCT Pub. No.: WO2019/228950

PCT Pub. Date: Dec. 5, 2019

(65) Prior Publication Data

US 2021/0214695 A1 Jul. 15, 2021

(30) Foreign Application Priority Data

May 30, 2018 (EP) .................................... 18382373

(51) Int. Cl.

| | |
|---|---|
| ***C07H 21/04*** | (2006.01) |
| ***A61K 9/00*** | (2006.01) |
| ***A61P 43/00*** | (2006.01) |
| ***C12N 9/16*** | (2006.01) |
| ***C12N 15/86*** | (2006.01) |

(52) U.S. Cl.

CPC ............. *C12N 9/16* (2013.01); *A61K 9/0019* (2013.01); *A61P 43/00* (2018.01); *C12N 15/86* (2013.01); *C12Y 301/06004* (2013.01); *C12N 2750/14143* (2013.01); *C12N 2750/14152* (2013.01)

(58) Field of Classification Search

None

See application file for complete search history.

(56) References Cited

U.S. PATENT DOCUMENTS

2010/0008979 A1 1/2010 Tomatsu

FOREIGN PATENT DOCUMENTS

WO WO-2004014946 A1 * 2/2004 ............ C07H 21/00
WO WO2018060097 4/2018

OTHER PUBLICATIONS

AF111346 mRNA, Montano et al. (Year: 2000).*
Kosuga (Cell Transplantation, 2000 vol. 9, pp. 675-680). (Year: 2000).*
Blakrishnan (Current Gene Therapy, 2014, vol. 14, pp. 1-15). (Year: 2014).*
Alexopoulou, A. et al., "The CMV early enhancer/chicken ß actin (CAG) promoter can be used to drive transgene expression during the differentation of murine embryonic stem cells into vascular progenitors", BMC Cell Biology, 2008; 9(2), pp. 1-11.
Alméciga Diaz, Carlos, J., et al., "Adeno-associated virus gene transfer in Morquio A disease—effect of promoters and sulfatase-modifying factor 1", FEBS Journal, 277, 2010, pp. 3608-3619.
Alméciga Diaz, Carolos Javier, et al., "Colombian contribution to knowledge of Morquio A Disease", Medicina (Bogota), vol. 34, No. 3 (98), Sep. 2012, pp. 221-241—English Translation.
Alméciga Diaz, Carolos Javier, et al., "Contribución Colombiana al conocimento de la enfermedad de Morquio A", Medicina (Bogota), vol. 34, No. 3 (98), Sep. 2012, pp. 221-241.
Almeciga, Carlos, et al., "New viral vectors for Morquio syndrome type A gene therapy", Abstracts, 2012, pp. S19.
Altschul, Stephen, A., et al., "Gapped BLAST and PSI-BLAST: a new generation of protein database search programs", Nucleic Acids Research, vol. 25, No. 17, 1997, pp. 3389-3402.
Altschul, Stephen, F., et al., "Basic local alignment search tool", J. Mol. Biol., 215, 1990, pp. 403-410.
Ayuso, E., et al., "High AAV vector purity results in serotype- and tissue-independent enhancement of transduction efficiency", Gene Therapy, 17, 2010, pp. 503-510.
Chinen, Yasutsugu, et al., "Long-term therapeutic efficacy of allogenic bone marrow transplantation in a patient with mucopolysaccharidosis IVA", Molecular Genetics and Metabolism Reports, 1:31-41, 2014.
International Search Report for PCT/EP2019/063582 dated Jun. 17, 2019.
Matsushita, T., et al., "Adeno-associated virus vectors can be efficiently produced without helper virus", Gene Therapy, 5, 1998, pp. 938-945.
Ruzo, Albert, et al., "Liver production of sulfamidase reverses peripheral and ameliorates CNS pathology in mucopolysaccharidosis IIIA mice", www.moleculartherapy.org, vol. 20, No. 2, Feb. 2012, pp. 254-266.
Salazar, Diego, A., et al., "Systems biology study of mucopolysaccharidosis using a human metabolic reconstruction network", Molecular Genetics and Metabolism, 2015, pp. 1-11.
Sanford, Mark, et al., "Elosulfase alfa: first global approval", Drugs, 74, 2014, pp. 713-718.

(Continued)

*Primary Examiner* — Celine X Qian
(74) *Attorney, Agent, or Firm* — HUESCHEN AND SAGE

(57) ABSTRACT

The present invention provides new polynucleotide sequences, adeno-associated virus-derived vectors and pharmaceutical compositions containing the same for the treatment of lysosomal storage disorders and specially, for the treatment of mucopolysaccharidosis type IVA or Morquio A syndrome.

12 Claims, 14 Drawing Sheets

Specification includes a Sequence Listing.

(56) References Cited

OTHER PUBLICATIONS

Toietta, Gabriele, et al., "Various cells retrovirally transduced with N-acetylgalactosoamine-6-sulfate sulfatase correct Morquio skin fibroblasts In Vitro", Human Gene Therapy, 12, Nov. 1, 2001, pp. 2007-2016.
Tomatsu, Shunji, et al., "Enhancement of drug delivery: enzyme-replacement therapy for Murine Morquio A Syndrome", www.moleculartherapy.org, vol. 18, No. 6, Jun. 2010, pp. 1094-1102.
Tomatsu, Shunji, et al., "Enzyme replacement therapy for treating mucopolysaccharidosis type IVA (Morquio A syndrome) : effect and limitations", Expert Opinion on Orphan Drugs, 3:11, 2015, pp. 1279-1290.
Tomatsu, Shunji, et al., "Enzyme replacement therapy in a murine model of Morquio A syndrome", Human Molecular Genetics, vol. 17, No. 6, 2008, pp. 815-824.
Van Diggelen, O.P., et al., "A fluorimetric assay for the diagnosis of Morquio disease type A (MPS IV A)", Clinica Chimica Acta, 187, 1990, pp. 131-140.
Wang, Jianmin, et al., "Allogeneic hematopoietic stem cell transplantation in thirty-four pediatric cases of mucopolysaccharidosis—a ten-year report from the China Children Transplant Group", Biol Blood Marrow Transplant, 22, 2016, pp. 2100-2108.
Wright, J. Fraser, et al., "Identification of factors that contribute to recombinant AAV2 particle aggregation and methods to prevent its occurrence during vector purification and formulation", Molecular Therapy, vol. 12, No. 1, Jul. 2005, pp. 171-178.
Yabe, Hiromasa, et al., "Hematopoietic stem cell transplantation for Morquio A syndrome", Molecular Genetics and Metabolism, 117, 2016, pp. 84-94.

* cited by examiner

A

B

A

B

A

B

A

B

SEQUENCE LISTING

```
<160> NUMBER OF SEQ ID NOS: 22

<210> SEQ ID NO 1
<211> LENGTH: 1577
<212> TYPE: DNA
<213> ORGANISM: Homo sapiens

<400> SEQUENCE: 1

tgccaccatg gcggcggttg tcgcggcgac gaggtggtgg cagctgttgc tggtgctcag     60
```

```
cgccgcgggg atgggggcct cgggcgcccc gcagcccccc aacatcctgc tcctgctcat    120

ggacgacatg ggatggggtg acctcggggt gtatggagag ccctccagag agaccccgaa    180

tttggaccgg atggctgcag aagggctgct tttcccaaac ttctattctg ccaaccctct    240

gtgctcgcca tcgagggcgg cactgctcac aggacggcta cccatccgca atggcttcta    300

caccaccaac gcccatgcca gaaacgccta cacaccgcag gagattgtgg gcggcatccc    360

agactcggag cagctcctgc cggagcttct gaagaaggcc ggctacgtca gcaagattgt    420

cggcaagtgg catctgggtc acaggcccca gttccacccc ctgaagcacg gatttgatga    480

gtggtttgga tcccccaact gccactttgg accttatgac aacaaggcca ggcccaacat    540

ccctgtgtac agggactggg agatggttgg cagatattat gaagaatttc ctattaatct    600

gaagacgggg gaagccaacc tcacccagat ctacctgcag gaagccctgg acttcattaa    660

gagacaggca cggcaccacc ccttttttcct ctactgggct gtcgacgcca cgcacgcacc    720

cgtctatgcc tccaaaccct tcttgggcac cagtcagcga gggcggtatg gagacgccgt    780

ccgggagatt gatgacagca ttgggaagat actggagctc ctccaagacc tgcacgtcgc    840

ggacaacacc ttcgtcttct tcacgtcgga caacggcgct gccctcattt ccgcccccga    900

acaaggtggc agcaacggcc cctttctgtg tgggaagcag accacgtttg aaggagggat    960

gagggagcct gccctcgcat ggtggccagg gcacgtcact gcaggccagg tgagccacca   1020

gctgggcagc atcatggacc tcttcaccac cagcctggcc cttgcgggcc tgacgccgcc   1080

cagcgacagg gccattgatg gcctcaacct cctccccacc ctcctgcagg gccggctgat   1140

ggacaggcct atcttctatt accgtggcga cacgctgatg gcggccaccc tcgggcagca   1200

caaggctcac ttctggacct ggaccaactc ctgggagaac ttcagacagg gcattgattt   1260

ctgccctggg cagaacgttt caggggtcac aactcacaat ctggaagacc acacgaagct   1320

gcccctgatc ttccacctgg gacgggaccc aggggagagg ttccccctca gctttgccag   1380

cgccgagtac caggaggccc tcagcaggat cacctcggtc gtccagcagc accaggaggc   1440

cttggtcccc gcgcagcccc agctcaacgt gtgcaactgg gcggtcatga actgggcacc   1500

tccgggctgt gaaaagttag ggaagtgtct gacacctcca gaatccattc ccaagaagtg   1560

cctctggtcc cactagg                                                  1577


<210> SEQ ID NO 2
<211> LENGTH: 7804
<212> TYPE: DNA
<213> ORGANISM: Artificial Sequence
<220> FEATURE:
<223> OTHER INFORMATION: pAAV-CAG-hGALNS

<400> SEQUENCE: 2

gctgcgcgct cgctcgctca ctgaggccgc ccgggcaaag cccgggcgtc gggcgacctt     60

tggtcgcccg gcctcagtga gcgagcgagc gcgcagagag ggagtggcca actccatcac    120

taggggttcc ttgtagttaa tgattaaccc gccatgctac ttatctactc gacattgatt    180

attgactagt tattaatagt aatcaattac ggggtcatta gttcatagcc catatatgga    240

gttccgcgtt acataactta cggtaaatgg cccgcctggc tgaccgccca acgacccccg    300

cccattgacg tcaataatga cgtatgttcc catagtaacg ccaataggga ctttccattg    360

acgtcaatgg gtggagtatt tacggtaaac tgcccacttg gcagtacatc aagtgtatca    420

tatgccaagt acgcccccta ttgacgtcaa tgacggtaaa tggcccgcct ggcattatgc    480
```

-continued

```
ccagtacatg accttatggg actttcctac ttggcagtac atctacgtat tagtcatcgc    540
tattaccatg gtcgaggtga gccccacgtt ctgcttcact ctccccatct cccccccctc    600
cccaccccca attttgtatt tatttatttt ttaattattt tgtgcagcga tgggggcggg    660
gggggggggg gggcgcgcgc caggcggggc ggggcggggc gaggggcggg gcggggcgag    720
gcggagaggt gcggcggcag ccaatcagag cggcgcgctc cgaaagtttc cttttatggc    780
gaggcggcgg cggcggcggc cctataaaaa gcgaagcgcg cggcgggcgg gagtcgctgc    840
gttgccttcg ccccgtgccc cgctccgccg ccgcctcgcg ccgcccgccc cggctctgac    900
tgaccgcgtt actcccacag gtgagcgggc gggacggccc ttctcctccg ggctgtaatt    960
agcgcttggt ttaatgacgg cttgtttctt ttctgtggct gcgtgaaagc cttgaggggc   1020
tccgggaggg ccctttgtgc ggggggagcg gctcgggggg tgcgtgcgtg tgtgtgtgcg   1080
tggggagcgc cgcgtgcggc tccgcgctgc ccggcggctg tgagcgctgc gggcgcggcg   1140
cggggctttg tgcgctccgc agtgtgcgcg aggggagcgc ggccgggggc ggtgccccgc   1200
ggtgcggggg gggctgcgag gggaacaaag gctgcgtgcg gggtgtgtgc gtgggggggt   1260
gagcaggggg tgtgggcgcg tcggtcgggc tgcaaccccc cctgcacccc cctccccgag   1320
ttgctgagca cggcccggct tcgggtgcgg ggctccgtac ggggcgtggc gcggggctcg   1380
ccgtgccggg cggggggtgg cggcaggtgg gggtgccggg cggggcgggg ccgcctcggg   1440
ccggggaggg ctcgggggag gggcgcggcg gcccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggcg gcggttgtcg cggcgacgag gtggtggcag ctgttgctgg tgctcagcgc   1980
cgcggggatg gggggcctcgg gcgccccgca gcccccaac atcctgctcc tgctcatgga   2040
cgacatggga tggggtgacc tcggggtgta tggagagccc tccagagaga ccccgaattt   2100
ggaccggatg gctgcagaag ggctgctttt cccaaacttc tattctgcca accctctgtg   2160
ctcgccatcg agggcggcac tgctcacagg acggctaccc atccgcaatg gcttctacac   2220
caccaacgcc catgccagaa acgcctacac accgcaggag attgtgggcg gcatcccaga   2280
ctcggagcag ctcctgccgg agcttctgaa gaaggccggc tacgtcagca agattgtcgg   2340
caagtggcat ctgggtcaca ggccccagtt ccacccctg aagcacggat ttgatgagtg   2400
gtttggatcc cccaactgcc actttggacc ttatgacaac aaggccaggc ccaacatccc   2460
tgtgtacagg gactgggaga tggttggcag atattatgaa gaatttccta ttaatctgaa   2520
gacgggggaa gccaacctca cccagatcta cctgcaggaa gccctggact tcattaagag   2580
acaggcacgg caccacccct tttcctcta ctgggctgtc gacgccacgc acgcacccgt   2640
ctatgcctcc aaacccttct tgggcaccag tcagcgaggg cggtatggag acgccgtccg   2700
ggagattgat gacagcattg ggaagatact ggagctcctc caagacctgc acgtcgcgga   2760
caacaccttc gtcttcttca cgtcggacaa cggcgctgcc ctcatttccg cccccgaaca   2820
aggtggcagc aacggcccct ttctgtgtgg gaagcagacc acgtttgaag gagggatgag   2880
```

-continued

```
ggagcctgcc ctcgcatggt ggccagggca cgtcactgca ggccaggtga gccaccagct   2940
gggcagcatc atggacctct tcaccaccag cctggccctt gcgggcctga cgccgcccag   3000
cgacagggcc attgatggcc tcaacctcct ccccaccctc ctgcagggcc ggctgatgga   3060
caggcctatc ttctattacc gtggcgacac gctgatggcg gccaccctcg ggcagcacaa   3120
ggctcacttc tggacctgga ccaactcctg ggagaacttc agacagggca ttgatttctg   3180
ccctgggcag aacgtttcag ggtcacaaac tcacaatctg gaagaccaca cgaagctgcc   3240
cctgatcttc cacctgggac gggacccagg ggagaggttc cccctcagct ttgccagcgc   3300
cgagtaccag gaggccctca gcaggatcac ctcggtcgtc cagcagcacc aggaggcctt   3360
ggtccccgcg cagccccagc tcaacgtgtg caactgggcg gtcatgaact gggcacctcc   3420
gggctgtgaa aagttaggga agtgtctgac acctccagaa tccattccca agaagtgcct   3480
ctggtcccac taggaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gatttttttt atattttgtt ttgtgttatt tttttcttta acatccctaa   3960
aattttcctt acatgtttta ctagccagat ttttcctcct ctcctgacta ctcccagtca   4020
tagctgtccc tcttctctta tggagatccc tcgacctgca gcccaagctg tagataagta   4080
gcatggcggg ttaatcatta actacaagga acccctagtg atggagttgg ccactccctc   4140
tctgcgcgct cgctcgctca ctgaggccgc ccgggctttg cccgggcggc ctcagtgagc   4200
gagcgagcgc gcagctgcat taatgaatcg gccaacgcgc ggggagaggc ggtttgcgta   4260
ttgggcgctc ttccgcttcc tcgctcactg actcgctgcg ctcggtcgtt cggctgcggc   4320
gagcggtatc agctcactca aaggcggtaa tacggttatc cacagaatca ggggataacg   4380
caggaaagaa catgtgagca aaaggccagc aaaaggccag gaaccgtaaa aaggccgcgt   4440
tgctggcgtt tttccatagg ctccgccccc ctgacgagca tcacaaaaat cgacgctcaa   4500
gtcagaggtg gcgaaacccg acaggactat aaagatacca ggcgtttccc cctggaagct   4560
ccctcgtgcg ctctcctgtt ccgaccctgc cgcttaccgg atacctgtcc gcctttctcc   4620
cttcgggaag cgtggcgctt tctcatagct cacgctgtag gtatctcagt tcggtgtagg   4680
tcgttcgctc caagctgggc tgtgtgcacg aaccccccgt tcagcccgac cgctgcgcct   4740
tatccggtaa ctatcgtctt gagtccaacc cggtaagaca cgacttatcg ccactggcag   4800
cagccactgg taacaggatt agcagagcga ggtatgtagg cggtgctaca gagttcttga   4860
agtggtggcc taactacggc tacactagaa gaacagtatt tggtatctgc gctctgctga   4920
agccagttac cttcggaaaa agagttggta gctcttgatc cggcaaacaa accaccgctg   4980
gtagcggtgg tttttttgtt tgcaagcagc agattacgcg cagaaaaaaa ggatctcaag   5040
aagatccttt gatcttttct acggggtctg acgctcagtg gaacgaaaac tcacgttaag   5100
ggattttggt catgagatta tcaaaaagga tcttcaccta gatcctttta aattaaaaat   5160
gaagttttaa atcaatctaa agtatatatg agtaaacttg gtctgacagt taccaatgct   5220
```

-continued

```
taatcagtga ggcacctatc tcagcgatct gtctatttcg ttcatccata gttgcctgac   5280
tccccgtcgt gtagataact acgatacggg agggcttacc atctggcccc agtgctgcaa   5340
tgataccgcg agacccacgc tcaccggctc cagatttatc agcaataaac cagccagccg   5400
gaagggccga gcgcagaagt ggtcctgcaa ctttatccgc ctccatccag tctattaatt   5460
gttgccggga agctagagta agtagttcgc cagttaatag tttgcgcaac gttgttgcca   5520
ttgctacagg catcgtggtg tcacgctcgt cgtttggtat ggcttcattc agctccggtt   5580
cccaacgatc aaggcgagtt acatgatccc ccatgttgtg caaaaaagcg gttagctcct   5640
tcggtcctcc gatcgttgtc agaagtaagt tggccgcagt gttatcactc atggttatgg   5700
cagcactgca taattctctt actgtcatgc catccgtaag atgcttttct gtgactggtg   5760
agtactcaac caagtcattc tgagaatagt gtatgcggcg accgagttgc tcttgcccgg   5820
cgtcaatacg ggataatacc gcgccacata gcagaacttt aaaagtgctc atcattggaa   5880
aacgttcttc ggggcgaaaa ctctcaagga tcttaccgct gttgagatcc agttcgatgt   5940
aacccactcg tgcacccaac tgatcttcag catcttttac tttcaccagc gtttctgggt   6000
gagcaaaaac aggaaggcaa aatgccgcaa aaaagggaat aagggcgaca cggaaatgtt   6060
gaatactcat actcttcctt tttcaatatt attgaagcat ttatcagggt tattgtctca   6120
tgagcggata catatttgaa tgtatttaga aaaataaaca aataggggtt ccgcgcacat   6180
ttccccgaaa agtgccacct gacgtctaag aaaccattat tatcatgaca ttaacctata   6240
aaaataggcg tatcacgagg ccctttcgtc tcgcgcgttt cggtgatgac ggtgaaaacc   6300
tctgacacat gcagctcccg gagacggtca cagcttgtct gtaagcggat gccgggagca   6360
gacaagcccg tcagggcgcg tcagcgggtg ttggcgggtg tcggggctgg cttaactatg   6420
cggcatcaga gcagattgta ctgagagtgc accatatgcg gtgtgaaata ccgcacagat   6480
gcgtaaggag aaaataccgc atcaggcgat tccaacatcc aataaatcat acaggcaagg   6540
caaagaatta gcaaaattaa gcaataaagc ctcagagcat aaagctaaat cggttgtacc   6600
aaaaacatta tgaccctgta atacttttgc gggagaagcc tttatttcaa cgcaaggata   6660
aaaattttta gaaccctcat atattttaaa tgcaatgcct gagtaatgtg taggtaaaga   6720
ttcaaacggg tgagaaaggc cggagacagt caaatcacca tcaatatgat attcaaccgt   6780
tctagctgat aaattcatgc cggagagggt agctattttt gagaggtctc tacaaaggct   6840
atcaggtcat tgcctgagag tctggagcaa acaagagaat cgatgaacgg taatcgtaaa   6900
actagcatgt caatcatatg taccccggtt gataatcaga aaagccccaa aaacaggaag   6960
attgtataag caaatattta aattgtaagc gttaatattt tgttaaaatt cgcgttaaat   7020
ttttgttaaa tcagctcatt ttttaaccaa taggccgaaa tcggcaaaat cccttataaa   7080
tcaaaagaat agaccgagat agggttgagt gttgttccag tttggaacaa gagtccacta   7140
ttaaagaacg tggactccaa cgtcaaaggg cgaaaaaccg tctatcaggg cgatggccca   7200
ctacgtgaac catcacccta atcaagtttt ttggggtcga ggtgccgtaa agcactaaat   7260
cggaacccta aagggagccc ccgatttaga gcttgacggg gaaagccggc gaacgtggcg   7320
agaaaggaag ggaagaaagc gaaaggagcg ggcgctaggg cgctggcaag tgtagcggtc   7380
acgctgcgcg taaccaccac acccgccgcg cttaatgcgc cgctacaggg cgcgtactat   7440
ggttgctttg acgagcacgt ataacgtgct ttcctcgtta gaatcagagc gggagctaaa   7500
caggaggccg attaaaggga ttttagacag gaacggtacg ccagaatcct gagaagtgtt   7560
tttataatca gtgaggccac cgagtaaaag agtctgtcca tcacgcaaat taaccgttgt   7620
```

-continued cgcaatactt ctttgattag taataacatc acttgcctga gtagaagaac tcaaactatc 7680
ggccttgctg gtaatatcca gaacaatatt accgccagcc attgcaacgg aatcgccatt 7740
cgccattcag gctgcgcaac tgttgggaag ggcgatcggt gcgggcctct tcgctattac 7800
gcca 7804

<210> SEQ ID NO 3
<211> LENGTH: 1577
<212> TYPE: DNA
<213> ORGANISM: Artificial Sequence
<220> FEATURE:
<223> OTHER INFORMATION: CDS ohGALNS-version1

<400> SEQUENCE: 3
tgccaccatg gctgctgtgg tggctgccac aagatggtgg cagctgctgc tggtgctgag 60
cgccgctgga atgggagctt ctggcgctcc ccagcccccc aatattctcc tgctgctgat 120
ggacgacatg ggctggggcg atctgggagt gtacggcgag cctagcagag agacacccaa 180
cctggacaga atggccgccg agggcctgct gttccccaac ttctacagcg ccaacccccct 240 gtgcagccca tctagagccg ctctgctgac cggcagactg cccatcagaa acggcttcta 300
caccaccaac gcccacgccc ggaacgccta cacaccccag gaaatcgtgg gcggcatccc 360
cgatagcgaa cagctgctgc ctgagctgct gaagaaagcc ggctacgtgt ccaagatcgt 420
gggcaagtgg cacctgggcc acagacccca gttccaccct ctgaagcacg gcttcgacga 480
gtggttcggc agccccaatt gccacttcgg cccctacgac aacaaggcca gacccaacat 540
ccccgtgtac cgggactggg agatggtggg acggtactac gaagagttcc ccatcaacct 600
gaaaaccggc gaggccaacc tgacccagat ctacctgcag gaagccctgg acttcatcaa 660
gcggcaggcc cggcaccacc ctttctttct gtactgggcc gtggacgcca cccacgcccc 720
tgtgtatgcc agcaagcctt tcctgggcac cagccagaga ggcagatacg gcgacgccgt 780
gcgcgagatc gatgacagca tcggcaagat cctggaactg ctgcaggacc tgcacgtggc 840
cgacaacacc ttcgtgttct tcaccagcga caacggcgct gccctgatct ctgctcctga 900
gcagggcggc agcaacggcc catttctgtg tggcaagcag accaccttcg agggcggcat 960
gagagaacct gccctggctt ggtggcctgg ccatgtgaca gctggacagg tgtcccacca 1020
gctgggcagc atcatggacc tgttcaccac cagcctggcc ctggccggac tgacacctcc 1080
aagcgacaga gccatcgacg gcctgaacct gctgcctacc ctgctgcagg gacggctgat 1140
ggaccggccc atcttctact acagaggcga caccctgatg gccgccacac tgggacagca 1200
caaggcccac ttttggacct ggaccaacag ctgggagaac ttccggcagg gcatcgactt 1260
ttgccctggc cagaatgtgt ccggcgtgac cacccacaac ctggaagatc acaccaagct 1320
gcccctgatt ttccacctgg gcagagatcc cggcgagcgg ttccctctgt cttttgccag 1380
cgccgagtac caggaagctc tgagcagaat cacctccgtg gtgcagcagc accaggaagc 1440
actggtgcct gctcagcccc agctgaacgt gtgcaattgg gccgtgatga actgggcccc 1500
tcccggctgt gaaaagctgg gaaagtgcct gacccccccct gagagcatcc ccaagaaatg 1560
cctgtggtcc cactgag 1577

<210> SEQ ID NO 4
<211> LENGTH: 7804
<212> TYPE: DNA
<213> ORGANISM: Artificial Sequence
<220> FEATURE:

-continued

<223> OTHER INFORMATION: pAAV-CAG-ohGALNSversion1

<400> SEQUENCE: 4
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480
ccagtacatg accttatggg actttcctac ttggcagtac atctacgtat tagtcatcgc 540
tattaccatg gtcgaggtga gccccacgtt ctgcttcact ctccccatct cccccccctc 600
cccaccccca attttgtatt tatttatttt ttaattattt tgtgcagcga tgggggcggg 660
gggggggggg gggcgcgcgc caggcggggc ggggcggggc gaggggcggg gcggggcgag 720
gcggagaggt gcggcggcag ccaatcagag cggcgcgctc cgaaagtttc cttttatggc 780
gaggcggcgg cggcggcggc cctataaaaa gcgaagcgcg cggcgggcgg gagtcgctgc 840
gttgccttcg ccccgtgccc cgctccgccg ccgcctcgcg ccgcccgccc cggctctgac 900
tgaccgcgtt actcccacag gtgagcgggc gggacggccc ttctcctccg ggctgtaatt 960
agcgcttggt ttaatgacgg cttgtttctt ttctgtggct gcgtgaaagc cttgaggggc 1020
tccgggaggg ccctttgtgc ggggggagcg gctcgggggg tgcgtgcgtg tgtgtgtgcg 1080
tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200
ggtgcggggg gggctgcgag gggaacaaag gctgcgtgcg gggtgtgtgc gtgggggggt 1260
gagcaggggg tgtgggcgcg tcggtcgggc tgcaaccccc cctgcacccc cctccccgag 1320
ttgctgagca cggcccggct tcgggtgcgg ggctccgtac ggggcgtggc gcggggctcg 1380
ccgtgccggg cgggggggtgg cggcaggtgg gggtgccggg cggggcgggg ccgcctcggg 1440
ccggggaggg ctcgggggag ggcgcggcgg gcccccggag cgccggcggc tgtcgaggcg 1500
cggcgagccg cagccattgc cttttatggt aatcgtgcga gagggcgcag ggacttcctt 1560
tgtcccaaat ctgtgcggag ccgaaatctg ggaggcgccg ccgcaccccc tctagcgggc 1620
gcggggcgaa gcggtgcggc gccggcagga aggaaatggg cggggagggc cttcgtgcgt 1680
cgccgcgccg ccgtcccctt ctccctctcc agcctcgggg ctgtccgcgg ggggacggct 1740
gccttcgggg gggacggggc agggcggggt tcggcttctg gcgtgtgacc ggcggctcta 1800
gagcctctgc taaccatgtt catgccttct tctttttcct acagctcctg ggcaacgtgc 1860
tggttattgt gctgtctcat cattttggca aagaattgat taattcgagc gaacgcgtgc 1920
caccatggct gctgtggtgg ctgccacaag atggtggcag ctgctgctgg tgctgagcgc 1980
cgctggaatg ggagcttctg gcgctcccca gccccccaat attctcctgc tgctgatgga 2040
cgacatgggc tggggcgatc tgggagtgta cggcgagcct agcagagaga cacccaacct 2100
ggacagaatg gccgccgagg gcctgctgtt ccccaacttc tacagcgcca accccctgtg 2160
cagcccatct agagccgctc tgctgaccgg cagactgccc atcagaaacg gcttctacac 2220
caccaacgcc cacgcccgga acgcctacac accccaggaa atcgtgggcg gcatccccga 2280

-continued

```
tagcgaacag ctgctgcctg agctgctgaa gaaagccggc tacgtgtcca agatcgtggg   2340
caagtggcac ctgggccaca gaccccagtt ccaccctctg aagcacggct tcgacgagtg   2400
gttcggcagc cccaattgcc acttcggccc ctacgacaac aaggccagac ccaacatccc   2460
cgtgtaccgg gactgggaga tggtgggacg gtactacgaa gagttcccca tcaacctgaa   2520
aaccggcgag gccaacctga cccagatcta cctgcaggaa gccctggact tcatcaagcg   2580
gcaggcccgg caccaccctt tctttctgta ctgggccgtg gacgccaccc acgcccctgt   2640
gtatgccagc aagcctttcc tgggcaccag ccagagaggc agatacggcg acgccgtgcg   2700
cgagatcgat gacagcatcg gcaagatcct ggaactgctg caggacctgc acgtggccga   2760
caacaccttc gtgttcttca ccagcgacaa cggcgctgcc ctgatctctg ctcctgagca   2820
gggcggcagc aacggcccat ttctgtgtgg caagcagacc accttcgagg gcggcatgag   2880
agaacctgcc ctggcttggt ggcctggcca tgtgacagct ggacaggtgt cccaccagct   2940
gggcagcatc atggacctgt tcaccaccag cctggccctg gccggactga cacctccaag   3000
cgacagagcc atcgacggcc tgaacctgct gcctaccctg ctgcagggac ggctgatgga   3060
ccggcccatc ttctactaca gaggcgacac cctgatggcc gccacactgg gacagcacaa   3120
ggcccacttt tggacctgga ccaacagctg ggagaacttc cggcagggca tcgacttttg   3180
ccctggccag aatgtgtccg gcgtgaccac ccacaacctg gaagatcaca ccaagctgcc   3240
cctgatttc  cacctgggca gagatcccgg cgagcggttc cctctgtctt ttgccagcgc   3300
cgagtaccag gaagctctga gcagaatcac ctccgtggtg cagcagcacc aggaagcact   3360
ggtgcctgct cagccccagc tgaacgtgtg caattgggcc gtgatgaact gggcccctcc   3420
cggctgtgaa aagctgggaa agtgcctgac ccccccctgag agcatcccca agaaatgcct   3480
gtggtcccac tgagaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gattttttt atattttgtt ttgtgttatt tttttcttta acatccctaa   3960
aattttcctt acatgtttta ctagccagat ttttcctcct ctcctgacta ctcccagtca   4020
tagctgtccc tcttctctta tggagatccc tcgacctgca gcccaagctg tagataagta   4080
gcatggcggg ttaatcatta actacaagga acccctagtg atggagttgg ccactccctc   4140
tctgcgcgct cgctcgctca ctgaggccgc ccgggctttg cccgggcggc ctcagtgagc   4200
gagcgagcgc gcagctgcat taatgaatcg gccaacgcgc ggggagaggc ggtttgcgta   4260
ttgggcgctc ttccgcttcc tcgctcactg actcgctgcg ctcggtcgtt cggctgcggc   4320
gagcggtatc agctcactca aaggcggtaa tacggttatc cacagaatca ggggataacg   4380
caggaaagaa catgtgagca aaaggccagc aaaaggccag gaaccgtaaa aaggccgcgt   4440
tgctggcgtt tttccatagg ctccgccccc ctgacgagca tcacaaaaat cgacgctcaa   4500
gtcagaggtg gcgaaacccg acaggactat aaagatacca ggcgtttccc cctggaagct   4560
ccctcgtgcg ctctcctgtt ccgaccctgc cgcttaccgg atacctgtcc gcctttctcc   4620
```

-continued

```
cttcgggaag cgtggcgctt tctcatagct cacgctgtag gtatctcagt tcggtgtagg   4680
tcgttcgctc caagctgggc tgtgtgcacg aaccccccgt tcagcccgac cgctgcgcct   4740
tatccggtaa ctatcgtctt gagtccaacc cggtaagaca cgacttatcg ccactggcag   4800
cagccactgg taacaggatt agcagagcga ggtatgtagg cggtgctaca gagttcttga   4860
agtggtggcc taactacggc tacactagaa gaacagtatt tggtatctgc gctctgctga   4920
agccagttac cttcggaaaa agagttggta gctcttgatc cggcaaacaa accaccgctg   4980
gtagcggtgg tttttttgtt tgcaagcagc agattacgcg cagaaaaaaa ggatctcaag   5040
aagatccttt gatcttttct acggggtctg acgctcagtg gaacgaaaac tcacgttaag   5100
ggattttggt catgagatta tcaaaaagga tcttcaccta gatcctttta aattaaaaat   5160
gaagttttaa atcaatctaa agtatatatg agtaaacttg gtctgacagt taccaatgct   5220
taatcagtga ggcacctatc tcagcgatct gtctatttcg ttcatccata gttgcctgac   5280
tccccgtcgt gtagataact acgatacggg agggcttacc atctggcccc agtgctgcaa   5340
tgataccgcg agacccacgc tcaccggctc cagatttatc agcaataaac cagccagccg   5400
gaagggccga gcgcagaagt ggtcctgcaa ctttatccgc ctccatccag tctattaatt   5460
gttgccggga agctagagta agtagttcgc cagttaatag tttgcgcaac gttgttgcca   5520
ttgctacagg catcgtggtg tcacgctcgt cgtttggtat ggcttcattc agctccggtt   5580
cccaacgatc aaggcgagtt acatgatccc ccatgttgtg caaaaaagcg gttagctcct   5640
tcggtcctcc gatcgttgtc agaagtaagt tggccgcagt gttatcactc atggttatgg   5700
cagcactgca taattctctt actgtcatgc catccgtaag atgcttttct gtgactggtg   5760
agtactcaac caagtcattc tgagaatagt gtatgcggcg accgagttgc tcttgcccgg   5820
cgtcaatacg ggataatacc gcgccacata gcagaacttt aaaagtgctc atcattggaa   5880
aacgttcttc ggggcgaaaa ctctcaagga tcttaccgct gttgagatcc agttcgatgt   5940
aacccactcg tgcacccaac tgatcttcag catcttttac tttcaccagc gtttctgggt   6000
gagcaaaaac aggaaggcaa aatgccgcaa aaaagggaat aagggcgaca cggaaatgtt   6060
gaatactcat actcttcctt tttcaatatt attgaagcat ttatcagggt tattgtctca   6120
tgagcggata catatttgaa tgtatttaga aaaataaaca aataggggtt ccgcgcacat   6180
ttccccgaaa agtgccacct gacgtctaag aaaccattat tatcatgaca ttaacctata   6240
aaaataggcg tatcacgagg ccctttcgtc tcgcgcgttt cggtgatgac ggtgaaaacc   6300
tctgacacat gcagctcccg gagacggtca cagcttgtct gtaagcggat gccgggagca   6360
gacaagcccg tcagggcgcg tcagcgggtg ttggcgggtg tcggggctgg cttaactatg   6420
cggcatcaga gcagattgta ctgagagtgc accatatgcg gtgtgaaata ccgcacagat   6480
gcgtaaggag aaaataccgc atcaggcgat tccaacatcc aataaatcat acaggcaagg   6540
caaagaatta gcaaaattaa gcaataaagc ctcagagcat aaagctaaat cggttgtacc   6600
aaaaacatta tgaccctgta atacttttgc gggagaagcc tttatttcaa cgcaaggata   6660
aaaattttta gaaccctcat atattttaaa tgcaatgcct gagtaatgtg taggtaaaga   6720
ttcaaacggg tgagaaaggc cggagacagt caaatcacca tcaatatgat attcaaccgt   6780
tctagctgat aaattcatgc cggagagggt agctattttt gagaggtctc tacaaaggct   6840
atcaggtcat tgcctgagag tctggagcaa acaagagaat cgatgaacgg taatcgtaaa   6900
actagcatgt caatcatatg taccccggtt gataatcaga aaagccccaa aaacaggaag   6960
attgtataag caaatattta aattgtaagc gttaatattt tgttaaaatt cgcgttaaat   7020
```

-continued ttttgttaaa tcagctcatt ttttaaccaa taggccgaaa tcggcaaaat cccttataaa 7080
tcaaaagaat agaccgagat agggttgagt gttgttccag tttggaacaa gagtccacta 7140
ttaaagaacg tggactccaa cgtcaaaggg cgaaaaaccg tctatcaggg cgatggccca 7200
ctacgtgaac catcacccta atcaagtttt ttggggtcga ggtgccgtaa agcactaaat 7260
cggaacccta aagggagccc ccgatttaga gcttgacggg gaaagccggc gaacgtggcg 7320
agaaaggaag ggaagaaagc gaaaggagcg ggcgctaggg cgctggcaag tgtagcggtc 7380
acgctgcgcg taaccaccac acccgccgcg cttaatgcgc cgctacaggg cgcgtactat 7440
ggttgctttg acgagcacgt ataacgtgct ttcctcgtta gaatcagagc gggagctaaa 7500
caggaggccg attaaaggga ttttagacag gaacggtacg ccagaatcct gagaagtgtt 7560
tttataatca gtgaggccac cgagtaaaag agtctgtcca tcacgcaaat taaccgttgt 7620
cgcaatactt ctttgattag taataacatc acttgcctga gtagaagaac tcaaactatc 7680
ggccttgctg gtaatatcca gaacaatatt accgccagcc attgcaacgg aatcgccatt 7740
cgccattcag gctgcgcaac tgttgggaag ggcgatcggt gcgggcctct tcgctattac 7800
gcca 7804

<210> SEQ ID NO 5
<211> LENGTH: 1577
<212> TYPE: DNA
<213> ORGANISM: Artificial Sequence
<220> FEATURE:
<223> OTHER INFORMATION: CDS ohGALNS-version2

<400> SEQUENCE: 5
tgccaccatg gccgccgtgg tcgccgcaac tcgatggtgg cagctgctgc tggtcctgtc 60
cgccgctggc atgggagcct ctggagcccc tcagcccccct aacatcctgc tgctgctgat 120
ggacgatatg ggatggggcg acctgggcgt gtacggagag ccaagccggg agacacccaa 180
tctggatagg atggcagcag agggcctgct gttcccaaac ttttattccg ccaatcctct 240
gtgcagccca tcccgcgccg ccctgctgac cggccggctg cccatcagaa acggcttcta 300
caccacaaac gcccacgccc ggaatgccta tacacctcag gagatcgtgg gcggcatccc 360
cgactctgag cagctgctgc ctgagctgct gaagaaggcc ggctacgtga gcaagatcgt 420
gggcaagtgg cacctgggac acaggccaca gttccaccct ctgaagcacg gcttcgatga 480
gtggtttggc agccccaatt gtcactttgg cccttacgac aacaaggcca gacccaatat 540
ccccgtgtac agagattggg agatggtggg caggtactat gaggagttcc ctatcaacct 600
gaagaccggc gaggccaatc tgacacagat ctacctgcag gaggccctgg actttatcaa 660
gaggcaggcc cgccaccacc ccttctttct gtactgggca gtggatgcaa cccacgcacc 720
agtgtatgcc tctaagccct tcctgggcac aagccagagg ggcagatatg gcgacgccgt 780
gagagagatc gacgattcta tcggcaagat cctggagctg ctgcaggacc tgcacgtggc 840
cgataacacc ttcgtgttct tcacatccga taatggagcc gccctgatct ccgccccaga 900
gcagggagga tctaacggac ccttcctgtg cggcaagcag accacatttg agggaggaat 960
gagggagcct gccctggcat ggtggccagg ccacgtgacc gccggccagg tgagccacca 1020
gctgggctcc atcatggacc tgttcaccac aagcctggcc ctggcaggcc tgaccccacc 1080
atccgacaga gccatcgatg gcctgaatct gctgcctaca ctgctgcagg gcaggctgat 1140
ggaccgccca atcttctact ataggggcga taccctgatg gcagccacac tgggacagca 1200

-continued caaggcacac ttttggacct ggacaaactc ctgggagaat ttccgccagg gcatcgattt 1260
ttgtccaggc cagaacgtgt ctggcgtgac cacacacaat ctggaggacc acaccaagct 1320
gcccctgatc tttcacctgg gccgggatcc tggcgagaga ttcccactgt cttttgccag 1380
cgccgagtac caggaggccc tgtcccggat cacatctgtg gtgcagcagc accaggaggc 1440
cctggtgcca gcacagcccc agctgaacgt gtgcaattgg gccgtgatga actgggcccc 1500
tccaggctgt gagaaactgg gcaaatgtct gactccccct gaatctatcc ctaagaagtg 1560
tctgtggtcc cattagg 1577

<210> SEQ ID NO 6
<211> LENGTH: 7804
<212> TYPE: DNA
<213> ORGANISM: Artificial Sequence
<220> FEATURE:
<223> OTHER INFORMATION: pAAV-CAG-ohGALNS-version2

<400> SEQUENCE: 6
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480
ccagtacatg accttatggg actttcctac ttggcagtac atctacgtat tagtcatcgc 540
tattaccatg gtcgaggtga gccccacgtt ctgcttcact ctccccatct cccccccctc 600
cccaccccca attttgtatt tatttatttt ttaattattt tgtgcagcga tgggggcggg 660
gggggggggg gggcgcgcgc caggcggggc ggggcggggc gaggggcggg gcggggcgag 720
gcggagaggt gcggcggcag ccaatcagag cggcgcgctc cgaaagtttc cttttatggc 780
gaggcggcgg cggcggcggc cctataaaaa gcgaagcgcg cggcgggcgg gagtcgctgc 840
gttgccttcg ccccgtgccc cgctccgccg ccgcctcgcg ccgcccgccc cggctctgac 900
tgaccgcgtt actcccacag gtgagcgggc gggacggccc ttctcctccg ggctgtaatt 960
agcgcttggt ttaatgacgg cttgtttctt ttctgtggct gcgtgaaagc cttgaggggc 1020
tccgggaggg ccctttgtgc ggggggagcg gctcgggggg tgcgtgcgtg tgtgtgtgcg 1080
tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200
ggtgcggggg gggctgcgag gggaacaaag gctgcgtgcg gggtgtgtgc gtgggggggt 1260
gagcaggggg tgtgggcgcg tcggtcgggc tgcaaccccc cctgcacccc cctccccgag 1320
ttgctgagca cggcccggct tcgggtgcgg ggctccgtac ggggcgtggc gcggggctcg 1380
ccgtgccggg cgggggtggc cggcaggtgg gggtgccggg cggggcgggg ccgcctcggg 1440
ccggggaggg ctcgggggag gggcgcggcg gcccccggag cgccggcggc tgtcgaggcg 1500
cggcgagccg cagccattgc cttttatggt aatcgtgcga gagggcgcag ggacttcctt 1560
tgtcccaaat ctgtgcggag ccgaaatctg ggaggcgccg ccgcaccccc tctagcgggc 1620
gcggggcgaa gcggtgcggc gccggcagga aggaaatggg cggggagggc cttcgtgcgt 1680

-continued

```
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggcc gccgtggtcg ccgcaactcg atggtggcag ctgctgctgg tcctgtccgc   1980
cgctggcatg ggagcctctg gagcccctca gccccctaac atcctgctgc tgctgatgga   2040
cgatatggga tggggcgacc tgggcgtgta cggagagcca agccgggaga cacccaatct   2100
ggataggatg gcagcagagg gcctgctgtt cccaaacttt tattccgcca atcctctgtg   2160
cagcccatcc cgcgccgccc tgctgaccgg ccggctgccc atcagaaacg gcttctacac   2220
cacaaacgcc cacgcccgga atgcctatac acctcaggag atcgtgggcg gcatccccga   2280
ctctgagcag ctgctgcctg agctgctgaa gaaggccggc tacgtgagca agatcgtggg   2340
caagtggcac ctgggacaca ggccacagtt ccaccctctg aagcacggct tcgatgagtg   2400
gtttggcagc cccaattgtc actttggccc ttacgacaac aaggccagac ccaatatccc   2460
cgtgtacaga gattgggaga tggtgggcag gtactatgag gagttcccta tcaacctgaa   2520
gaccggcgag gccaatctga cacagatcta cctgcaggag gccctggact ttatcaagag   2580
gcaggcccgc caccacccct tctttctgta ctgggcagtg gatgcaaccc acgcaccagt   2640
gtatgcctct aagcccttcc tgggcacaag ccagaggggc agatatggcg acgccgtgag   2700
agagatcgac gattctatcg gcaagatcct ggagctgctg caggacctgc acgtggccga   2760
taacaccttc gtgttcttca catccgataa tggagccgcc ctgatctccg ccccagagca   2820
gggaggatct aacggaccct tcctgtgcgg caagcagacc acatttgagg gaggaatgag   2880
ggagcctgcc ctggcatggt ggccaggcca cgtgaccgcc ggccaggtga gccaccagct   2940
gggctccatc atggacctgt tcaccacaag cctggccctg gcaggcctga ccccaccatc   3000
cgacagagcc atcgatggcc tgaatctgct gcctacactg ctgcagggca ggctgatgga   3060
ccgcccaatc ttctactata ggggcgatac cctgatggca gccacactgg gacagcacaa   3120
ggcacacttt tggacctgga caaactcctg ggagaatttc cgccagggca tcgatttttg   3180
tccaggccag aacgtgtctg gcgtgaccac acacaatctg gaggaccaca ccaagctgcc   3240
cctgatcttt cacctgggcc gggatcctgg cgagagattc ccactgtctt ttgccagcgc   3300
cgagtaccag gaggccctgt cccggatcac atctgtggtg cagcagcacc aggaggccct   3360
ggtgccagca cagccccagc tgaacgtgtg caattgggcc gtgatgaact gggcccctcc   3420
aggctgtgag aaactgggca aatgtctgac tccccctgaa tctatcccta agaagtgtct   3480
gtggtcccat taggaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gatttttttt atattttgtt ttgtgttatt tttttcttta acatccctaa   3960
aattttcctt acatgtttta ctagccagat ttttcctcct ctcctgacta ctcccagtca   4020
```

-continued

```
tagctgtccc tcttctctta tggagatccc tcgacctgca gcccaagctg tagataagta   4080
gcatggcggg ttaatcatta actacaagga acccctagtg atggagttgg ccactccctc   4140
tctgcgcgct cgctcgctca ctgaggccgc ccgggctttg cccgggcggc ctcagtgagc   4200
gagcgagcgc gcagctgcat taatgaatcg gccaacgcgc ggggagaggc ggtttgcgta   4260
ttgggcgctc ttccgcttcc tcgctcactg actcgctgcg ctcggtcgtt cggctgcggc   4320
gagcggtatc agctcactca aaggcggtaa tacggttatc cacagaatca ggggataacg   4380
caggaaagaa catgtgagca aaaggccagc aaaaggccag gaaccgtaaa aaggccgcgt   4440
tgctggcgtt tttccatagg ctccgccccc ctgacgagca tcacaaaaat cgacgctcaa   4500
gtcagaggtg gcgaaacccg acaggactat aaagatacca ggcgtttccc cctggaagct   4560
ccctcgtgcg ctctcctgtt ccgaccctgc cgcttaccgg atacctgtcc gcctttctcc   4620
cttcgggaag cgtggcgctt tctcatagct cacgctgtag gtatctcagt tcggtgtagg   4680
tcgttcgctc caagctgggc tgtgtgcacg aaccccccgt tcagcccgac cgctgcgcct   4740
tatccggtaa ctatcgtctt gagtccaacc cggtaagaca cgacttatcg ccactggcag   4800
cagccactgg taacaggatt agcagagcga ggtatgtagg cggtgctaca gagttcttga   4860
agtggtggcc taactacggc tacactagaa gaacagtatt tggtatctgc gctctgctga   4920
agccagttac cttcggaaaa agagttggta gctcttgatc cggcaaacaa accaccgctg   4980
gtagcggtgg tttttttgtt tgcaagcagc agattacgcg cagaaaaaaa ggatctcaag   5040
aagatccttt gatcttttct acggggtctg acgctcagtg gaacgaaaac tcacgttaag   5100
ggattttggt catgagatta tcaaaaagga tcttcaccta gatcctttta aattaaaaat   5160
gaagttttaa atcaatctaa agtatatatg agtaaacttg gtctgacagt taccaatgct   5220
taatcagtga ggcacctatc tcagcgatct gtctatttcg ttcatccata gttgcctgac   5280
tccccgtcgt gtagataact acgatacggg agggcttacc atctggcccc agtgctgcaa   5340
tgataccgcg agacccacgc tcaccggctc cagatttatc agcaataaac cagccagccg   5400
gaagggccga gcgcagaagt ggtcctgcaa ctttatccgc ctccatccag tctattaatt   5460
gttgccggga agctagagta agtagttcgc cagttaatag tttgcgcaac gttgttgcca   5520
ttgctacagg catcgtggtg tcacgctcgt cgtttggtat ggcttcattc agctccggtt   5580
cccaacgatc aaggcgagtt acatgatccc ccatgttgtg caaaaaagcg gttagctcct   5640
tcggtcctcc gatcgttgtc agaagtaagt tggccgcagt gttatcactc atggttatgg   5700
cagcactgca taattctctt actgtcatgc catccgtaag atgcttttct gtgactggtg   5760
agtactcaac caagtcattc tgagaatagt gtatgcggcg accgagttgc tcttgcccgg   5820
cgtcaatacg ggataatacc gcgccacata gcagaacttt aaaagtgctc atcattggaa   5880
aacgttcttc ggggcgaaaa ctctcaagga tcttaccgct gttgagatcc agttcgatgt   5940
aacccactcg tgcacccaac tgatcttcag catcttttac tttcaccagc gtttctgggt   6000
gagcaaaaac aggaaggcaa aatgccgcaa aaaagggaat aagggcgaca cggaaatgtt   6060
gaatactcat actcttcctt tttcaatatt attgaagcat ttatcagggt tattgtctca   6120
tgagcggata catatttgaa tgtatttaga aaaataaaca aataggggtt ccgcgcacat   6180
ttccccgaaa agtgccacct gacgtctaag aaaccattat tatcatgaca ttaacctata   6240
aaaataggcg tatcacgagg ccctttcgtc tcgcgcgttt cggtgatgac ggtgaaaacc   6300
tctgacacat gcagctcccg gagacggtca cagcttgtct gtaagcggat gccgggagca   6360
gacaagcccg tcagggcgcg tcagcgggtg ttggcgggtg tcggggctgg cttaactatg   6420
```

-continued

```
cggcatcaga gcagattgta ctgagagtgc accatatgcg gtgtgaaata ccgcacagat   6480

gcgtaaggag aaaataccgc atcaggcgat tccaacatcc aataaatcat acaggcaagg   6540

caaagaatta gcaaaattaa gcaataaagc ctcagagcat aaagctaaat cggttgtacc   6600

aaaaacatta tgaccctgta atacttttgc gggagaagcc tttatttcaa cgcaaggata   6660

aaaattttta gaaccctcat atattttaaa tgcaatgcct gagtaatgtg taggtaaaga   6720

ttcaaacggg tgagaaaggc cggagacagt caaatcacca tcaatatgat attcaaccgt   6780

tctagctgat aaattcatgc cggagagggt agctattttt gagaggtctc tacaaaggct   6840

atcaggtcat tgcctgagag tctggagcaa acaagagaat cgatgaacgg taatcgtaaa   6900

actagcatgt caatcatatg taccccggtt gataatcaga aaagccccaa aaacaggaag   6960

attgtataag caaatattta aattgtaagc gttaatattt tgttaaaatt cgcgttaaat   7020

ttttgttaaa tcagctcatt ttttaaccaa taggccgaaa tcggcaaaat cccttataaa   7080

tcaaaagaat agaccgagat agggttgagt gttgttccag tttggaacaa gagtccacta   7140

ttaaagaacg tggactccaa cgtcaaaggg cgaaaaaccg tctatcaggg cgatggccca   7200

ctacgtgaac catcacccta atcaagtttt ttggggtcga ggtgccgtaa agcactaaat   7260

cggaacccta aagggagccc ccgatttaga gcttgacggg gaaagccggc gaacgtggcg   7320

agaaaggaag ggaagaaagc gaaaggagcg ggcgctaggg cgctggcaag tgtagcggtc   7380

acgctgcgcg taaccaccac acccgccgcg cttaatgcgc cgctacaggg cgcgtactat   7440

ggttgctttg acgagcacgt ataacgtgct ttcctcgtta gaatcagagc gggagctaaa   7500

caggaggccg attaaaggga ttttagacag gaacggtacg ccagaatcct gagaagtgtt   7560

tttataatca gtgaggccac cgagtaaaag agtctgtcca tcacgcaaat taaccgttgt   7620

cgcaatactt ctttgattag taataacatc acttgcctga gtagaagaac tcaaactatc   7680

ggccttgctg gtaatatcca gaacaatatt accgccagcc attgcaacgg aatcgccatt   7740

cgccattcag gctgcgcaac tgttgggaag ggcgatcggt gcgggcctct tcgctattac   7800

gcca                                                                7804
```

<210> SEQ ID NO 7
<211> LENGTH: 1577
<212> TYPE: DNA
<213> ORGANISM: Artificial Sequence
<220> FEATURE:
<223> OTHER INFORMATION: CDS ohGALNS-version3

<400> SEQUENCE: 7

```
tgccaccatg gcagcggtgg tggccgcgac cagatggtgg cagcttctcc tggtcctgtc     60

ggccgcggga atgggtgcct cgggcgcgcc gcagcccccct aacattctgc tgctgctgat    120

ggacgatatg ggatggggcg acctgggggt gtacggagag ccttcacggg aaaccccccaa    180

cctggaccgc atggcggctg aaggcctgct gttcccgaac ttttactccg cgaatccgct    240

gtgctcccct tcgcgcgccg ccctcctgac cggacggttg cctatccgca acggcttcta    300

cactactaac gcacacgcca ggaacgccta cacccccgcaa gaaattgtgg gaggaatccc    360

ggattccgaa cagctgctgc cggaactgct gaagaaggcc ggctacgtgt cgaagatcgt    420

gggaaagtgg catcttggtc atcggcctca gttccacccg ctcaagcacg ggttcgatga    480

atggttcgga tcccccaact gccactttgg cccctacgac aacaaggctc ggcctaacat    540

tcccgtctac cgggactggg aaatggtcgg aagatactac gaggagttcc ccatcaacct    600
```

-continued

```
caagactggc gaagccaacc tgactcagat ctacctccaa gaggccctgg acttcatcaa    660
gcgccaggcc cggcaccacc cgttcttcct ctattgggcg gtggacgcca cccatgcccc    720
cgtgtacgca tcaaagccgt tccttggaac tagccagaga ggcagatacg ggatgccgt    780
gcgcgaaatt gatgactcca tcggaaagat cctggagctg ctccaggacc tccatgtcgc    840
cgacaatacc ttcgtgttct ttacttccga taacggcgcc gccttgatca gcgccccgga    900
gcagggaggc tccaacggcc cttttctctg tgggaaacag accaccttcg agggagggat    960
gcgggaaccg gctctggctt ggtggcccgg acacgtgacc gccggccaag tgtcgcacca   1020
gcttggctcc atcatggact tgttcaccac ctcactggcc ctcgcggggc tcaccccacc   1080
aagcgaccga gcgattgacg gtctgaactt gctccccact ctgctgcaag gaaggctgat   1140
ggaccggccc atcttctact atcggggcga taccttgatg gccgccaccc tgggacagca   1200
caaggcccac ttttggactt ggacaaactc ctgggagaac ttccgccaag ggatcgactt   1260
ctgccccggt caaaacgtgt ccggcgtgac cacccacaac ctggaggacc ataccaagct   1320
gccactgatt ttccaccttg gtcgggaccc aggagagaga ttcccactga gcttcgcctc   1380
cgccgaatat caggaagcac tgtcccggat cacgagcgtg gtgcagcagc atcaggaggc   1440
cctggtgccg gcgcagccgc agctcaatgt ctgcaactgg gctgtgatga actgggcacc   1500
ccctggctgc gaaaaactcg ggaagtgtct gactccacct gagagcatcc cgaagaagtg   1560
cctgtggagc cactagg                                                  1577

<210> SEQ ID NO 8
<211> LENGTH: 7804
<212> TYPE: DNA
<213> ORGANISM: Artificial Sequence
<220> FEATURE:
<223> OTHER INFORMATION: pAAV-CAG-ohGALNS-version3

<400> SEQUENCE: 8

gctgcgcgct cgctcgctca ctgaggccgc ccgggcaaag cccgggcgtc gggcgacctt     60
tggtcgcccg gcctcagtga gcgagcgagc gcgcagagag ggagtggcca actccatcac    120
taggggttcc ttgtagttaa tgattaaccc gccatgctac ttatctactc gacattgatt    180
attgactagt tattaatagt aatcaattac ggggtcatta gttcatagcc catatatgga    240
gttccgcgtt acataactta cggtaaatgg cccgcctggc tgaccgccca acgacccccg    300
cccattgacg tcaataatga cgtatgttcc catagtaacg ccaataggga ctttccattg    360
acgtcaatgg gtggagtatt tacggtaaac tgcccacttg gcagtacatc aagtgtatca    420
tatgccaagt acgcccccta ttgacgtcaa tgacggtaaa tggcccgcct ggcattatgc    480
ccagtacatg accttatggg actttcctac ttggcagtac atctacgtat tagtcatcgc    540
tattaccatg gtcgaggtga gccccacgtt ctgcttcact ctccccatct cccccccctc    600
cccaccccca attttgtatt tatttatttt ttaattattt tgtgcagcga tgggggcggg    660
gggggggggg gggcgcgcgc caggcggggc ggggcggggc gaggggcggg gcggggcgag    720
gcggagaggt gcggcggcag ccaatcagag cggcgcgctc cgaaagtttc cttttatggc    780
gaggcggcgg cggcggcggc cctataaaaa gcgaagcgcg cggcgggcgg gagtcgctgc    840
gttgccttcg ccccgtgccc cgctccgccg ccgcctcgcg ccgcccgccc cggctctgac    900
tgaccgcgtt actcccacag gtgagcgggc gggacggccc ttctcctccg ggctgtaatt    960
agcgcttggt ttaatgacgg cttgtttctt ttctgtggct gcgtgaaagc cttgaggggc   1020
tccgggaggg ccctttgtgc ggggggagcg gctcgggggg tgcgtgcgtg tgtgtgtgcg   1080
```

-continued tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200
ggtgcggggg gggctgcgag gggaacaaag gctgcgtgcg ggtgtgtgc gtgggggggt 1260 gagcaggggg tgtgggcgcg tcggtcgggc tgcaaccccc cctgcacccc cctccccgag 1320
ttgctgagca cggcccggct tcgggtgcgg ggctccgtac ggggcgtggc gcggggctcg 1380
ccgtgccggg cggggggtgg cggcaggtgg gggtgccggg cggggcgggg ccgcctcggg 1440
ccggggaggg ctcgggggag ggcgcggcg gcccccggag cgccggcggc tgtcgaggcg 1500
cggcgagccg cagccattgc cttttatggt aatcgtgcga gagggcgcag ggacttcctt 1560
tgtcccaaat ctgtgcggag ccgaaatctg ggaggcgccg ccgcaccccc tctagcgggc 1620
gcggggcgaa gcggtgcggc gccggcagga aggaaatggg cggggagggc cttcgtgcgt 1680
cgccgcgccg ccgtcccctt ctccctctcc agcctcgggg ctgtccgcgg ggggacggct 1740
gccttcgggg gggacggggc agggcggggt tcggcttctg gcgtgtgacc ggcggctcta 1800
gagcctctgc taaccatgtt catgccttct tctttttcct acagctcctg ggcaacgtgc 1860
tggttattgt gctgtctcat cattttggca aagaattgat taattcgagc gaacgcgtgc 1920
caccatggca gcggtggtgg ccgcgaccag atggtggcag cttctcctgg tcctgtcggc 1980
cgcgggaatg ggtgcctcgg gcgcgccgca gccccctaac attctgctgc tgctgatgga 2040
cgatatggga tggggcgacc tgggggtgta cggagagcct tcacgggaaa cccccaacct 2100
ggaccgcatg gcggctgaag gcctgctgtt cccgaacttt tactccgcga atccgctgtg 2160
ctccccttcg cgcgccgccc tcctgaccgg acggttgcct atccgcaacg gcttctacac 2220
tactaacgca cacgccagga acgcctacac cccgcaagaa attgtgggag gaatcccgga 2280
ttccgaacag ctgctgccgg aactgctgaa gaaggccggc tacgtgtcga agatcgtggg 2340
aaagtggcat cttggtcatc ggcctcagtt ccacccgctc aagcacgggt tcgatgaatg 2400
gttcggatcc cccaactgcc actttggccc ctacgacaac aaggctcggc ctaacattcc 2460
cgtctaccgg gactgggaaa tggtcggaag atactacgag gagttcccca tcaacctcaa 2520
gactggcgaa gccaacctga ctcagatcta cctccaagag gccctggact tcatcaagcg 2580
ccaggcccgg caccacccgt tcttcctcta ttgggcggtg gacgccaccc atgcccccgt 2640
gtacgcatca aagccgttcc ttggaactag ccagagaggc agatacgggg atgccgtgcg 2700
cgaaattgat gactccatcg gaaagatcct ggagctgctc caggacctcc atgtcgccga 2760
caataccttc gtgttcttta cttccgataa cggcgccgcc ttgatcagcg ccccggagca 2820
gggaggctcc aacggccctt ttctctgtgg gaaacagacc accttcgagg gagggatgcg 2880
ggaaccggct ctggcttggt ggcccggaca cgtgaccgcc ggccaagtgt cgcaccagct 2940
tggctccatc atggacttgt tcaccacctc actggccctc gcggggctca ccccaccaag 3000
cgaccgagcg attgacggtc tgaacttgct ccccactctg ctgcaaggaa ggctgatgga 3060
ccggcccatc ttctactatc ggggcgatac cttgatggcc gccaccctgg gacagcacaa 3120
ggcccacttt tggacttgga caaactcctg ggagaacttc cgccaaggga tcgacttctg 3180
ccccggtcaa aacgtgtccg gcgtgaccac ccacaacctg gaggaccata ccaagctgcc 3240
actgattttc caccttggtc gggacccagg agagagattc ccactgagct tcgcctccgc 3300
cgaatatcag gaagcactgt cccggatcac gagcgtggtg cagcagcatc aggaggccct 3360
ggtgccggcg cagccgcagc tcaatgtctg caactgggct gtgatgaact gggcaccccc 3420

-continued

```
tggctgcgaa aaactcggga agtgtctgac tccacctgag agcatcccga agaagtgcct   3480
gtggagccac taggaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gatttttttt atattttgtt ttgtgttatt tttttcttta acatccctaa   3960
aattttcctt acatgtttta ctagccagat ttttcctcct ctcctgacta ctcccagtca   4020
tagctgtccc tcttctctta tggagatccc tcgacctgca gcccaagctg tagataagta   4080
gcatggcggg ttaatcatta actacaagga acccctagtg atggagttgg ccactccctc   4140
tctgcgcgct cgctcgctca ctgaggccgc ccgggctttg cccgggcggc ctcagtgagc   4200
gagcgagcgc gcagctgcat taatgaatcg gccaacgcgc ggggagaggc ggtttgcgta   4260
ttgggcgctc ttccgcttcc tcgctcactg actcgctgcg ctcggtcgtt cggctgcggc   4320
gagcggtatc agctcactca aaggcggtaa tacggttatc cacagaatca ggggataacg   4380
caggaaagaa catgtgagca aaaggccagc aaaaggccag gaaccgtaaa aaggccgcgt   4440
tgctggcgtt tttccatagg ctccgccccc ctgacgagca tcacaaaaat cgacgctcaa   4500
gtcagaggtg gcgaaacccg acaggactat aaagatacca ggcgtttccc cctggaagct   4560
ccctcgtgcg ctctcctgtt ccgaccctgc cgcttaccgg atacctgtcc gcctttctcc   4620
cttcgggaag cgtggcgctt tctcatagct cacgctgtag gtatctcagt tcggtgtagg   4680
tcgttcgctc caagctgggc tgtgtgcacg aaccccccgt tcagcccgac cgctgcgcct   4740
tatccggtaa ctatcgtctt gagtccaacc cggtaagaca cgacttatcg ccactggcag   4800
cagccactgg taacaggatt agcagagcga ggtatgtagg cggtgctaca gagttcttga   4860
agtggtggcc taactacggc tacactagaa gaacagtatt tggtatctgc gctctgctga   4920
agccagttac cttcggaaaa agagttggta gctcttgatc cggcaaacaa accaccgctg   4980
gtagcggtgg tttttttgtt tgcaagcagc agattacgcg cagaaaaaaa ggatctcaag   5040
aagatccttt gatcttttct acggggtctg acgctcagtg gaacgaaaac tcacgttaag   5100
ggattttggt catgagatta tcaaaaagga tcttcaccta gatcctttta aattaaaaat   5160
gaagttttaa atcaatctaa agtatatatg agtaaacttg gtctgacagt taccaatgct   5220
taatcagtga ggcacctatc tcagcgatct gtctatttcg ttcatccata gttgcctgac   5280
tccccgtcgt gtagataact acgatacggg agggcttacc atctggcccc agtgctgcaa   5340
tgataccgcg agacccacgc tcaccggctc cagatttatc agcaataaac cagccagccg   5400
gaagggccga gcgcagaagt ggtcctgcaa ctttatccgc ctccatccag tctattaatt   5460
gttgccggga agctagagta agtagttcgc cagttaatag tttgcgcaac gttgttgcca   5520
ttgctacagg catcgtggtg tcacgctcgt cgtttggtat ggcttcattc agctccggtt   5580
cccaacgatc aaggcgagtt acatgatccc ccatgttgtg caaaaaagcg gttagctcct   5640
tcggtcctcc gatcgttgtc agaagtaagt tggccgcagt gttatcactc atggttatgg   5700
cagcactgca taattctctt actgtcatgc catccgtaag atgcttttct gtgactggtg   5760
agtactcaac caagtcattc tgagaatagt gtatgcggcg accgagttgc tcttgcccgg   5820
```

-continued

```
cgtcaatacg ggataatacc gcgccacata gcagaacttt aaaagtgctc atcattggaa   5880

aacgttcttc ggggcgaaaa ctctcaagga tcttaccgct gttgagatcc agttcgatgt   5940

aacccactcg tgcacccaac tgatcttcag catcttttac tttcaccagc gtttctgggt   6000

gagcaaaaac aggaaggcaa aatgccgcaa aaaagggaat aagggcgaca cggaaatgtt   6060

gaatactcat actcttcctt tttcaatatt attgaagcat ttatcagggt tattgtctca   6120

tgagcggata catatttgaa tgtatttaga aaaataaaca aataggggtt ccgcgcacat   6180

ttccccgaaa agtgccacct gacgtctaag aaaccattat tatcatgaca ttaacctata   6240

aaaataggcg tatcacgagg ccctttcgtc tcgcgcgttt cggtgatgac ggtgaaaacc   6300

tctgacacat gcagctcccg gagacggtca cagcttgtct gtaagcggat gccgggagca   6360

gacaagcccg tcagggcgcg tcagcgggtg ttggcgggtg tcggggctgg cttaactatg   6420

cggcatcaga gcagattgta ctgagagtgc accatatgcg gtgtgaaata ccgcacagat   6480

gcgtaaggag aaaataccgc atcaggcgat tccaacatcc aataaatcat acaggcaagg   6540

caaagaatta gcaaaattaa gcaataaagc ctcagagcat aaagctaaat cggttgtacc   6600

aaaaacatta tgaccctgta atacttttgc gggagaagcc tttatttcaa cgcaaggata   6660

aaaattttta gaaccctcat atattttaaa tgcaatgcct gagtaatgtg taggtaaaga   6720

ttcaaacggg tgagaaaggc cggagacagt caaatcacca tcaatatgat attcaaccgt   6780

tctagctgat aaattcatgc cggagagggt agctattttt gagaggtctc tacaaaggct   6840

atcaggtcat tgcctgagag tctggagcaa acaagagaat cgatgaacgg taatcgtaaa   6900

actagcatgt caatcatatg taccccggtt gataatcaga aaagccccaa aaacaggaag   6960

attgtataag caaatattta aattgtaagc gttaatattt tgttaaaatt cgcgttaaat   7020

ttttgttaaa tcagctcatt ttttaaccaa taggccgaaa tcggcaaaat cccttataaa   7080

tcaaaagaat agaccgagat agggttgagt gttgttccag tttggaacaa gagtccacta   7140

ttaaagaacg tggactccaa cgtcaaaggg cgaaaaaccg tctatcaggg cgatggccca   7200

ctacgtgaac catcacccta atcaagtttt ttggggtcga ggtgccgtaa agcactaaat   7260

cggaacccta aagggagccc ccgatttaga gcttgacggg gaaagccggc gaacgtggcg   7320

agaaaggaag ggaagaaagc gaaaggagcg ggcgctaggg cgctggcaag tgtagcggtc   7380

acgctgcgcg taaccaccac acccgccgcg cttaatgcgc cgctacaggg cgcgtactat   7440

ggttgctttg acgagcacgt ataacgtgct ttcctcgtta gaatcagagc gggagctaaa   7500

caggaggccg attaaaggga ttttagacag gaacggtacg ccagaatcct gagaagtgtt   7560

tttataatca gtgaggccac cgagtaaaag agtctgtcca tcacgcaaat taaccgttgt   7620

cgcaatactt ctttgattag taataacatc acttgcctga gtagaagaac tcaaactatc   7680

ggccttgctg gtaatatcca gaacaatatt accgccagcc attgcaacgg aatcgccatt   7740

cgccattcag gctgcgcaac tgttgggaag ggcgatcggt gcgggcctct tcgctattac   7800

gcca                                                                7804
```

<210> SEQ ID NO 9
<211> LENGTH: 1563
<212> TYPE: DNA
<213> ORGANISM: Artificial Sequence
<220> FEATURE:
<223> OTHER INFORMATION: CDS omGALNS

<400> SEQUENCE: 9

-continued atggctgctt gtacagccgc tcagcagctg ctgctggtgc tgtctgctct gggactgctg 60
gctgctggcg ctcctcagcc tcctaacatc gtgctgctgc tgatggacga catgggctgg 120
ggcgatctgg gagtgaacgg cgagcctagc agagagacac ccaacctgga cagaatggcc 180
gccgagggca tgctgttccc cagcttctac agcgccaacc ccctgtgcag cccttctaga 240
gccgctctgc tgaccggcag actgcccatc agaaacggct tctacaccac caacgcccac 300
gccagaaacg cctacacacc ccaggaaatc atgggcggca tccccaacag cgagcatctg 360
ctgcctgagc tgctgaagaa ggccggctac accaacaaga tcgtgggcaa gtggcacctg 420
ggccacagac cccagttcca ccctctgaag cacggcttcg acgagtggtt cggcagcccc 480
aactgtcact tcggccccta cgacaacaag gccaagccca acatccccgt gtacagagac 540
tgggagatgg tgggaagatt ctacgaagag ttccccatca acagaaagac cggcgaggcc 600
aacctgaccc agctgtacac acaggaagcc ctggacttca tccagaccca gcacgccaga 660
cagagcccct tcttcctgta ctgggccatc gacgccacac acgcccctgt gtacgccagc 720
agacagttcc tgggcaccag cctgagaggc agatatggcg acgccgtgcg cgagatcgac 780
gactctgtgg gcaagatcct gtccctgctg cagaacctgg gcatcagcaa gaacaccttc 840
gtgttcttca ccagcgacaa cggcgctgcc ctgatcagcg ctcctaatga gggcggcagc 900
aacggcccat tcctgtgcgg caagcagacc acattcgagg gcggaatgag agagcccgct 960
atcgcttggt ggcctggcca tatcgctgct ggccaggtgt cacaccagct gggcagcatc 1020
atggacctgt tcaccacctc cctgagcctg gccggactga agcctcctag cgacagagtg 1080
atcgacggcc tggacctgct gcccaccatg ctgaagggcc agatgatgga cagacccatc 1140
ttctactaca gaggcaacac cctgatggcc gtgaccctgg gccagtacaa ggcccacctg 1200
tggacctgga ccaacagctg ggaagagttt acccagggca ccgatttctg ccctggccag 1260
aatgtgtccg gcgtgaccac ccacacccag gaagaacaca ccgagctgcc cctgatcttc 1320
cacctgggaa gggaccccgg cgagagattc cctctgagct tccacagcga cgagtaccag 1380
gacgccctga gcagaaccac ccaggtggtg caggaacacc agaaaagcct ggtgcccggc 1440
cagccccagc tgaacgtgtg taaccaggcc gtgatgaact gggcccctcc cggatgtgaa 1500
aagctgggaa agtgcctgac ccccccctgag agcgtgcccg agaagtgttt ctgggcccac 1560
tga 1563

<210> SEQ ID NO 10
<211> LENGTH: 7798
<212> TYPE: DNA
<213> ORGANISM: Artificial Sequence
<220> FEATURE:
<223> OTHER INFORMATION: pAAV-CAG-omGALNS

<400> SEQUENCE: 10
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480

-continued

```
ccagtacatg accttatggg actttcctac ttggcagtac atctacgtat tagtcatcgc    540
tattaccatg gtcgaggtga gccccacgtt ctgcttcact ctccccatct cccccccctc    600
cccaccccca attttgtatt tatttatttt ttaattattt tgtgcagcga tgggggcggg    660
gggggggggg gggcgcgcgc caggcggggc ggggcggggc gaggggcggg gcggggcgag    720
gcggagaggt gcggcggcag ccaatcagag cggcgcgctc cgaaagtttc cttttatggc    780
gaggcggcgg cggcggcggc cctataaaaa gcgaagcgcg cggcgggcgg gagtcgctgc    840
gttgccttcg ccccgtgccc cgctccgccg ccgcctcgcg ccgcccgccc cggctctgac    900
tgaccgcgtt actcccacag gtgagcgggc gggacggccc ttctcctccg ggctgtaatt    960
agcgcttggt ttaatgacgg cttgtttctt ttctgtggct gcgtgaaagc cttgaggggc   1020
tccgggaggg ccctttgtgc ggggggagcg gctcgggggg tgcgtgcgtg tgtgtgtgcg   1080
tggggagcgc cgcgtgcggc tccgcgctgc ccggcggctg tgagcgctgc gggcgcggcg   1140
cggggctttg tgcgctccgc agtgtgcgcg aggggagcgc ggccgggggc ggtgccccgc   1200
ggtgcggggg gggctgcgag gggaacaaag gctgcgtgcg gggtgtgtgc gtgggggggt   1260
gagcaggggg tgtgggcgcg tcggtcgggc tgcaaccccc cctgcacccc cctccccgag   1320
ttgctgagca cggcccggct tcgggtgcgg ggctccgtac ggggcgtggc gcggggctcg   1380
ccgtgccggg cgggggtgg cggcaggtgg gggtgccggg cggggcgggg ccgcctcggg   1440
ccggggaggg ctcgggggag ggcgcggcg gcccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggct gcttgtacag ccgctcagca gctgctgctg gtgctgtctg ctctgggact   1980
gctggctgct ggcgctcctc agcctcctaa catcgtgctg ctgctgatgg acgacatggg   2040
ctggggcgat ctgggagtga acggcgagcc tagcagagag acacccaacc tggacagaat   2100
ggccgccgag ggcatgctgt tccccagctt ctacagcgcc aacccccctgt gcagcccttc   2160
tagagccgct ctgctgaccg gcagactgcc catcagaaac ggcttctaca ccaccaacgc   2220
ccacgccaga aacgcctaca caccccagga aatcatgggc ggcatcccca acagcgagca   2280
tctgctgcct gagctgctga agaaggccgg ctacaccaac aagatcgtgg gcaagtggca   2340
cctgggccac agaccccagt tccaccctct gaagcacggc ttcgacgagt ggttcggcag   2400
ccccaactgt cacttcggcc cctacgacaa caaggccaag cccaacatcc ccgtgtacag   2460
agactgggag atggtgggaa gattctacga agagttcccc atcaacagaa agaccggcga   2520
ggccaacctg acccagctgt acacacagga agccctggac ttcatccaga cccagcacgc   2580
cagacagagc cccttcttcc tgtactgggc catcgacgcc acacacgccc ctgtgtacgc   2640
cagcagacag ttcctgggca ccagcctgag aggcagatat ggcgacgccg tgcgcgagat   2700
cgacgactct gtgggcaaga tcctgtccct gctgcagaac ctgggcatca gcaagaacac   2760
cttcgtgttc ttcaccagcg acaacggcgc tgccctgatc agcgctccta atgagggcgg   2820
```

-continued

```
cagcaacggc ccattcctgt gcggcaagca gaccacattc gagggcggaa tgagagagcc   2880
cgctatcgct tggtggcctg gccatatcgc tgctggccag gtgtcacacc agctgggcag   2940
catcatggac ctgttcacca cctccctgag cctggccgga ctgaagcctc ctagcgacag   3000
agtgatcgac ggcctggacc tgctgcccac catgctgaag ggccagatga tggacagacc   3060
catcttctac tacagaggca acaccctgat ggccgtgacc ctgggccagt acaaggccca   3120
cctgtggacc tggaccaaca gctgggaaga gtttacccag ggcaccgatt tctgccctgg   3180
ccagaatgtg tccggcgtga ccacccacac ccaggaagaa cacaccgagc tgcccctgat   3240
cttccacctg ggaagggacc ccggcgagag attccctctg agcttccaca gcgacgagta   3300
ccaggacgcc ctgagcagaa ccacccaggt ggtgcaggaa caccagaaaa gcctggtgcc   3360
cggccagccc cagctgaacg tgtgtaacca ggccgtgatg aactgggccc ctcccggatg   3420
tgaaaagctg ggaaagtgcc tgaccccccc tgagagcgtg cccgagaagt gtttctgggc   3480
ccactgagaa ttcgagctcg gtacccggga atcaattcac tcctcaggtg caggctgcct   3540
atcagaaggt ggtggctggt gtggccaatg ccctggctca caaataccac tgagatcttt   3600
ttccctctgc caaaaattat ggggacatca tgaagcccct tgagcatctg acttctggct   3660
aataaaggaa atttattttc attgcaatag tgtgttggaa tttttgtgt ctctcactcg   3720
gaaggacata tgggagggca aatcatttaa aacatcagaa tgagtatttg gtttagagtt   3780
tggcaacata tgcccatatg ctggctgcca tgaacaaagg ttggctataa agaggtcatc   3840
agtatatgaa acagcccccct gctgtccatt ccttattcca tagaaaagcc ttgacttgag   3900
gttagatttt ttttatattt tgttttgtgt tatttttttc tttaacatcc ctaaaatttt   3960
ccttacatgt tttactagcc agatttttcc tcctctcctg actactccca gtcatagctg   4020
tccctcttct cttatggaga tccctcgacc tgcagcccaa gctgtagata agtagcatgg   4080
cgggttaatc attaactaca aggaacccct agtgatggag ttggccactc cctctctgcg   4140
cgctcgctcg ctcactgagg ccgcccgggc tttgcccggg cggcctcagt gagcgagcga   4200
gcgcgcagct gcattaatga atcggccaac gcgcggggag aggcggtttg cgtattgggc   4260
gctcttccgc ttcctcgctc actgactcgc tgcgctcggt cgttcggctg cggcgagcgg   4320
tatcagctca ctcaaaggcg gtaatacggt tatccacaga atcaggggat aacgcaggaa   4380
agaacatgtg agcaaaaggc cagcaaaagg ccaggaaccg taaaaaggcc gcgttgctgg   4440
cgtttttcca taggctccgc ccccctgacg agcatcacaa aaatcgacgc tcaagtcaga   4500
ggtggcgaaa cccgacagga ctataaagat accaggcgtt tccccctgga agctccctcg   4560
tgcgctctcc tgttccgacc ctgccgctta ccggatacct gtccgccttt ctcccttcgg   4620
gaagcgtggc gctttctcat agctcacgct gtaggtatct cagttcggtg taggtcgttc   4680
gctccaagct gggctgtgtg cacgaacccc ccgttcagcc cgaccgctgc gccttatccg   4740
gtaactatcg tcttgagtcc aacccggtaa gacacgactt atcgccactg gcagcagcca   4800
ctggtaacag gattagcaga gcgaggtatg taggcggtgc tacagagttc ttgaagtggt   4860
ggcctaacta cggctacact agaagaacag tatttggtat ctgcgctctg ctgaagccag   4920
ttaccttcgg aaaaagagtt ggtagctctt gatccggcaa acaaaccacc gctggtagcg   4980
gtggtttttt tgtttgcaag cagcagatta cgcgcagaaa aaaaggatct caagaagatc   5040
ctttgatctt ttctacgggg tctgacgctc agtggaacga aaactcacgt taagggattt   5100
tggtcatgag attatcaaaa aggatcttca cctagatcct tttaaattaa aaatgaagtt   5160
ttaaatcaat ctaaagtata tatgagtaaa cttggtctga cagttaccaa tgcttaatca   5220
```

-continued

```
gtgaggcacc tatctcagcg atctgtctat ttcgttcatc catagttgcc tgactccccg   5280
tcgtgtagat aactacgata cgggagggct taccatctgg ccccagtgct gcaatgatac   5340
cgcgagaccc acgctcaccg gctccagatt tatcagcaat aaaccagcca gccggaaggg   5400
ccgagcgcag aagtggtcct gcaactttat ccgcctccat ccagtctatt aattgttgcc   5460
gggaagctag agtaagtagt tcgccagtta atagtttgcg caacgttgtt gccattgcta   5520
caggcatcgt ggtgtcacgc tcgtcgtttg gtatggcttc attcagctcc ggttcccaac   5580
gatcaaggcg agttacatga tcccccatgt tgtgcaaaaa agcggttagc tccttcggtc   5640
ctccgatcgt tgtcagaagt aagttggccg cagtgttatc actcatggtt atggcagcac   5700
tgcataattc tcttactgtc atgccatccg taagatgctt ttctgtgact ggtgagtact   5760
caaccaagtc attctgagaa tagtgtatgc ggcgaccgag ttgctcttgc ccggcgtcaa   5820
tacgggataa taccgcgcca catagcagaa ctttaaaagt gctcatcatt ggaaaacgtt   5880
cttcggggcg aaaactctca aggatcttac cgctgttgag atccagttcg atgtaaccca   5940
ctcgtgcacc caactgatct tcagcatctt ttactttcac cagcgtttct gggtgagcaa   6000
aaacaggaag gcaaaatgcc gcaaaaaagg gaataagggc gacacggaaa tgttgaatac   6060
tcatactctt cctttttcaa tattattgaa gcatttatca gggttattgt ctcatgagcg   6120
gatacatatt tgaatgtatt tagaaaaata aacaaatagg ggttccgcgc acatttcccc   6180
gaaaagtgcc acctgacgtc taagaaacca ttattatcat gacattaacc tataaaaata   6240
ggcgtatcac gaggcccttt cgtctcgcgc gtttcggtga tgacggtgaa aacctctgac   6300
acatgcagct cccggagacg gtcacagctt gtctgtaagc ggatgccggg agcagacaag   6360
cccgtcaggg cgcgtcagcg ggtgttggcg ggtgtcgggg ctggcttaac tatgcggcat   6420
cagagcagat tgtactgaga gtgcaccata tgcggtgtga aataccgcac agatgcgtaa   6480
ggagaaaata ccgcatcagg cgattccaac atccaataaa tcatacaggc aaggcaaaga   6540
attagcaaaa ttaagcaata aagcctcaga gcataaagct aaatcggttg taccaaaaac   6600
attatgaccc tgtaatactt ttgcgggaga agcctttatt tcaacgcaag gataaaaatt   6660
tttagaaccc tcatatattt taaatgcaat gcctgagtaa tgtgtaggta aagattcaaa   6720
cgggtgagaa aggccggaga cagtcaaatc accatcaata tgatattcaa ccgttctagc   6780
tgataaattc atgccggaga gggtagctat ttttgagagg tctctacaaa ggctatcagg   6840
tcattgcctg agagtctgga gcaaacaaga gaatcgatga acggtaatcg taaaactagc   6900
atgtcaatca tatgtacccc ggttgataat cagaaaagcc ccaaaaacag gaagattgta   6960
taagcaaata tttaaattgt aagcgttaat attttgttaa aattcgcgtt aaatttttgt   7020
taaatcagct cattttttaa ccaataggcc gaaatcggca aaatccctta taaatcaaaa   7080
gaatagaccg agatagggtt gagtgttgtt ccagtttgga acaagagtcc actattaaag   7140
aacgtggact ccaacgtcaa agggcgaaaa accgtctatc agggcgatgg cccactacgt   7200
gaaccatcac cctaatcaag ttttttgggg tcgaggtgcc gtaaagcact aaatcggaac   7260
cctaaaggga gcccccgatt tagagcttga cggggaaagc cggcgaacgt ggcgagaaag   7320
gaagggaaga aagcgaaagg agcgggcgct agggcgctgg caagtgtagc ggtcacgctg   7380
cgcgtaacca ccacacccgc cgcgcttaat gcgccgctac agggcgcgta ctatggttgc   7440
tttgacgagc acgtataacg tgctttcctc gttagaatca gagcgggagc taaacaggag   7500
gccgattaaa gggattttag acaggaacgg tacgccagaa tcctgagaag tgtttttata   7560
```

-continued atcagtgagg ccaccgagta aaagagtctg tccatcacgc aaattaaccg ttgtcgcaat 7620
acttctttga ttagtaataa catcacttgc ctgagtagaa gaactcaaac tatcggcctt 7680
gctggtaata tccagaacaa tattaccgcc agccattgca acggaatcgc cattcgccat 7740
tcaggctgcg caactgttgg gaagggcgat cggtgcgggc ctcttcgcta ttacgcca 7798

<210> SEQ ID NO 11
<211> LENGTH: 7438
<212> TYPE: DNA
<213> ORGANISM: Artificial Sequence
<220> FEATURE:
<223> OTHER INFORMATION: pAAV-hAAT-omGALNS

<400> SEQUENCE: 11
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagg atctgatatc atcgatgaat tcgagctcgg tacccggccg cagatttagg 240
tgacactata gaatatgcat cactagtaag cttgcgaatt ccagtctaca gagaggtctc 300
tgacctctgc ccagctccca aggtcagcag gcagggaggg ctgtgtgttt gctgtttgct 360
gcttgcaatg tttgcccatt ttagggacat gagtaggctg aagtttgttc agtgtggact 420
tcagaggcag cacacaaaca gcaagcttgc gaattccagt ctacagagag gtctctgacc 480
tctgccccag ctccaaggtc agcaggcagg gagggctgtg tgtttgctgt ttgctgcttg 540
caatgtttgc ccattttagg gacatgagta ggctgaagtt tgttcagtgt ggacttcaga 600
ggcagcacac aaacagcaag cttgcgaatt ccagtctaca gagaggtctc tgacctctgc 660
cccagctcca aggtcagcag gcagggaggg ctgtgtgttt gctgtttgct gcttgcaatg 720
tttgcccatt ttagggacat gagtaggctg aagtttgttc agtgtggact tcagaggcag 780
cacacaaaca gcaagctttg ctctagactg gaattcgtcg acgagctccc tatagtgagt 840
cgtattagag gccgactgac ccggtacccg ggatcttgc taccagtgga acagccacta 900
aggattctgc agtgagagca gagggccagc taagtggtac tctcccagag actgtctgac 960
tcacgccacc ccctccacct tggacacagg acgctgtggt ttctgagcca ggtacaatga 1020
ctcctttcgg taagtgcagt ggaagctgta cactgcccag gcaaagcgtc cgggcagcgt 1080
aggcgggcga ctcagatccc agccagtgga cttagcccct gtttgctcct ccgataactg 1140
gggtgacctt ggttaatatt caccagcagc ctcccccgtt gcccctctgg atccactgct 1200
taaatacgga cgaggacagg gccctgtctc ctcagcttca ggcaccacca ctgacctggg 1260
acagtgaatg tccccctgat ctgcggccgt gactctctta aggtagcctt gcagaagttg 1320
gtcgtgaggc actgggcagg taagtatcaa ggttacaaga caggtttaag gagaccaata 1380
gaaactgggc ttgtcgagac agagaagact cttgcgtttc tgataggcac ctattggtct 1440
tactgacatc cactttgcct ttctctccac aggtgtccac tcccagttca attacagctc 1500
ttaaggctag agtacttaat acgactcact ataggctagc ctcgacctcg agacgcgtgc 1560
caccatggct gcttgtacag ccgctcagca gctgctgctg gtgctgtctg ctctgggact 1620
gctggctgct ggcgctcctc agcctcctaa catcgtgctg ctgctgatgg acgacatggg 1680
ctggggcgat ctgggagtga acggcgagcc tagcagagag acacccaacc tggacagaat 1740
ggccgccgag ggcatgctgt tccccagctt ctacagcgcc aaccccctgt gcagcccttc 1800
tagagccgct ctgctgaccg gcagactgcc catcagaaac ggcttctaca ccaccaacgc 1860

```
ccacgccaga aacgcctaca caccccagga aatcatgggc ggcatcccca acagcgagca   1920
tctgctgcct gagctgctga agaaggccgg ctacaccaac aagatcgtgg gcaagtggca   1980
cctgggccac agaccccagt tccaccctct gaagcacggc ttcgacgagt ggttcggcag   2040
ccccaactgt cacttcggcc cctacgacaa caaggccaag cccaacatcc ccgtgtacag   2100
agactgggag atggtgggaa gattctacga agagttcccc atcaacagaa agaccggcga   2160
ggccaacctg acccagctgt acacacagga agccctggac ttcatccaga cccagcacgc   2220
cagacagagc cccttcttcc tgtactgggc catcgacgcc acacacgccc ctgtgtacgc   2280
cagcagacag ttcctgggca ccagcctgag aggcagatat ggcgacgccg tgcgcgagat   2340
cgacgactct gtgggcaaga tcctgtccct gctgcagaac ctgggcatca gcaagaacac   2400
cttcgtgttc ttcaccagcg acaacggcgc tgccctgatc agcgctccta atgagggcgg   2460
cagcaacggc ccattcctgt gcggcaagca gaccacattc gagggcggaa tgagagagcc   2520
cgctatcgct tggtggcctg gccatatcgc tgctggccag gtgtcacacc agctgggcag   2580
catcatggac ctgttcacca cctccctgag cctggccgga ctgaagcctc ctagcgacag   2640
agtgatcgac ggcctggacc tgctgcccac catgctgaag ggccagatga tggacagacc   2700
catcttctac tacagaggca acaccctgat ggccgtgacc ctgggccagt acaaggccca   2760
cctgtggacc tggaccaaca gctgggaaga gtttacccag ggcaccgatt tctgccctgg   2820
ccagaatgtg tccggcgtga ccacccacac ccaggaagaa cacaccgagc tgcccctgat   2880
cttccacctg ggaagggacc ccggcgagag attccctctg agcttccaca gcgacgagta   2940
ccaggacgcc ctgagcagaa ccacccaggt ggtgcaggaa caccagaaaa gcctggtgcc   3000
cggccagccc cagctgaacg tgtgtaacca ggccgtgatg aactgggccc ctcccggatg   3060
tgaaaagctg ggaaagtgcc tgaccccccc tgagagcgtg cccgagaagt gtttctgggc   3120
ccactgagaa ttcgagctcg gtacccggga atcaattcac tcctcaggtg caggctgcct   3180
atcagaaggt ggtggctggt gtggccaatg ccctggctca caaataccac tgagatcttt   3240
ttccctctgc caaaaattat ggggacatca tgaagcccct tgagcatctg acttctggct   3300
aataaaggaa atttattttc attgcaatag tgtgttggaa ttttttgtgt ctctcactcg   3360
gaaggacata tgggagggca aatcatttaa aacatcagaa tgagtatttg gtttagagtt   3420
tggcaacata tgcccatatg ctggctgcca tgaacaaagg ttggctataa agaggtcatc   3480
agtatatgaa acagcccccct gctgtccatt ccttattcca tagaaaagcc ttgacttgag   3540
gttagatttt ttttatattt tgttttgtgt tattttttttc tttaacatcc ctaaaatttt   3600
ccttacatgt tttactagcc agatttttcc tcctctcctg actactccca gtcatagctg   3660
tccctcttct cttatggaga tccctcgacc tgcagcccaa gctgtagata agtagcatgg   3720
cgggttaatc attaactaca aggaacccct agtgatggag ttggccactc cctctctgcg   3780
cgctcgctcg ctcactgagg ccgcccgggc tttgcccggg cggcctcagt gagcgagcga   3840
gcgcgcagct gcattaatga atcggccaac gcgcggggag aggcggtttg cgtattgggc   3900
gctcttccgc ttcctcgctc actgactcgc tgcgctcggt cgttcggctg cggcgagcgg   3960
tatcagctca ctcaaaggcg gtaatacggt tatccacaga atcaggggat aacgcaggaa   4020
agaacatgtg agcaaaaggc cagcaaaagg ccaggaaccg taaaaaggcc gcgttgctgg   4080
cgtttttcca taggctccgc ccccctgacg agcatcacaa aaatcgacgc tcaagtcaga   4140
ggtggcgaaa cccgacagga ctataaagat accaggcgtt tccccctgga agctccctcg   4200
```

-continued

```
tgcgctctcc tgttccgacc ctgccgctta ccggatacct gtccgccttt ctcccttcgg   4260
gaagcgtggc gctttctcat agctcacgct gtaggtatct cagttcggtg taggtcgttc   4320
gctccaagct gggctgtgtg cacgaacccc ccgttcagcc cgaccgctgc gccttatccg   4380
gtaactatcg tcttgagtcc aacccggtaa gacacgactt atcgccactg gcagcagcca   4440
ctggtaacag gattagcaga gcgaggtatg taggcggtgc tacagagttc ttgaagtggt   4500
ggcctaacta cggctacact agaagaacag tatttggtat ctgcgctctg ctgaagccag   4560
ttaccttcgg aaaaagagtt ggtagctctt gatccggcaa acaaaccacc gctggtagcg   4620
gtggtttttt tgtttgcaag cagcagatta cgcgcagaaa aaaaggatct caagaagatc   4680
ctttgatctt ttctacgggg tctgacgctc agtggaacga aaactcacgt taagggattt   4740
tggtcatgag attatcaaaa aggatcttca cctagatcct tttaaattaa aaatgaagtt   4800
ttaaatcaat ctaaagtata tatgagtaaa cttggtctga cagttaccaa tgcttaatca   4860
gtgaggcacc tatctcagcg atctgtctat ttcgttcatc catagttgcc tgactccccg   4920
tcgtgtagat aactacgata cgggagggct taccatctgg ccccagtgct gcaatgatac   4980
cgcgagaccc acgctcaccg gctccagatt tatcagcaat aaaccagcca gccggaaggg   5040
ccgagcgcag aagtggtcct gcaactttat ccgcctccat ccagtctatt aattgttgcc   5100
gggaagctag agtaagtagt tcgccagtta atagtttgcg caacgttgtt gccattgcta   5160
caggcatcgt ggtgtcacgc tcgtcgtttg gtatggcttc attcagctcc ggttcccaac   5220
gatcaaggcg agttacatga tcccccatgt tgtgcaaaaa agcggttagc tccttcggtc   5280
ctccgatcgt tgtcagaagt aagttggccg cagtgttatc actcatggtt atggcagcac   5340
tgcataattc tcttactgtc atgccatccg taagatgctt ttctgtgact ggtgagtact   5400
caaccaagtc attctgagaa tagtgtatgc ggcgaccgag ttgctcttgc ccggcgtcaa   5460
tacgggataa taccgcgcca catagcagaa ctttaaaagt gctcatcatt ggaaaacgtt   5520
cttcggggcg aaaactctca aggatcttac cgctgttgag atccagttcg atgtaaccca   5580
ctcgtgcacc caactgatct tcagcatctt ttactttcac cagcgtttct gggtgagcaa   5640
aaacaggaag gcaaaatgcc gcaaaaaagg gaataagggc gacacggaaa tgttgaatac   5700
tcatactctt cctttttcaa tattattgaa gcatttatca gggttattgt ctcatgagcg   5760
gatacatatt tgaatgtatt tagaaaaata aacaaatagg ggttccgcgc acatttcccc   5820
gaaaagtgcc acctgacgtc taagaaacca ttattatcat gacattaacc tataaaaata   5880
ggcgtatcac gaggcccttt cgtctcgcgc gtttcggtga tgacggtgaa aacctctgac   5940
acatgcagct cccggagacg gtcacagctt gtctgtaagc ggatgccggg agcagacaag   6000
cccgtcaggg cgcgtcagcg ggtgttggcg ggtgtcgggg ctggcttaac tatgcggcat   6060
cagagcagat tgtactgaga gtgcaccata tgcggtgtga aataccgcac agatgcgtaa   6120
ggagaaaata ccgcatcagg cgattccaac atccaataaa tcatacaggc aaggcaaaga   6180
attagcaaaa ttaagcaata aagcctcaga gcataaagct aaatcggttg taccaaaaac   6240
attatgaccc tgtaatactt ttgcgggaga agcctttatt tcaacgcaag gataaaaatt   6300
tttagaaccc tcatatattt taaatgcaat gcctgagtaa tgtgtaggta aagattcaaa   6360
cgggtgagaa aggccggaga cagtcaaatc accatcaata tgatattcaa ccgttctagc   6420
tgataaattc atgccggaga gggtagctat ttttgagagg tctctacaaa ggctatcagg   6480
tcattgcctg agagtctgga gcaaacaaga gaatcgatga acggtaatcg taaaactagc   6540
atgtcaatca tatgtacccc ggttgataat cagaaaagcc ccaaaaacag gaagattgta   6600
```

-continued taagcaaata tttaaattgt aagcgttaat attttgttaa aattcgcgtt aaatttttgt 6660
taaatcagct cattttttaa ccaataggcc gaaatcggca aaatccctta taaatcaaaa 6720
gaatagaccg agatagggtt gagtgttgtt ccagtttgga acaagagtcc actattaaag 6780
aacgtggact ccaacgtcaa agggcgaaaa accgtctatc agggcgatgg cccactacgt 6840
gaaccatcac cctaatcaag ttttttgggg tcgaggtgcc gtaaagcact aaatcggaac 6900
cctaaaggga gcccccgatt tagagcttga cggggaaagc cggcgaacgt ggcgagaaag 6960
gaagggaaga aagcgaaagg agcgggcgct agggcgctgg caagtgtagc ggtcacgctg 7020
cgcgtaacca ccacacccgc cgcgcttaat gcgccgctac agggcgcgta ctatggttgc 7080
tttgacgagc acgtataacg tgctttcctc gttagaatca gagcgggagc taaacaggag 7140
gccgattaaa gggattttag acaggaacgg tacgccagaa tcctgagaag tgtttttata 7200
atcagtgagg ccaccgagta aaagagtctg tccatcacgc aaattaaccg ttgtcgcaat 7260
acttctttga ttagtaataa catcacttgc ctgagtagaa gaactcaaac tatcggcctt 7320
gctggtaata tccagaacaa tattaccgcc agccattgca acggaatcgc cattcgccat 7380
tcaggctgcg caactgttgg gaagggcgat cggtgcgggc ctcttcgcta ttacgcca 7438

<210> SEQ ID NO 12
<211> LENGTH: 4215
<212> TYPE: DNA
<213> ORGANISM: Artificial Sequence
<220> FEATURE:
<223> OTHER INFORMATION: AAV9-CAG-hGALNS

<400> SEQUENCE: 12
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480
ccagtacatg accttatggg actttcctac ttggcagtac atctacgtat tagtcatcgc 540
tattaccatg gtcgaggtga gccccacgtt ctgcttcact ctccccatct cccccccctc 600
cccaccccca attttgtatt tatttatttt ttaattattt tgtgcagcga tgggggcggg 660
gggggggggg ggcgcgcgcc aggcggggcg gggcggggcg aggggcgggg gcggggcgag 720
gcggagaggt gcggcggcag ccaatcagag cggcgcgctc cgaaagtttc cttttatggc 780
gaggcggcgg cggcggcggc cctataaaaa gcgaagcgcg cggcgggcgg gagtcgctgc 840
gttgccttcg ccccgtgccc cgctccgccg ccgcctcgcg ccgcccgccc cggctctgac 900
tgaccgcgtt actcccacag gtgagcgggc gggacggccc ttctcctccg ggctgtaatt 960
agcgcttggt ttaatgacgg cttgtttctt ttctgtggct gcgtgaaagc cttgaggggc 1020
tccgggaggg ccctttgtgc ggggggagcg gctcgggggg tgcgtgcgtg tgtgtgtgcg 1080
tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200

-continued

```
ggtgcggggg gggctgcgag gggaacaaag gctgcgtgcg gggtgtgtgc gtgggggggt   1260
gagcaggggg tgtgggcgcg tcggtcgggc tgcaaccccc cctgcacccc cctccccgag   1320
ttgctgagca cggcccggct tcgggtgcgg ggctccgtac ggggcgtggc gcggggctcg   1380
ccgtgccggg cggggggtgg cggcaggtgg gggtgccggg cggggcgggg ccgcctcggg   1440
ccggggaggg ctcgggggag ggcgcggcg gcccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggcg gcggttgtcg cggcgacgag gtggtggcag ctgttgctgg tgctcagcgc   1980
cgcggggatg gggcctcgg gcgccccgca gcccccaac atcctgctcc tgctcatgga   2040
cgacatggga tggggtgacc tcggggtgta tggagagccc tccagagaga ccccgaattt   2100
ggaccggatg gctgcagaag ggctgctttt cccaaacttc tattctgcca accctctgtg   2160
ctcgccatcg agggcggcac tgctcacagg acggctaccc atccgcaatg gcttctacac   2220
caccaacgcc catgccagaa acgcctacac accgcaggag attgtgggcg gcatcccaga   2280
ctcggagcag ctcctgccgg agcttctgaa gaaggccggc tacgtcagca agattgtcgg   2340
caagtggcat ctgggtcaca ggccccagtt ccaccccctg aagcacggat ttgatgagtg   2400
gtttggatcc cccaactgcc actttggacc ttatgacaac aaggccaggc ccaacatccc   2460
tgtgtacagg gactgggaga tggttggcag atattatgaa gaatttccta ttaatctgaa   2520
gacgggggaa gccaacctca cccagatcta cctgcaggaa gccctggact tcattaagag   2580
acaggcacgg caccacccct ttttcctcta ctgggctgtc gacgccacgc acgcacccgt   2640
ctatgcctcc aaacccttct tgggcaccag tcagcgaggg cggtatggag acgccgtccg   2700
ggagattgat gacagcattg ggaagatact ggagctcctc caagacctgc acgtcgcgga   2760
caacaccttc gtcttcttca cgtcggacaa cggcgctgcc ctcatttccg cccccgaaca   2820
aggtggcagc aacggcccct ttctgtgtgg gaagcagacc acgtttgaag gagggatgag   2880
ggagcctgcc ctcgcatggt ggccagggca cgtcactgca ggccaggtga gccaccagct   2940
gggcagcatc atggacctct tcaccaccag cctggccctt gcgggcctga cgccgcccag   3000
cgacagggcc attgatggcc tcaacctcct ccccaccctc ctgcagggcc ggctgatgga   3060
caggcctatc ttctattacc gtggcgacac gctgatggcg gccaccctcg ggcagcacaa   3120
ggctcacttc tggacctgga ccaactcctg ggagaacttc agacagggca ttgatttctg   3180
ccctgggcag aacgtttcag gggtcacaac tcacaatctg gaagaccaca cgaagctgcc   3240
cctgatcttc cacctgggac gggacccagg ggagaggttc cccctcagct ttgccagcgc   3300
cgagtaccag gaggccctca gcaggatcac ctcggtcgtc cagcagcacc aggaggcctt   3360
ggtccccgcg cagccccagc tcaacgtgtg caactgggcg gtcatgaact gggcacctcc   3420
gggctgtgaa aagttaggga agtgtctgac acctccagaa tccattccca agaagtgcct   3480
ctggtcccac taggaattcg agctcggtac ccgggaatca attcactcct caggtgcagg   3540
ctgcctatca gaaggtggtg gctggtgtgg ccaatgccct ggctcacaaa taccactgag   3600
```

```
atctttttcc ctctgccaaa aattatgggg acatcatgaa gccccttgag catctgactt   3660

ctggctaata aaggaaattt attttcattg caatagtgtg ttggaatttt ttgtgtctct   3720

cactcggaag gacatatggg agggcaaatc atttaaaaca tcagaatgag tatttggttt   3780

agagtttggc aacatatgcc catatgctgg ctgccatgaa caaaggttgg ctataaagag   3840

gtcatcagta tatgaaacag ccccctgctg tccattcctt attccataga aaagccttga   3900

cttgaggtta gatttttttt atattttgtt ttgtgttatt tttttcttta acatccctaa   3960

aattttcctt acatgtttta ctagccagat ttttcctcct ctcctgacta ctcccagtca   4020

tagctgtccc tcttctctta tggagatccc tcgacctgca gcccaagctg tagataagta   4080

gcatggcggg ttaatcatta actacaagga acccctagtg atggagttgg ccactccctc   4140

tctgcgcgct cgctcgctca ctgaggccgc ccgggctttg cccgggcggc ctcagtgagc   4200

gagcgagcgc gcagc                                                     4215
```

<210> SEQ ID NO 13
<211> LENGTH: 4215
<212> TYPE: DNA
<213> ORGANISM: Artificial Sequence
<220> FEATURE:
<223> OTHER INFORMATION: AAV9-CAG-ohGALNS-version1

<400> SEQUENCE: 13

```
gctgcgcgct cgctcgctca ctgaggccgc ccgggcaaag cccgggcgtc gggcgacctt     60

tggtcgcccg gcctcagtga gcgagcgagc gcgcagagag ggagtggcca actccatcac    120

taggggttcc ttgtagttaa tgattaaccc gccatgctac ttatctactc gacattgatt    180

attgactagt tattaatagt aatcaattac ggggtcatta gttcatagcc catatatgga    240

gttccgcgtt acataactta cggtaaatgg cccgcctggc tgaccgccca acgacccccg    300

cccattgacg tcaataatga cgtatgttcc catagtaacg ccaataggga ctttccattg    360

acgtcaatgg gtggagtatt tacggtaaac tgcccacttg gcagtacatc aagtgtatca    420

tatgccaagt acgcccccta ttgacgtcaa tgacggtaaa tggcccgcct ggcattatgc    480

ccagtacatg accttatggg actttcctac ttggcagtac atctacgtat tagtcatcgc    540

tattaccatg gtcgaggtga gccccacgtt ctgcttcact ctccccatct cccccccctc    600

cccaccccca attttgtatt tatttatttt ttaattattt tgtgcagcga tgggggcggg    660

gggggggggg gggcgcgcgc caggcggggc ggggcggggc gaggggcggg gcggggcgag    720

gcggagaggt gcggcggcag ccaatcagag cggcgcgctc cgaaagtttc cttttatggc    780

gaggcggcgg cggcggcggc cctataaaaa gcgaagcgcg cggcgggcgg gagtcgctgc    840

gttgccttcg ccccgtgccc cgctccgccg ccgcctcgcg ccgcccgccc cggctctgac    900

tgaccgcgtt actcccacag gtgagcgggc gggacggccc ttctcctccg ggctgtaatt    960

agcgcttggt ttaatgacgg cttgtttctt ttctgtggct gcgtgaaagc cttgaggggc   1020

tccgggaggg ccctttgtgc ggggggagcg gctcgggggg tgcgtgcgtg tgtgtgtgcg   1080

tggggagcgc cgcgtgcggc tccgcgctgc ccggcggctg tgagcgctgc gggcgcggcg   1140

cggggctttg tgcgctccgc agtgtgcgcg aggggagcgc ggccgggggc ggtgccccgc   1200

ggtgcggggg gggctgcgag gggaacaaag gctgcgtgcg gggtgtgtgc gtgggggggt   1260

gagcaggggg tgtgggcgcg tcggtcgggc tgcaaccccc cctgcacccc cctccccgag   1320

ttgctgagca cggcccggct tcgggtgcgg ggctccgtac ggggcgtggc gcggggctcg   1380
```

-continued

```
ccgtgccggg cggggggtgg cggcaggtgg gggtgccggg cggggcgggg ccgcctcggg   1440
ccggggaggg ctcgggggag gggcgcggcg gcccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggct gctgtggtgg ctgccacaag atggtggcag ctgctgctgg tgctgagcgc   1980
cgctggaatg ggagcttctg gcgctcccca gcccccccaat attctcctgc tgctgatgga   2040
cgacatgggc tggggcgatc tgggagtgta cggcgagcct agcagagaga cacccaacct   2100
ggacagaatg gccgccgagg gcctgctgtt ccccaacttc tacagcgcca accccctgtg   2160
cagcccatct agagccgctc tgctgaccgg cagactgccc atcagaaacg gcttctacac   2220
caccaacgcc cacgcccgga acgcctacac accccaggaa atcgtgggcg gcatccccga   2280
tagcgaacag ctgctgcctg agctgctgaa gaaagccggc tacgtgtcca agatcgtggg   2340
caagtggcac ctgggccaca gaccccagtt ccaccctctg aagcacggct tcgacgagtg   2400
gttcggcagc ccccaattgcc acttcggccc ctacgacaac aaggccagac ccaacatccc   2460
cgtgtaccgg gactgggaga tggtgggacg gtactacgaa gagttcccca tcaacctgaa   2520
aaccggcgag gccaacctga cccagatcta cctgcaggaa gccctggact tcatcaagcg   2580
gcaggcccgg caccaccctt tctttctgta ctgggccgtg gacgccaccc acgcccctgt   2640
gtatgccagc aagcctttcc tgggcaccag ccagagaggc agatacggcg acgccgtgcg   2700
cgagatcgat gacagcatcg gcaagatcct ggaactgctg caggacctgc acgtggccga   2760
caacaccttc gtgttcttca ccagcgacaa cggcgctgcc ctgatctctg ctcctgagca   2820
gggcggcagc aacggcccat ttctgtgtgg caagcagacc accttcgagg gcggcatgag   2880
agaacctgcc ctggcttggt ggcctggcca tgtgacagct ggacaggtgt cccaccagct   2940
gggcagcatc atggacctgt tcaccaccag cctggccctg gccggactga cacctccaag   3000
cgacagagcc atcgacggcc tgaacctgct gcctaccctg ctgcagggac ggctgatgga   3060
ccggcccatc ttctactaca gaggcgacac cctgatggcc gccacactgg gacagcacaa   3120
ggcccacttt tggacctgga ccaacagctg ggagaacttc cggcagggca tcgacttttg   3180
ccctggccag aatgtgtccg gcgtgaccac ccacaacctg gaagatcaca ccaagctgcc   3240
cctgattttc cacctgggca gagatcccgg cgagcggttc cctctgtctt ttgccagcgc   3300
cgagtaccag gaagctctga gcagaatcac ctccgtggtg cagcagcacc aggaagcact   3360
ggtgcctgct cagccccagc tgaacgtgtg caattgggcc gtgatgaact gggcccctcc   3420
cggctgtgaa aagctgggaa agtgcctgac ccccccctgag agcatcccca agaaatgcct   3480
gtggtcccac tgagaattcg agctcggtac ccgggaatca attcactcct caggtgcagg   3540
ctgcctatca gaaggtggtg gctggtgtgg ccaatgccct ggctcacaaa taccactgag   3600
atcttttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
```

-continued agagtttggc aacatatgcc catatgctgg ctgccatgaa caaaggttgg ctataaagag 3840
gtcatcagta tatgaaacag ccccctgctg tccattcctt attccataga aaagccttga 3900
cttgaggtta gattttttt atattttgtt ttgtgttatt tttttcttta acatccctaa 3960
aattttcctt acatgtttta ctagccagat ttttcctcct ctcctgacta ctcccagtca 4020
tagctgtccc tcttctctta tggagatccc tcgacctgca gcccaagctg tagataagta 4080
gcatggcggg ttaatcatta actacaagga acccctagtg atggagttgg ccactccctc 4140
tctgcgcgct cgctcgctca ctgaggccgc ccgggctttg cccgggcggc ctcagtgagc 4200
gagcgagcgc gcagc 4215

<210> SEQ ID NO 14
<211> LENGTH: 4215
<212> TYPE: DNA
<213> ORGANISM: Artificial Sequence
<220> FEATURE:
<223> OTHER INFORMATION: AAV9-CAG-ohGALNS-version2

<400> SEQUENCE: 14
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480
ccagtacatg accttatggg actttcctac ttggcagtac atctacgtat tagtcatcgc 540
tattaccatg gtcgaggtga gccccacgtt ctgcttcact ctccccatct cccccccctc 600
cccaccccca attttgtatt tatttatttt ttaattattt tgtgcagcga tgggggcggg 660
gggggggggg gggcgcgcgc caggcggggc ggggcggggc gaggggcggg gcggggcgag 720
gcggagaggt gcggcggcag ccaatcagag cggcgcgctc cgaaagtttc cttttatggc 780
gaggcggcgg cggcggcggc cctataaaaa gcgaagcgcg cggcgggcgg gagtcgctgc 840
gttgccttcg ccccgtgccc cgctccgccg ccgcctcgcg ccgcccgccc cggctctgac 900
tgaccgcgtt actcccacag gtgagcgggc gggacggccc ttctcctccg ggctgtaatt 960
agcgcttggt ttaatgacgg cttgtttctt ttctgtggct gcgtgaaagc cttgaggggc 1020
tccgggaggg ccctttgtgc ggggggagcg gctcgggggg tgcgtgcgtg tgtgtgtgcg 1080
tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200
ggtgcggggg gggctgcgag gggaacaaag gctgcgtgcg gggtgtgtgc gtgggggggt 1260
gagcaggggg tgtgggcgcg tcggtcgggc tgcaaccccc cctgcacccc cctccccgag 1320
ttgctgagca cggcccggct tcgggtgcgg ggctccgtac ggggcgtggc gcggggctcg 1380
ccgtgccggg cggggggtgg cggcaggtgg gggtgccggg cggggcgggg ccgcctcggg 1440
ccggggaggg ctcgggggag gggcgcggcg gcccccggag cgccggcggc tgtcgaggcg 1500
cggcgagccg cagccattgc cttttatggt aatcgtgcga gagggcgcag ggacttcctt 1560

-continued

```
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggcc gccgtggtcg ccgcaactcg atggtggcag ctgctgctgg tcctgtccgc   1980
cgctggcatg ggagcctctg gagcccctca gccccctaac atcctgctgc tgctgatgga   2040
cgatatggga tggggcgacc tgggcgtgta cggagagcca agccgggaga cacccaatct   2100
ggataggatg gcagcagagg gcctgctgtt cccaaacttt tattccgcca atcctctgtg   2160
cagcccatcc cgcgccgccc tgctgaccgg ccggctgccc atcagaaacg gcttctacac   2220
cacaaacgcc cacgcccgga atgcctatac acctcaggag atcgtgggcg gcatccccga   2280
ctctgagcag ctgctgcctg agctgctgaa gaaggccggc tacgtgagca agatcgtggg   2340
caagtggcac ctgggacaca ggccacagtt ccaccctctg aagcacggct tcgatgagtg   2400
gtttggcagc ccccaattgtc actttggccc ttacgacaac aaggccagac ccaatatccc   2460
cgtgtacaga gattgggaga tggtgggcag gtactatgag gagttcccta tcaacctgaa   2520
gaccggcgag gccaatctga cacagatcta cctgcaggag gccctggact ttatcaagag   2580
gcaggcccgc caccacccct tctttctgta ctgggcagtg gatgcaaccc acgcaccagt   2640
gtatgcctct aagcccttcc tgggcacaag ccagaggggc agatatggcg acgccgtgag   2700
agagatcgac gattctatcg gcaagatcct ggagctgctg caggacctgc acgtggccga   2760
taacaccttc gtgttcttca catccgataa tggagccgcc ctgatctccg ccccagagca   2820
gggaggatct aacggaccct tcctgtgcgg caagcagacc acatttgagg gaggaatgag   2880
ggagcctgcc ctggcatggt ggccaggcca cgtgaccgcc ggccaggtga gccaccagct   2940
gggctccatc atggacctgt tcaccacaag cctggccctg gcaggcctga ccccaccatc   3000
cgacagagcc atcgatggcc tgaatctgct gcctacactg ctgcagggca ggctgatgga   3060
ccgcccaatc ttctactata ggggcgatac cctgatggca gccacactgg gacagcacaa   3120
ggcacacttt tggacctgga caaactcctg ggagaatttc cgccagggca tcgatttttg   3180
tccaggccag aacgtgtctg gcgtgaccac acacaatctg gaggaccaca ccaagctgcc   3240
cctgatcttt cacctgggcc gggatcctgg cgagagattc ccactgtctt ttgccagcgc   3300
cgagtaccag gaggccctgt cccggatcac atctgtggtg cagcagcacc aggaggccct   3360
ggtgccagca cagccccagc tgaacgtgtg caattgggcc gtgatgaact gggcccctcc   3420
aggctgtgag aaactgggca aatgtctgac tccccctgaa tctatcccta agaagtgtct   3480
gtggtcccat taggaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gatttttttt atattttgtt ttgtgttatt tttttcttta acatccctaa   3960
```

```
aattttcctt acatgtttta ctagccagat ttttcctcct ctcctgacta ctcccagtca   4020

tagctgtccc tcttctctta tggagatccc tcgacctgca gcccaagctg tagataagta   4080

gcatggcggg ttaatcatta actacaagga acccctagtg atggagttgg ccactccctc   4140

tctgcgcgct cgctcgctca ctgaggccgc ccgggctttg cccgggcggc ctcagtgagc   4200

gagcgagcgc gcagc                                                    4215


<210> SEQ ID NO 15
<211> LENGTH: 4215
<212> TYPE: DNA
<213> ORGANISM: Artificial Sequence
<220> FEATURE:
<223> OTHER INFORMATION: AAV9-CAG-ohGALNS-version3

<400> SEQUENCE: 15

gctgcgcgct cgctcgctca ctgaggccgc ccgggcaaag cccgggcgtc gggcgacctt     60

tggtcgcccg gcctcagtga gcgagcgagc gcgcagagag ggagtggcca actccatcac    120

taggggttcc ttgtagttaa tgattaaccc gccatgctac ttatctactc gacattgatt    180

attgactagt tattaatagt aatcaattac ggggtcatta gttcatagcc catatatgga    240

gttccgcgtt acataactta cggtaaatgg cccgcctggc tgaccgccca acgacccccg    300

cccattgacg tcaataatga cgtatgttcc catagtaacg ccaataggga ctttccattg    360

acgtcaatgg gtggagtatt tacggtaaac tgcccacttg gcagtacatc aagtgtatca    420

tatgccaagt acgcccccta ttgacgtcaa tgacggtaaa tggcccgcct ggcattatgc    480

ccagtacatg accttatggg actttcctac ttggcagtac atctacgtat tagtcatcgc    540

tattaccatg gtcgaggtga gccccacgtt ctgcttcact ctccccatct cccccccctc    600

cccaccccca attttgtatt tatttatttt ttaattattt tgtgcagcga tgggggcggg    660

gggggggggg gggcgcgcgc caggcggggc ggggcggggc gaggggcggg gcggggcgag    720

gcggagaggt gcggcggcag ccaatcagag cggcgcgctc cgaaagtttc cttttatggc    780

gaggcggcgg cggcggcggc cctataaaaa gcgaagcgcg cggcgggcgg gagtcgctgc    840

gttgccttcg ccccgtgccc cgctccgccg ccgcctcgcg ccgcccgccc cggctctgac    900

tgaccgcgtt actcccacag gtgagcgggc gggacggccc ttctcctccg ggctgtaatt    960

agcgcttggt ttaatgacgg cttgtttctt ttctgtggct gcgtgaaagc cttgaggggc   1020

tccgggaggg ccctttgtgc ggggggagcg gctcgggggg tgcgtgcgtg tgtgtgtgcg   1080

tggggagcgc cgcgtgcggc tccgcgctgc ccggcggctg tgagcgctgc gggcgcggcg   1140

cggggctttg tgcgctccgc agtgtgcgcg aggggagcgc ggccgggggc ggtgccccgc   1200

ggtgcggggg gggctgcgag gggaacaaag gctgcgtgcg gggtgtgtgc gtgggggggt   1260

gagcaggggg tgtgggcgcg tcggtcgggc tgcaaccccc cctgcacccc cctccccgag   1320

ttgctgagca cggcccggct tcgggtgcgg ggctccgtac ggggcgtggc gcggggctcg   1380

ccgtgccggg cggggggtgg cggcaggtgg gggtgccggg cggggcgggg ccgcctcggg   1440

ccggggaggg ctcgggggag gggcgcggcg gcccccggag cgccggcggc tgtcgaggcg   1500

cggcgagccg cagccattgc cttttatggt aatcgtgcga gagggcgcag ggacttcctt   1560

tgtcccaaat ctgtgcggag ccgaaatctg ggaggcgccg ccgcaccccc tctagcgggc   1620

gcggggcgaa gcggtgcggc gccggcagga aggaaatggg cggggagggc cttcgtgcgt   1680

cgccgcgccg ccgtcccctt ctccctctcc agcctcgggg ctgtccgcgg ggggacggct   1740
```

-continued

```
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattgat taattcgagc gaacgcgtgc   1920
caccatggca gcggtggtgg ccgcgaccag atggtggcag cttctcctgg tcctgtcggc   1980
cgcgggaatg ggtgcctcgg gcgcgccgca gccccctaac attctgctgc tgctgatgga   2040
cgatatggga tggggcgacc tgggggtgta cggagagcct tcacgggaaa cccccaacct   2100
ggaccgcatg gcggctgaag gcctgctgtt cccgaacttt tactccgcga atccgctgtg   2160
ctccccttcg cgcgccgccc tcctgaccgg acggttgcct atccgcaacg gcttctacac   2220
tactaacgca cacgccagga acgcctacac cccgcaagaa attgtgggag gaatcccgga   2280
ttccgaacag ctgctgccgg aactgctgaa gaaggccggc tacgtgtcga agatcgtggg   2340
aaagtggcat cttggtcatc ggcctcagtt ccacccgctc aagcacgggt tcgatgaatg   2400
gttcggatcc cccaactgcc actttggccc ctacgacaac aaggctcggc ctaacattcc   2460
cgtctaccgg gactgggaaa tggtcggaag atactacgag gagttcccca tcaacctcaa   2520
gactggcgaa gccaacctga ctcagatcta cctccaagag gccctggact tcatcaagcg   2580
ccaggcccgg caccacccgt tcttcctcta ttgggcggtg gacgccaccc atgccccccgt   2640
gtacgcatca aagccgttcc ttggaactag ccagagaggc agatacgggg atgccgtgcg   2700
cgaaattgat gactccatcg gaaagatcct ggagctgctc caggacctcc atgtcgccga   2760
caataccttc gtgttcttta cttccgataa cggcgccgcc ttgatcagcg ccccggagca   2820
gggaggctcc aacggccctt ttctctgtgg gaaacagacc accttcgagg gagggatgcg   2880
ggaaccggct ctggcttggt ggcccggaca cgtgaccgcc ggccaagtgt cgcaccagct   2940
tggctccatc atggacttgt tcaccacctc actggccctc gcggggctca ccccaccaag   3000
cgaccgagcg attgacggtc tgaacttgct ccccactctg ctgcaaggaa ggctgatgga   3060
ccggcccatc ttctactatc ggggcgatac cttgatggcc gccaccctgg gacagcacaa   3120
ggcccacttt tggacttgga caaactcctg ggagaacttc cgccaaggga tcgacttctg   3180
ccccggtcaa aacgtgtccg gcgtgaccac ccacaacctg gaggaccata ccaagctgcc   3240
actgattttc caccttggtc gggacccagg agagagattc ccactgagct tcgcctccgc   3300
cgaatatcag gaagcactgt cccggatcac gagcgtggtg cagcagcatc aggaggccct   3360
ggtgccggcg cagccgcagc tcaatgtctg caactgggct gtgatgaact gggcaccccc   3420
tggctgcgaa aaactcggga agtgtctgac tccacctgag agcatcccga agaagtgcct   3480
gtggagccac taggaattcg agctcggtac ccgggaatca attcactcct caggtgcagg   3540
ctgcctatca gaaggtggtg gctggtgtgg ccaatgccct ggctcacaaa taccactgag   3600
atctttttcc ctctgccaaa aattatgggg acatcatgaa gccccttgag catctgactt   3660
ctggctaata aaggaaattt attttcattg caatagtgtg ttggaatttt ttgtgtctct   3720
cactcggaag gacatatggg agggcaaatc atttaaaaca tcagaatgag tatttggttt   3780
agagtttggc aacatatgcc catatgctgg ctgccatgaa caaaggttgg ctataaagag   3840
gtcatcagta tatgaaacag ccccctgctg tccattcctt attccataga aaagccttga   3900
cttgaggtta gatttttttt atattttgtt ttgtgttatt tttttcttta acatccctaa   3960
aattttcctt acatgtttta ctagccagat ttttcctcct ctcctgacta ctcccagtca   4020
tagctgtccc tcttctctta tggagatccc tcgacctgca gcccaagctg tagataagta   4080
gcatggcggg ttaatcatta actacaagga acccctagtg atggagttgg ccactccctc   4140
```

tctgcgcgct cgctcgctca ctgaggccgc ccgggctttg cccgggcggc ctcagtgagc 4200
gagcgagcgc gcagc 4215

<210> SEQ ID NO 16
<211> LENGTH: 4209
<212> TYPE: DNA
<213> ORGANISM: Artificial Sequence
<220> FEATURE:
<223> OTHER INFORMATION: AAV9-CAG-omGALNS/ AAV8-CAG-omGALNS

<400> SEQUENCE: 16
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagt tattaatagt aatcaattac ggggtcatta gttcatagcc catatatgga 240
gttccgcgtt acataactta cggtaaatgg cccgcctggc tgaccgccca acgacccccg 300
cccattgacg tcaataatga cgtatgttcc catagtaacg ccaataggga ctttccattg 360
acgtcaatgg gtggagtatt tacggtaaac tgcccacttg gcagtacatc aagtgtatca 420
tatgccaagt acgcccccta ttgacgtcaa tgacggtaaa tggcccgcct ggcattatgc 480
ccagtacatg accttatggg actttcctac ttggcagtac atctacgtat tagtcatcgc 540
tattaccatg gtcgaggtga gccccacgtt ctgcttcact ctccccatct cccccccctc 600
cccaccccca attttgtatt tatttatttt ttaattattt tgtgcagcga tgggggcggg 660
gggggggggg gggcgcgcgc caggcggggc ggggcggggc gaggggcggg gcggggcgag 720
gcggagaggt gcggcggcag ccaatcagag cggcgcgctc cgaaagtttc cttttatggc 780
gaggcggcgg cggcggcggc cctataaaaa gcgaagcgcg cggcgggcgg gagtcgctgc 840
gttgccttcg ccccgtgccc cgctccgccg ccgcctcgcg ccgcccgccc cggctctgac 900
tgaccgcgtt actcccacag gtgagcgggc gggacggccc ttctcctccg ggctgtaatt 960
agcgcttggt ttaatgacgg cttgtttctt ttctgtggct gcgtgaaagc cttgaggggc 1020
tccgggaggg ccctttgtgc ggggggagcg gctcgggggg tgcgtgcgtg tgtgtgtgcg 1080
tggggagcgc cgcgtgcggc tccgcgctgc ccggcggctg tgagcgctgc gggcgcggcg 1140
cggggctttg tgcgctccgc agtgtgcgcg aggggagcgc ggccgggggc ggtgccccgc 1200
ggtgcggggg gggctgcgag gggaacaaag gctgcgtgcg gggtgtgtgc gtgggggggt 1260
gagcaggggg tgtgggcgcg tcggtcgggc tgcaaccccc cctgcacccc cctccccgag 1320
ttgctgagca cggcccggct tcgggtgcgg ggctccgtac ggggcgtggc gcggggctcg 1380
ccgtgccggg cgggggggtgg cggcaggtgg gggtgccggg cggggcgggg ccgcctcggg 1440
ccggggaggg ctcgggggag ggcgcggcgg gcccccggag cgccggcggc tgtcgaggcg 1500
cggcgagccg cagccattgc cttttatggt aatcgtgcga gagggcgcag ggacttcctt 1560
tgtcccaaat ctgtgcggag ccgaaatctg ggaggcgccg ccgcaccccc tctagcgggc 1620
gcggggcgaa gcggtgcggc gccggcagga aggaaatggg cggggagggc cttcgtgcgt 1680
cgccgcgccg ccgtcccctt ctccctctcc agcctcgggg ctgtccgcgg ggggacggct 1740
gccttcgggg gggacggggc agggcggggt tcggcttctg gcgtgtgacc ggcggctcta 1800
gagcctctgc taaccatgtt catgccttct tctttttcct acagctcctg ggcaacgtgc 1860
tggttattgt gctgtctcat cattttggca aagaattgat taattcgagc gaacgcgtgc 1920

-continued caccatggct gcttgtacag ccgctcagca gctgctgctg gtgctgtctg ctctgggact 1980
gctggctgct ggcgctcctc agcctcctaa catcgtgctg ctgctgatgg acgacatggg 2040
ctggggcgat ctgggagtga acggcgagcc tagcagagag acacccaacc tggacagaat 2100
ggccgccgag ggcatgctgt tccccagctt ctacagcgcc aaccccctgt gcagcccttc 2160
tagagccgct ctgctgaccg gcagactgcc catcagaaac ggcttctaca ccaccaacgc 2220
ccacgccaga aacgcctaca caccccagga aatcatgggc ggcatcccca acagcgagca 2280
tctgctgcct gagctgctga agaaggccgg ctacaccaac aagatcgtgg gcaagtggca 2340
cctgggccac agaccccagt tccaccctct gaagcacggc ttcgacgagt ggttcggcag 2400
ccccaactgt cacttcggcc cctacgacaa caaggccaag cccaacatcc ccgtgtacag 2460
agactgggag atggtgggaa gattctacga agagttcccc atcaacagaa agaccggcga 2520
ggccaacctg acccagctgt acacacagga agccctggac ttcatccaga cccagcacgc 2580
cagacagagc cccttcttcc tgtactgggc catcgacgcc acacacgccc ctgtgtacgc 2640
cagcagacag ttcctgggca ccagcctgag aggcagatat ggcgacgccg tgcgcgagat 2700
cgacgactct gtgggcaaga tcctgtccct gctgcagaac ctgggcatca gcaagaacac 2760
cttcgtgttc ttcaccagcg acaacggcgc tgccctgatc agcgctccta atgagggcgg 2820
cagcaacggc ccattcctgt gcggcaagca gaccacattc gagggcggaa tgagagagcc 2880
cgctatcgct tggtggcctg gccatatcgc tgctggccag gtgtcacacc agctgggcag 2940
catcatggac ctgttcacca cctccctgag cctggccgga ctgaagcctc ctagcgacag 3000
agtgatcgac ggcctggacc tgctgcccac catgctgaag ggccagatga tggacagacc 3060
catcttctac tacagaggca acaccctgat ggccgtgacc ctgggccagt acaaggccca 3120
cctgtggacc tggaccaaca gctgggaaga gtttacccag ggcaccgatt tctgccctgg 3180
ccagaatgtg tccggcgtga ccacccacac ccaggaagaa cacaccgagc tgcccctgat 3240
cttccacctg ggaagggacc ccggcgagag attccctctg agcttccaca gcgacgagta 3300
ccaggacgcc ctgagcagaa ccacccaggt ggtgcaggaa caccagaaaa gcctggtgcc 3360
cggccagccc cagctgaacg tgtgtaacca ggccgtgatg aactgggccc ctcccggatg 3420
tgaaaagctg ggaaagtgcc tgaccccccc tgagagcgtg cccgagaagt gtttctgggc 3480
ccactgagaa ttcgagctcg gtacccggga atcaattcac tcctcaggtg caggctgcct 3540
atcagaaggt ggtggctggt gtggccaatg ccctggctca caaataccac tgagatcttt 3600
ttccctctgc caaaaattat ggggacatca tgaagcccct tgagcatctg acttctggct 3660
aataaaggaa atttattttc attgcaatag tgtgttggaa ttttttgtgt ctctcactcg 3720
gaaggacata tgggagggca aatcatttaa aacatcagaa tgagtatttg gtttagagtt 3780
tggcaacata tgcccatatg ctggctgcca tgaacaaagg ttggctataa agaggtcatc 3840
agtatatgaa acagccccct gctgtccatt ccttattcca tagaaaagcc ttgacttgag 3900
gttagatttt ttttatattt tgttttgtgt tatttttttc tttaacatcc ctaaaatttt 3960
ccttacatgt tttactagcc agatttttcc tcctctcctg actactccca gtcatagctg 4020
tccctcttct cttatggaga tccctcgacc tgcagcccaa gctgtagata agtagcatgg 4080
cgggttaatc attaactaca aggaacccct agtgatggag ttggccactc cctctctgcg 4140
cgctcgctcg ctcactgagg ccgcccgggc tttgcccggg cggcctcagt gagcgagcga 4200
gcgcgcagc 4209

<210> SEQ ID NO 17
<211> LENGTH: 3849
<212> TYPE: DNA
<213> ORGANISM: Artificial Sequence
<220> FEATURE:
<223> OTHER INFORMATION: AAV8-hAAT-omGALNS

<400> SEQUENCE: 17
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctactc gacattgatt 180
attgactagg atctgatatc atcgatgaat tcgagctcgg tacccggccg cagatttagg 240
tgacactata gaatatgcat cactagtaag cttgcgaatt ccagtctaca gagaggtctc 300
tgacctctgc cccagctcca aggtcagcag gcagggaggg ctgtgtgttt gctgtttgct 360
gcttgcaatg tttgcccatt ttagggacat gagtaggctg aagtttgttc agtgtggact 420
tcagaggcag cacacaaaca gcaagcttgc gaattccagt ctacagagag gtctctgacc 480
tctgccccag ctccaaggtc agcaggcagg gagggctgtg tgtttgctgt ttgctgcttg 540
caatgtttgc ccattttagg gacatgagta ggctgaagtt tgttcagtgt ggacttcaga 600
ggcagcacac aaacagcaag cttgcgaatt ccagtctaca gagaggtctc tgacctctgc 660
cccagctcca aggtcagcag gcagggaggg ctgtgtgttt gctgtttgct gcttgcaatg 720
tttgcccatt ttagggacat gagtaggctg aagtttgttc agtgtggact tcagaggcag 780
cacacaaaca gcaagctttg ctctagactg gaattcgtcg acgagctccc tatagtgagt 840
cgtattagag gccgactgac ccggtacccg gggatcttgc taccagtgga acagccacta 900
aggattctgc agtgagagca gagggccagc taagtggtac tctcccagag actgtctgac 960
tcacgccacc ccctccacct tggacacagg acgctgtggt ttctgagcca ggtacaatga 1020
ctcctttcgg taagtgcagt ggaagctgta cactgcccag gcaaagcgtc cgggcagcgt 1080
aggcgggcga ctcagatccc agccagtgga cttagcccct gtttgctcct ccgataactg 1140
gggtgacctt ggttaatatt caccagcagc ctcccccgtt gcccctctgg atccactgct 1200
taaatacgga cgaggacagg gccctgtctc ctcagcttca ggcaccacca ctgacctggg 1260
acagtgaatg tcccccctgat ctgcggccgt gactctctta aggtagcctt gcagaagttg 1320
gtcgtgaggc actgggcagg taagtatcaa ggttacaaga caggtttaag gagaccaata 1380
gaaactgggc ttgtcgagac agagaagact cttgcgtttc tgataggcac ctattggtct 1440
tactgacatc cactttgcct ttctctccac aggtgtccac tcccagttca attacagctc 1500
ttaaggctag agtacttaat acgactcact ataggctagc ctcgacctcg agacgcgtgc 1560
caccatggct gcttgtacag ccgctcagca gctgctgctg gtgctgtctg ctctgggact 1620
gctggctgct ggcgctcctc agcctcctaa catcgtgctg ctgctgatgg acgacatggg 1680
ctggggcgat ctgggagtga acggcgagcc tagcagagag acacccaacc tggacagaat 1740
ggccgccgag ggcatgctgt tccccagctt ctacagcgcc aaccccctgt gcagcccttc 1800
tagagccgct ctgctgaccg gcagactgcc catcagaaac ggcttctaca cccaccaacgc 1860 ccacgccaga aacgcctaca caccccagga aatcatgggc ggcatcccca acagcgagca 1920
tctgctgcct gagctgctga agaaggccgg ctacaccaac aagatcgtgg gcaagtggca 1980
cctgggccac agaccccagt tccaccctct gaagcacggc ttcgacgagt ggttcggcag 2040
ccccaactgt cacttcggcc cctacgacaa caaggccaag cccaacatcc ccgtgtacag 2100
agactgggag atggtgggaa gattctacga agagttcccc atcaacagaa agaccggcga 2160
ggccaacctg acccagctgt acacacagga agccctggac ttcatccaga cccagcacgc 2220
cagacagagc cccttcttcc tgtactgggc catcgacgcc acacacgccc ctgtgtacgc 2280
cagcagacag ttcctgggca ccagcctgag aggcagatat ggcgacgccg tgcgcgagat 2340
cgacgactct gtgggcaaga tcctgtccct gctgcagaac ctgggcatca gcaagaacac 2400
cttcgtgttc ttcaccagcg acaacggcgc tgccctgatc agcgctccta atgagggcgg 2460
cagcaacggc ccattcctgt gcggcaagca gaccacattc gagggcggaa tgagagagcc 2520
cgctatcgct tggtggcctg gccatatcgc tgctggccag gtgtcacacc agctgggcag 2580
catcatggac ctgttcacca cctccctgag cctggccgga ctgaagcctc ctagcgacag 2640
agtgatcgac ggcctggacc tgctgcccac catgctgaag ggccagatga tggacagacc 2700
catcttctac tacagaggca acaccctgat ggccgtgacc ctgggccagt acaaggccca 2760
cctgtggacc tggaccaaca gctgggaaga gtttacccag ggcaccgatt tctgccctgg 2820
ccagaatgtg tccggcgtga ccacccacac ccaggaagaa cacaccgagc tgcccctgat 2880
cttccacctg ggaagggacc ccggcgagag attccctctg agcttccaca gcgacgagta 2940
ccaggacgcc ctgagcagaa ccacccaggt ggtgcaggaa caccagaaaa gcctggtgcc 3000
cggccagccc cagctgaacg tgtgtaacca ggccgtgatg aactgggccc ctcccggatg 3060
tgaaaagctg ggaaagtgcc tgaccccccc tgagagcgtg cccgagaagt gtttctgggc 3120
ccactgagaa ttcgagctcg gtacccggga atcaattcac tcctcaggtg caggctgcct 3180
atcagaaggt ggtggctggt gtggccaatg ccctggctca caaataccac tgagatcttt 3240
ttccctctgc caaaaattat ggggacatca tgaagcccct tgagcatctg acttctggct 3300
aataaaggaa atttattttc attgcaatag tgtgttggaa ttttttgtgt ctctcactcg 3360
gaaggacata tgggagggca aatcatttaa aacatcagaa tgagtatttg gtttagagtt 3420
tggcaacata tgcccatatg ctggctgcca tgaacaaagg ttggctataa agaggtcatc 3480
agtatatgaa acagccccct gctgtccatt ccttattcca tagaaaagcc ttgacttgag 3540
gttagatttt ttttatattt tgttttgtgt tatttttttc tttaacatcc ctaaaatttt 3600
ccttacatgt tttactagcc agatttttcc tcctctcctg actactccca gtcatagctg 3660
tccctcttct cttatggaga tccctcgacc tgcagcccaa gctgtagata agtagcatgg 3720
cgggttaatc attaactaca aggaacccct agtgatggag ttggccactc cctctctgcg 3780
cgctcgctcg ctcactgagg ccgcccgggc tttgcccggg cggcctcagt gagcgagcga 3840
gcgcgcagc 3849

<210> SEQ ID NO 18
<211> LENGTH: 1674
<212> TYPE: DNA
<213> ORGANISM: Artificial Sequence
<220> FEATURE:
<223> OTHER INFORMATION: CAG Promoter

<400> SEQUENCE: 18
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtcgaggtga gccccacgtt ctgcttcact ctccccatct 420
cccccccctc cccaccccca attttgtatt tatttatttt ttaattattt tgtgcagcga 480
tgggggcggg gggggggggg gggcgcgcgc caggcggggc ggggcggggc gaggggcggg 540
gcggggcgag gcggagaggt gcggcggcag ccaatcagag cggcgcgctc cgaaagtttc 600 ccttttatggc gaggcggcgg cggcggcggc cctataaaaa gcgaagcgcg cggcgggcgg 660
gagtcgctgc gttgccttcg ccccgtgccc cgctccgccg ccgcctcgcg ccgcccgccc 720
cggctctgac tgaccgcgtt actcccacag gtgagcgggc gggacggccc ttctcctccg 780
ggctgtaatt agcgcttggt ttaatgacgg cttgtttctt ttctgtggct gcgtgaaagc 840
cttgaggggc tccgggaggg ccctttgtgc ggggggagcg gctcgggggg tgcgtgcgtg 900
tgtgtgtgcg tggggagcgc cgcgtgcggc tccgcgctgc ccggcggctg tgagcgctgc 960
gggcgcggcg cggggctttg tgcgctccgc agtgtgcgcg aggggagcgc ggccgggggc 1020
ggtgccccgc ggtgcggggg gggctgcgag gggaacaaag gctgcgtgcg gggtgtgtgc 1080
gtgggggggt gagcaggggg tgtgggcgcg tcggtcgggc tgcaaccccc cctgcacccc 1140
cctccccgag ttgctgagca cggcccggct tcgggtgcgg ggctccgtac ggggcgtggc 1200
gcggggctcg ccgtgccggg cgggggggtgg cggcaggtgg gggtgccggg cggggcgggg 1260
ccgcctcggg ccggggaggg ctcgggggag gggcgcggcg gcccccggag cgccggcggc 1320
tgtcgaggcg cggcgagccg cagccattgc cttttatggt aatcgtgcga gagggcgcag 1380
ggacttcctt tgtcccaaat ctgtgcggag ccgaaatctg ggaggcgccg ccgcaccccc 1440
tctagcgggc gcggggcgaa gcggtgcggc gccggcagga aggaaatggg cggggagggc 1500
cttcgtgcgt cgccgcgccg ccgtcccctt ctccctctcc agcctcgggg ctgtccgcgg 1560
ggggacggct gccttcgggg gggacggggc agggcggggt tcggcttctg gcgtgtgacc 1620
ggcggctcta gagcctctgc taaccatgtt catgccttct tctttttcct acag 1674

<210> SEQ ID NO 19
<211> LENGTH: 1221
<212> TYPE: DNA
<213> ORGANISM: Artificial Sequence
<220> FEATURE:
<223> OTHER INFORMATION: hAAT Promoter

<400> SEQUENCE: 19
gatctgatat catcgatgaa ttcgagctcg gtacccggcc gcagatttag gtgacactat 60
agaatatgca tcactagtaa gcttgcgaat tccagtctac agagaggtct ctgacctctg 120
ccccagctcc aaggtcagca ggcagggagg gctgtgtgtt tgctgtttgc tgcttgcaat 180
gtttgcccat tttagggaca tgagtaggct gaagtttgtt cagtgtggac ttcagaggca 240
gcacacaaac agcaagcttg cgaattccag tctacagaga ggtctctgac ctctgcccca 300
gctccaaggt cagcaggcag ggagggctgt gtgtttgctg tttgctgctt gcaatgtttg 360
cccattttag ggacatgagt aggctgaagt ttgttcagtg tggacttcag aggcagcaca 420
caaacagcaa gcttgcgaat tccagtctac agagaggtct ctgacctctg ccccagctcc 480
aaggtcagca ggcagggagg gctgtgtgtt tgctgtttgc tgcttgcaat gtttgcccat 540
tttagggaca tgagtaggct gaagtttgtt cagtgtggac ttcagaggca gcacacaaac 600
agcaagcttt gctctagact ggaattcgtc gacgagctcc ctatagtgag tcgtattaga 660

-continued

```
ggccgactga cccggtaccc ggggatcttg ctaccagtgg aacagccact aaggattctg    720

cagtgagagc agagggccag ctaagtggta ctctcccaga gactgtctga ctcacgccac    780

cccctccacc ttggacacag gacgctgtgg tttctgagcc aggtacaatg actcctttcg    840

gtaagtgcag tggaagctgt acactgccca ggcaaagcgt ccgggcagcg taggcgggcg    900

actcagatcc cagccagtgg acttagcccc tgtttgctcc tccgataact ggggtgacct    960

tggttaatat tcaccagcag cctcccccgt tgcccctctg gatccactgc ttaaatacgg   1020

acgaggacag ggccctgtct cctcagcttc aggcaccacc actgacctgg gacagtgaat   1080

gtccccctga tctgcggccg tgactctctt aaggtagcct tgcagaagtt ggtcgtgagg   1140

cactgggcag gtaagtatca aggttacaag acaggtttaa ggagaccaat agaaactggg   1200

cttgtcgaga cagagaagac t                                             1221


<210> SEQ ID NO 20
<211> LENGTH: 22
<212> TYPE: DNA
<213> ORGANISM: Artificial Sequence
<220> FEATURE:
<223> OTHER INFORMATION: Sense primer

<400> SEQUENCE: 20

ccagggaatg tcccacctat tt                                              22


<210> SEQ ID NO 21
<211> LENGTH: 20
<212> TYPE: DNA
<213> ORGANISM: Artificial Sequence
<220> FEATURE:
<223> OTHER INFORMATION: Antisense primer

<400> SEQUENCE: 21

gtcaggttga cacgaagctg                                                 20


<210> SEQ ID NO 22
<211> LENGTH: 18
<212> TYPE: DNA
<213> ORGANISM: Artificial Sequence
<220> FEATURE:
<223> OTHER INFORMATION: Antisense primer KO

<400> SEQUENCE: 22

ggaacttcgg ttccggcg                                                   18
```

ADENOASSOCIATED VIRUS VECTORS FOR THE TREATMENT OF MUCOPOLYSACCHARIDOSES TYPE IV A

Incorporated by reference in its entirety herein is a computer-readable nucleotide/amino acid sequence listing submitted concurrently herewith and identified as follows: One 114,688 Bytes ASCII (Text) file named "SEQUENCE_LISTING.TXT," created on 25 Nov. 2020.

FIELD OF THE INVENTION

The present invention relates to polynucleotide sequences and vectors useful for the expression of proteins of interest and their utilization in gene therapy. The present invention also relates to vectors and nucleic acid sequences helpful for the treatment of mucopolysaccharidoses (MPS). and in particular, for the treatment of mucopolysaccharidoses type IVA or Morquio A syndrome.

BACKGROUND OF THE INVENTION

The lysosome is an organelle found in the cytoplasm of animal cells that contains more than 50 hydrolases that break down biomolecules during the recycling of worn-out cellular components or after the engulfment of viruses and bacteria. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. However, some groups within the general population are particularly afflicted by a high occurrence of LSDs. For instance, the prevalence of Gaucher and Tay-Sachs diseases in descendants from Jewish Central and Eastern European (Ashkenazi) individuals is 1 per 600 and 1 per 3,900 births, respectively.

The mucopolysaccharidoses (MPS) are a group of seven LSD diseases characterized by the absence or deficiency of a specific lysosomal enzyme involved in the metabolism of Glucosaminoglycans (GAGs). All MPS have an autosomal recessive pattern of Inheritance, with the exception for MPSII (Hunter disease) that has an X chromosomal linked inheritance.

Of the seven MPS, mucopolysaccharidosis type IV (MPSIV or Morquio syndrome) has two sub-types, A and B. Morquio A and B are both autosomal recessive inherited conditions, which affect males and females equally. Morquio A or MPSIVA is a rare condition and existing data on prevalence are scarce and variable. Reported estimates range from 1 per 76,320 in Northern Ireland to 1 per 641,178 in Western Australia. MPSIVA is caused by the deficiency of one of the enzymes involved in the degradation of the GAG Keratan sulfate (KS) and Chondroitin 6-sulfate (C6S). The gene coding this enzyme has been identified and various mutations have been reported.

MPSIVA is caused by the deficiency in the activity of the enzyme galactosamine (N-acetyl)-6-sulfatase (GALNS, EC 3.1.6.4). GALNS is a lysosomal enzyme which hydrolysis the sulfate ester group of N-acetylgalactosamine-6-sulfate at the nonreducing end of chondroitin-6-sulfate (C6S) and that of galactose-6-sulfate at the nonreducing end of keratan sulfate (KS). As a consequence of the sustained accumulation of non-degraded C6S and KS progressive cellular damage occurs, resulting in multisystemic disease. Presently, about 180 different mutations have been identified in the human GALNS gene leading to the deficiency of the activity of the GALNS enzyme.

The majority of KS and C6S are produced by chondrocytes, and therefore, the undegraded substrates accumulate mainly in cells and extracellular matrix of cartilage. This has a direct impact on cartilage and bone development, leading to systemic skeletal dysplasia. In patients with Morquio A, cartilage cells are vacuolated, and this results in abnormal chondrogenesis and/or endochondral ossification. Most of the patients with MPSIVA are born apparently healthy and the symptoms develop progressively. Initial symptoms are recognized between 1 and 3 years of age and mean age at diagnosis is around 4.7 years. The main skeletal features include: striking shot trunk dwarfism, odontoid hypoplasia, pectus carinatum, kyphosis, scoliosis, genu valgum, coxa valga, flaring of the lower ribs, hypermobile joints and abnormal gait with a tendency to fall. Other potential complications include pulmonary compromise, valvular heart disease, hearing loss, hepatomegaly, fine corneal clouding, coarse facial features and widely spaced teeth with abnormally thin enamel and frequent caries. MPSIVA patients preserve intelligence. The rate of disease progression and the phenotypic features present are variable between patients. MPSIVA phenotypes are defined as severe if final height is below 120 cm, as intermediate if final height is above 120 cm and below 140 cm, and as mild if ultimate height is above 140 cm throughout ages. Reported life expectancies ranging from second decade of life to 70 years of age. This variability may be related to multiple factors, such as the nature of the mutation, ethnicity or differences in the health care that the patient receives.

Until recently, there were no disease-specific approved therapies for MPSIVA syndrome. The available treatments were symptomatic and based on the administration of a wide range of unspecific drugs for the prevention and management of disease complications. However, two main therapeutic options have become available for MPSIVA patients in the last few years: enzyme replacement therapy (ERT) and hematopoietic stem cell transplantation (HSCT). The design of both therapeutic strategies relies on the possibility of cross-correction, based on the fact that normal cells secrete significant amounts of mannose-6-phosphate (M6P)-tagged soluble lysosomal enzymes, such as GALNS, which can be subsequently taken up from the extracellular compartment by other cells via M6P receptors on the plasma membrane and targeted to the lysosomes. In addition, there is a threshold of residual enzymatic activity, generally very low, above which the cell is capable of coping with substrate influx and the disease does not affect subjects, suggesting that restoration of normal activity is not a requisite to modify the clinical course.

For MPSIVA, ERT has been tested in two different murine mouse models of the disease (Tomatsu et al., 2008, 2010a, 2015). In this study, a dose of 250 U/g of recombinant murine GALNS (rGALNS) was weekly administered intravenously or intraperitoneally to MPSIVA mouse of 0.5 and 12 weeks of age. One week after the last dosage, MPSIVA mice showed marked reduction of GAG storage in visceral organs, sinus lining cells in bone marrow, heart valves, ligaments and connective tissues and marked reduction of blood KS levels, evidencing somatic correction by the infusion of rGALNS.

In 2014, recombinant human GALNS commercialized as Elosulfase alfa, VIMIZIM® (BioMarin Pharmaceutical Inc) was approved by the Food and Drug Administration (FDA) and European Medicines Agency (EMA) for the treatment of MPSIVA. The treatment was administered weekly at a dose of 2 mg/kg by intravenous infusion, with an average infusion period of time of 3.5-4.5 hours. The age of enrolled patients ranged from 5 to 57 years. At baseline, all enrolled patients could walk between 30 and 325 m in the 6 minute walking test (6MWT) (Sanford and Lo. 2014). The primary endpoint was established as the change from baseline in the distance walked in 6MWT at week 24 post-treatment initiation. Secondary endpoints included changes from baseline in the rate of stair climbing in three minutes (3MSCT) and in urine KS levels at week 24. Patients were divided in two treatment groups: those who received VIMIZIM® at a weekly dose of 2 mg/kg and those with 2 mg/kg once every other week. In patients who received VIMIZIM 2 mg/kg weekly, the distance walked in 6MWT was increased up to 22,5 m compared to placebo cohort 24 weeks post-treatment initiation. However, there was no difference in the rate of stair climbing in patients who received VIMIZIM®. Moreover, no further improvement was observed in walking ability with respect to the first 24 weeks of treatment. On the other hand, there were no differences in 6MWT and 3MSCT in patients who received VIMIZIM® 2 mg/kg once every other week, compared to placebo group. The reduction in urinary KS levels from baseline, a measure of pharmacodynamics effect, was greater in all the VIMIZIM® treatment groups (2014). Patients who initially were included in the placebo-controlled trial were afterwards eligible to start treatment with VIMIZIN® in an open-label extension trial (MOR-005).

Due to a possible hypersensitivity to VIMIZIM®, medical support is available during product administration. During the trial, the most severe adverse events described have been anaphylactic and hypersensitivity reactions, that can appear anytime during VIMIZIM® infusion or up to 3 hours after product administration, Patients with acute respiratory illness may be at increased risk and require additional monitoring. These anaphylactic reactions, that can compromise the patient's life, include cough, rash, throat tightness, hives, flushing, changes in skin color, low blood pressure, shortness of breath, chest pain, and gastrointestinal symptoms such as nausea, abdominal pain, retching, and vomiting (http://vimizim.com). Other disadvantages of ERT include: 1) the difficulty of performing 3.5-4.5 hour-long intravenous infusions in pediatric patients, 2) the fact that 100% of patients treated with VIMIZIM® 2 mg/kg once per week developed anti-drug antibodies after 4 weeks, 3) all patients tested developed neutralizing antibodies capable of inhibiting the drug from binding to the mannose-6-phosphate receptor at least once during the trial, and 4) the high cost of the therapy, which includes also the costs of home-care (2014).

Hematopoietic stem cell transplantation (HSCT) using bone marrow-derived stem cells (Bone marrow transplantation, BMT) has proven efficient in the treatment of both somatic and neurological pathology in patients with other MPSs. The main drawback on the phenotype correction by HSCT is the minimal impact that treatment has on the growth of MPSIVA patients (Chinen et al., 2014; Wang et al., 2016; Yabe et al., 2016).

Given the limitations of current therapeutic options for MPSIVA, alternative approaches are needed.

In vivo gene therapy offers the possibility of a one-time treatment for MPSIVA and other inherited diseases, with the prospect of lifelong beneficial effects.

Gene therapy preclinical studies for Morquio A disease have been mainly based on the administration of γ-retrovirus-, lentivirus-, and Adeno-associated-derived vectors.

The in vitro transduction of MPSIVA human lymphoblastoid B cells, human keratinocytes, murine myoblasts, and rabbit synoviocytes with γ-retrovirus-derived vectors encoding for human GALNS gene resulted in an increase in GALNS enzymatic activity that lead to a reduction of intracellular GAG storage (Toietta et al., 2001).

The administration of lentiviral-derived vectors coding for human GALNS cDNA to Morquio A skin fibroblasts showed enzyme activity levels 7.5-fold higher than those of non-transduced MPSIVA fibroblasts, although lower than those of human healthy fibroblasts. The use of lentiviral vectors also led to the normalization of β-hexosaminidase and β-galactosidase activities, which have been reported to be secondary biomarkers for Morquio A (Almeciga et al., 2013; Salazar et al., 2016).

Adeno-associated virus (AAV) vector-mediated gene transfer, in particular, is rapidly emerging as the approach of choice for many in vivo gene therapy applications, due to the high transduction efficiency and the lack of pathogenicity of these vectors. AAV vectors can transduce post-mitotic cells and several pre-clinical and clinical studies have demonstrated the potential of AAV vector-mediated gene transfer to efficiently drive sustained expression of therapeutic transgenes for a variety of diseases.

The use of AAV vectors allowed the evaluation of the effect of co-expression of GALNS and Sulfatase Modifying Factor 1 (SUMF1) on enzyme activity. This co-expression resulted in up to 4-fold increase in enzyme activity in cell cultures (Alméciga-Díaz et al., 2010). In vivo, administration of AAV-GALNS vectors in a Morquio A mouse model showed that the enzyme activity in plasma was restored up to 8.5% of wild-type levels 12 weeks after a single intravenous administration, while co-administration with AAV-SUMF1 vector resulted in an increase of GALNS activity up to 19% of wild-type levels. GALNS enzyme activity was also increased up to 30% and 33% of wild-type in heart and bone, respectively (Alméciga Javier, Montaño Adriana, Shunji Tomatsu, 2012).

To improve the bone delivery of GALNS enzyme, a modified AAV vector carrying a short acidic amino acid peptide within the viral capsid to confer affinity of the virus for bone hydroxyapatite was developed. This modified GALNS-encoding AAV vector significantly increased vector genome copies and transgene expression in bone of MPSIVA mouse model and led to GALNS activity levels of 42% of wild-type (Alméciga Javier, Montaño Adriana, Shunji Tomatsu, 2012; Tomatsu et al., 2010b).

None of aforementioned approaches has fully restored galactosamine (N-acetyl)-6-sulfatase activity, achieved full eradication of intracytoplasmic inclusions, or corrected all clinical signs of MPSIVA. Thus, there is a need for novel approaches to the treatment of MPSIVA that have better efficacy and safety profiles.

SUMMARY OF THE INVENTION

The present invention provides new polynucleotide sequences and vectors for the treatment of mucopolysaccharidoses, in particular mucopolysaccharidoses type IVA or Morquio A syndrome.

In a first aspect, the present invention provides a new isolated polynucleotide sequence having 75% to 90% identity with the nucleotide sequence as set for in SEQ ID NO: 1 wherein said sequence encodes a functional human galactosamine (N-acetyl)-6-sulfatase.

In another aspect, the invention refers to an expression vector comprising the polynucleotide sequence of the invention.

A further aspect of the present invention relates to a pharmaceutical composition comprising a therapeutically effective amount of the polynucleotide sequences or the vector of the invention.

Still, a further aspect of the invention relates to a polynucleotide sequence or a vector, or a pharmaceutical composition described herein for use as a medicament, in particular for the treatment of mucopolysaccharidoses type IVA or Morquio A syndrome.

The present invention also provides a method for the production of the adeno-associated viral vector according to the invention.

(B) Schematic representation of the genome of an Adeno-associated vector containing the omGalns coding sequence.

Figure 7:
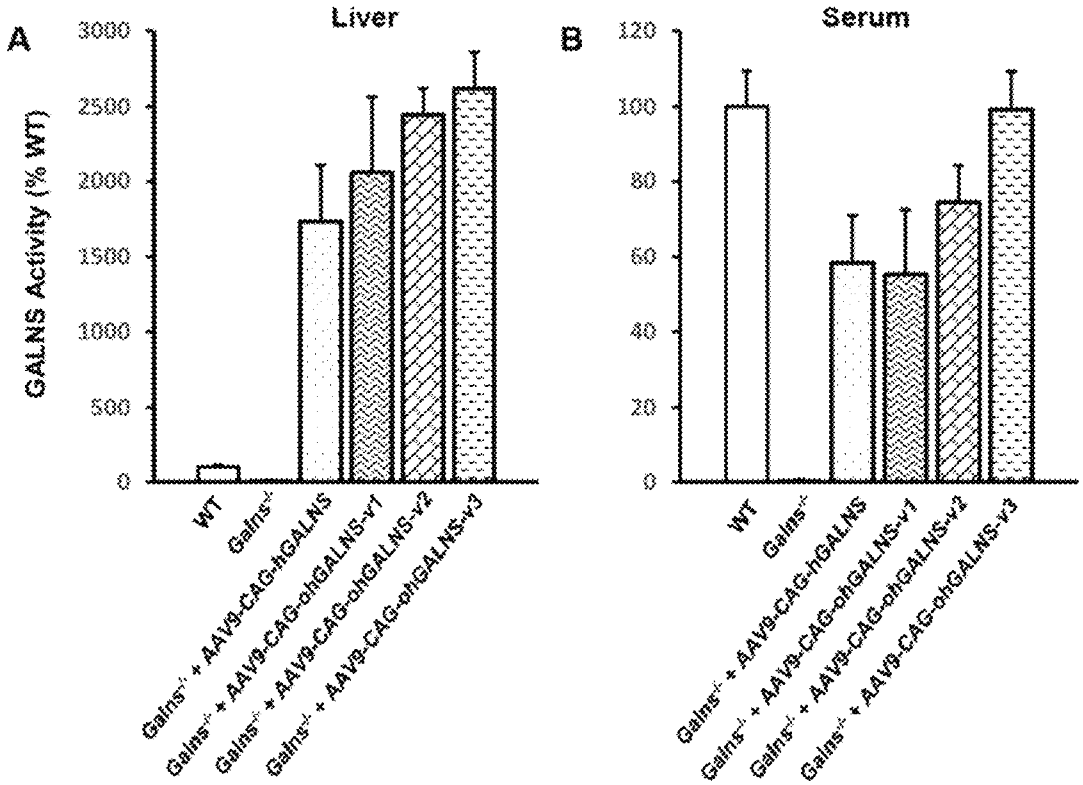

FIG. 7. Intravenous delivery of AAV9 vectors coding for different human Galns versions (AAV9-CAG-hGalns, AAV9-CAG-ohGalns-v1, AAV9-CAG-ohGalns-v2, and AAV9-CAG-ohGalns-v3) to male mice. GALNS activity in (A) liver and (B) serum of wild-type (healthy) mice (WT), untreated Galns−/− mice and Galns−/− mice administered systemically, via intravenous (IV) injection, with $5\times10^{10}$ vg of each vector at 2 month of age. WT GALNS activity was set to 100%. Values are means±SEM of 4-5 mice per group.

Figure 8:
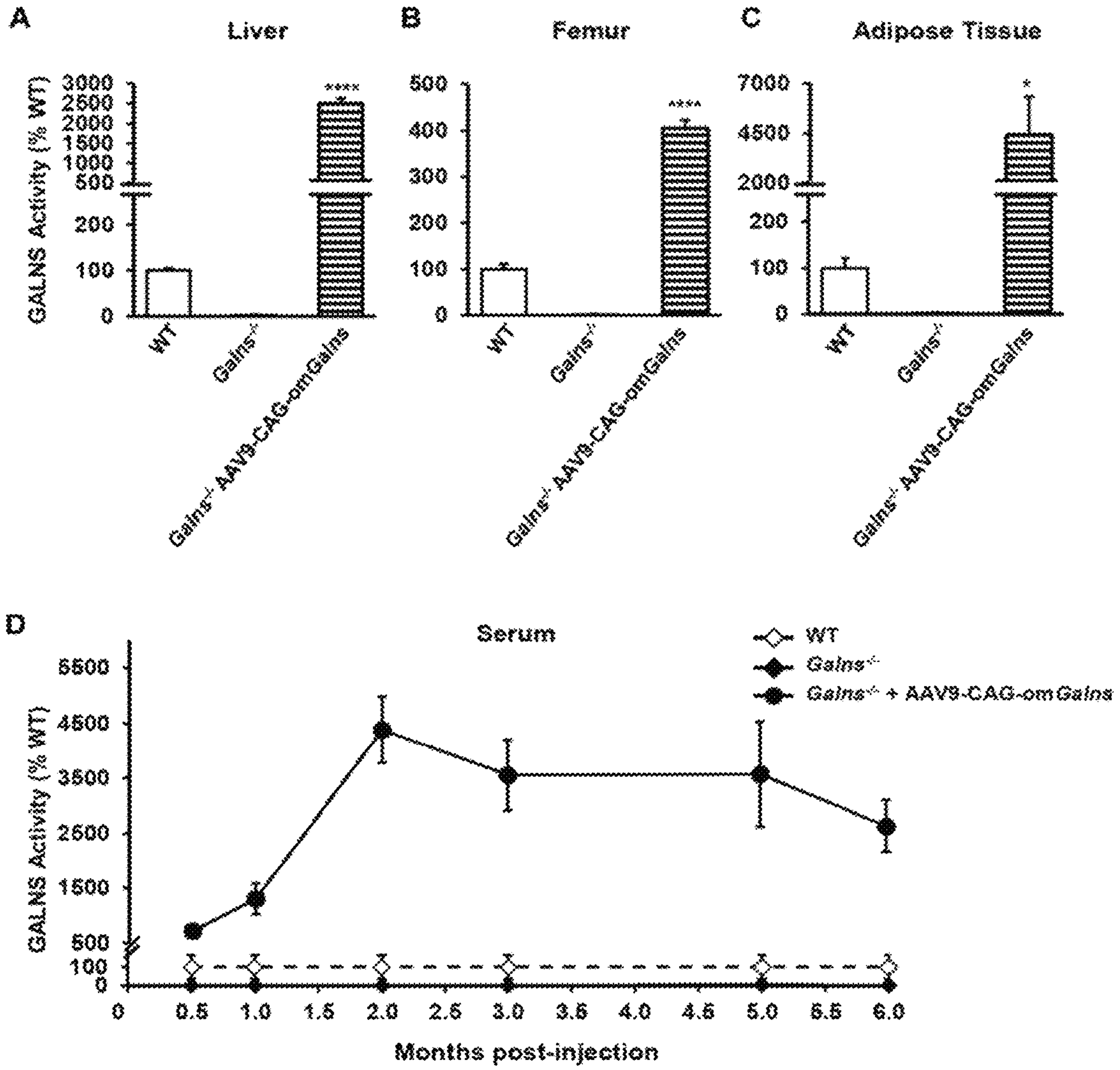

FIG. 8. Intravenous delivery of AAV9 vector coding for optimized murine Galns (AAV9-CAG-omGalns) to male mice. GALNS activity in (A) liver, (B) femur, (C) adipose tissue of wild-type (healthy) mice (WT), untreated Gains−/− mice and Galns−/− mice administered systemically, via intravenous (IV) injection, with $1\times10^{12}$ vg of AAV9-CAGo-mGalns at 1 month of age. (D) GALNS activity in the serum at different post-injection points in the same cohort of animals. WT GALNS activity was set to 100%. Values are means±SEM of 4-5 mice per group. * P<0.05, ** P<0.0001, vs. Galns−/− untreated mice.

Figure 9:
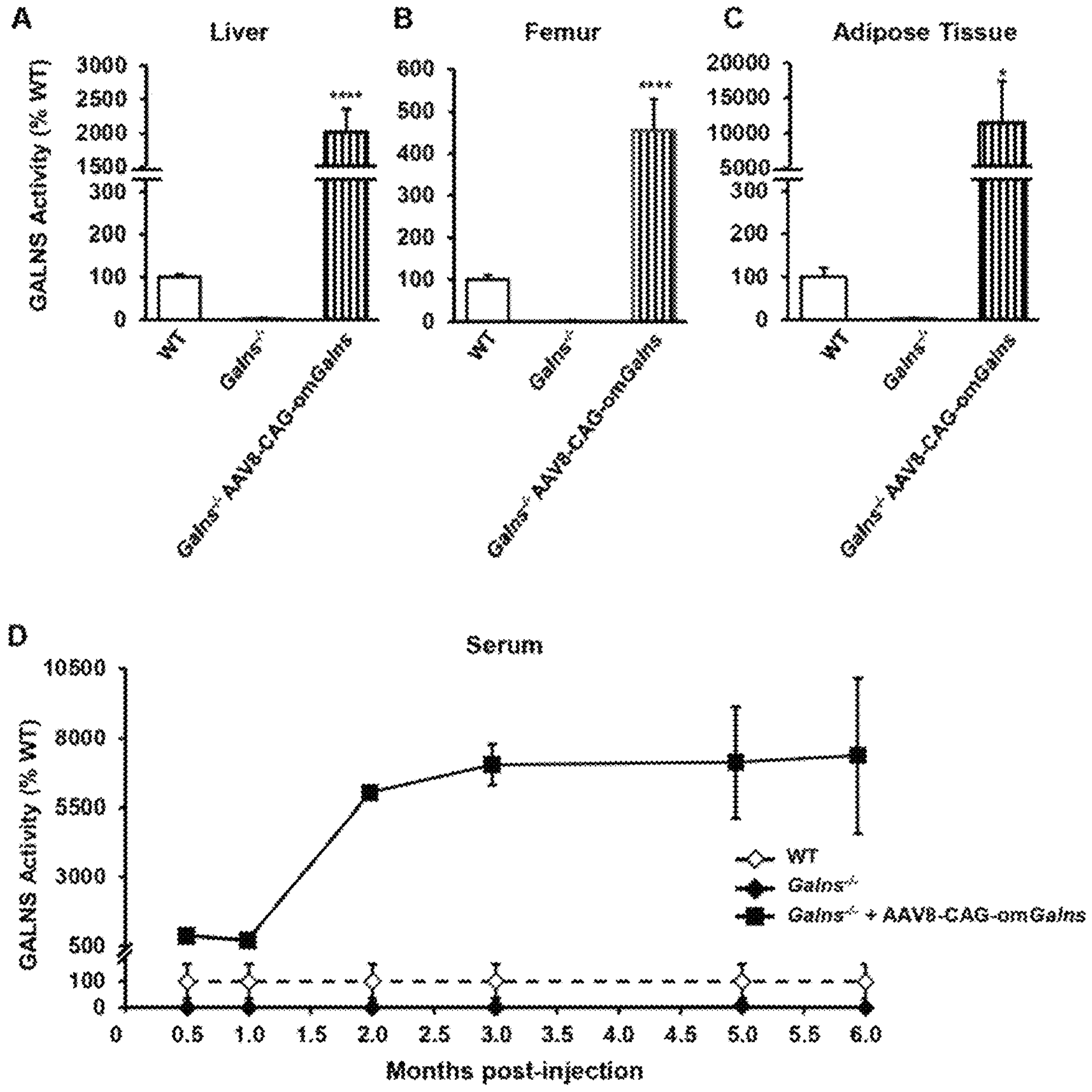

FIG. 9. Intravenous delivery of AAV8 vector coding for optimized murine Galns (AAV8-CAG-omGalns) to male mice. GALNS activity in (A) liver. (B) femur. (C) adipose tissue of wild-type (healthy) mice (WT), untreated Galns−/− mice and Galns−/− mice administered systemically, via intravenous (IV) injection, with $1\times10^{12}$ vg of AAV8-CAGo-mGalns at 1 month of age. (D) GALNS activity in the serum at different post-injection points in the same cohort of animals. WT GALNS activity was set to 100%. Values are means±SEM of 4-5 mice per group. * P<0.05. * P<0.0001, vs. Galns−/− untreated mice.

Figure 10:
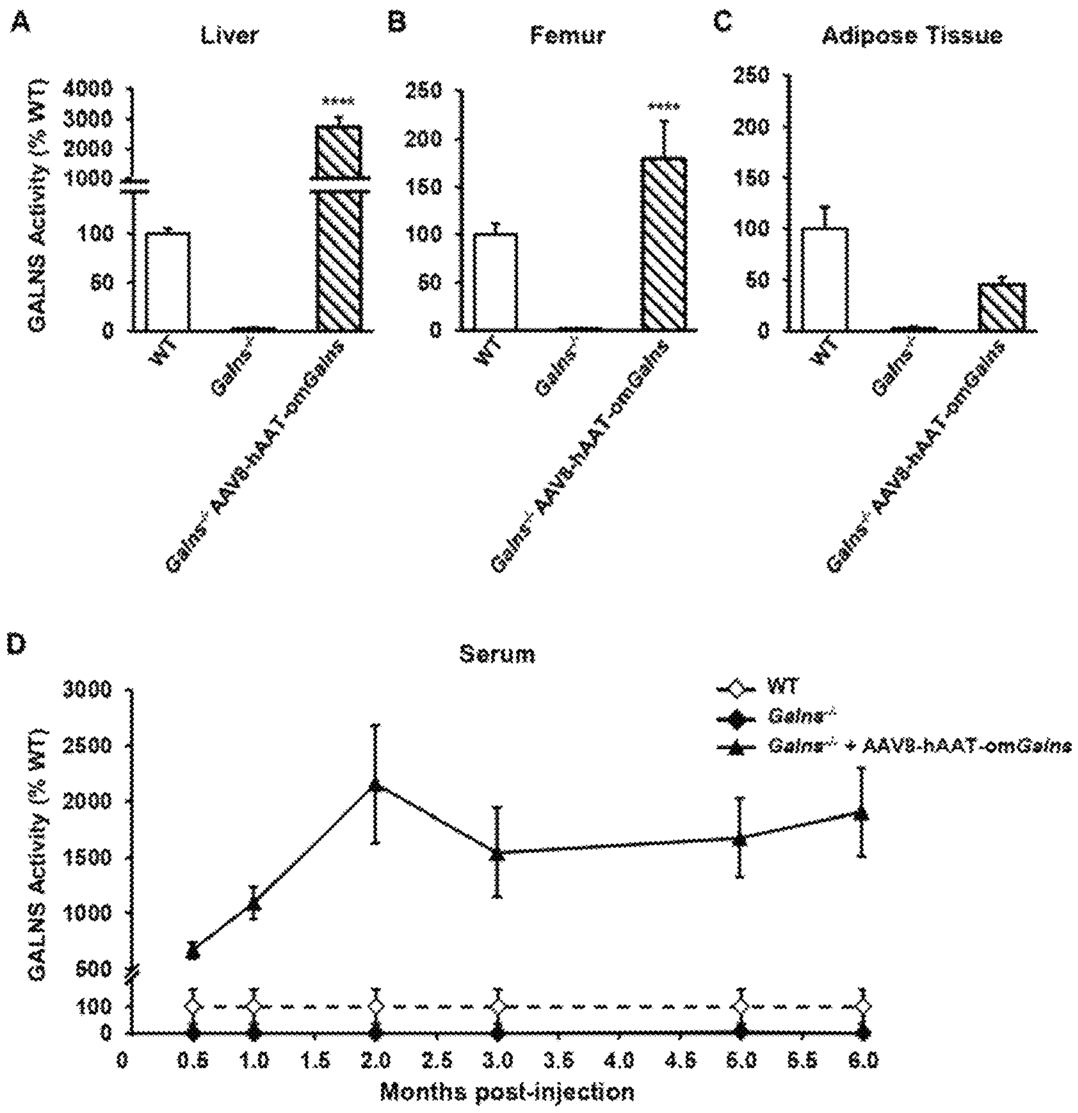

FIG. 10. Intravenous delivery of AAV8 vector coding for optimized murine Galns (AAV8-hAAT-omGalns) to male mice. GALNS activity in (A) liver, (B) femur, (C) adipose tissue of wild-type (healthy) mice (WT), untreated Galns−/− mice and Galns−/− mice administered systemically, via intravenous (IV) injection, with $1\times10^{11}$ vg of AAV8-hAAT-omGalns at 1 month of age. (D) GALNS activity in the serum at different postinjection points in the same cohort of animals. WT GALNS activity was set to 100%. Values are means±SEM of 4-5 mice per group. * P<0.05, **** P<0.0001, vs. Galns−/− untreated mice.

Figure 11:
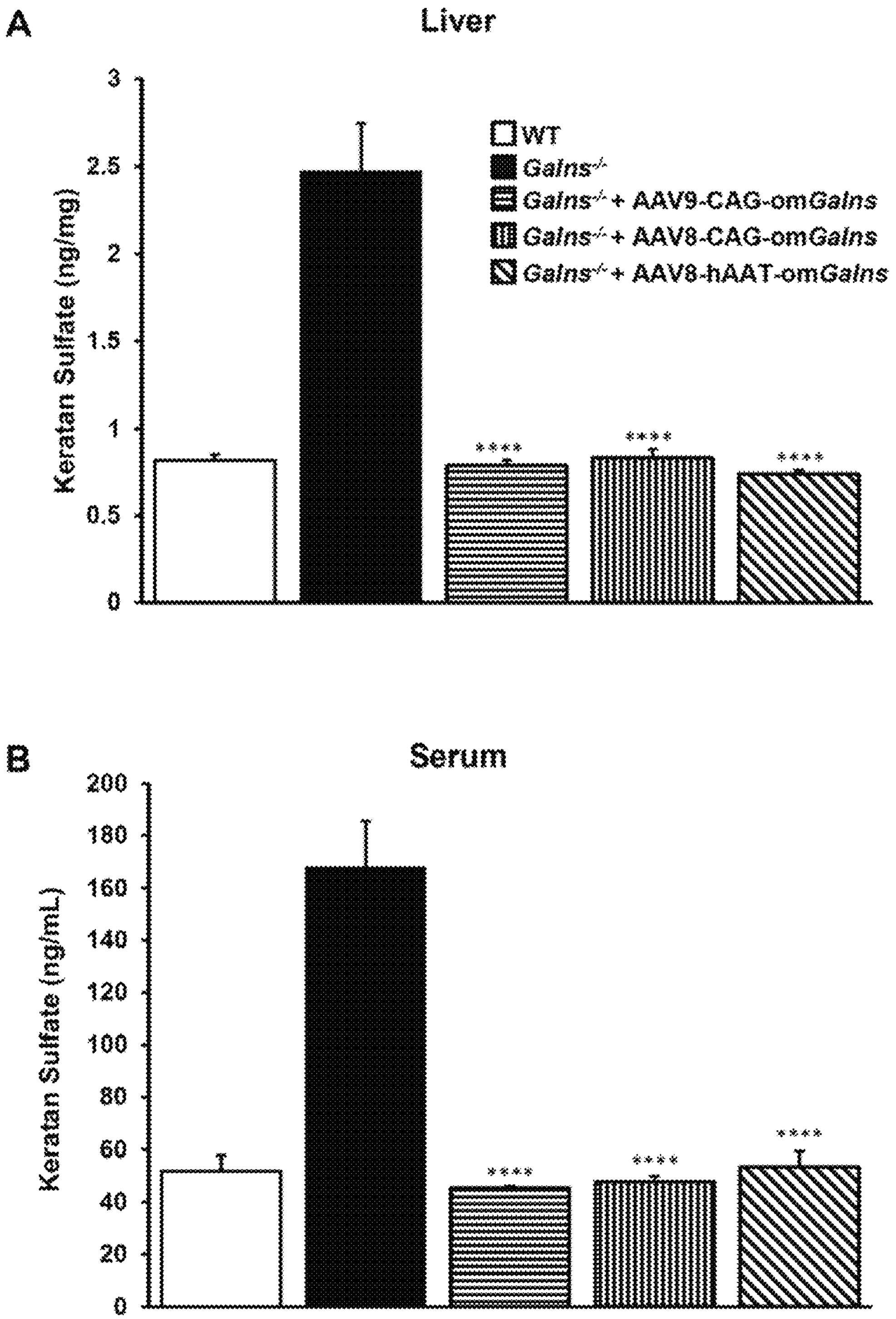
Figure 12:
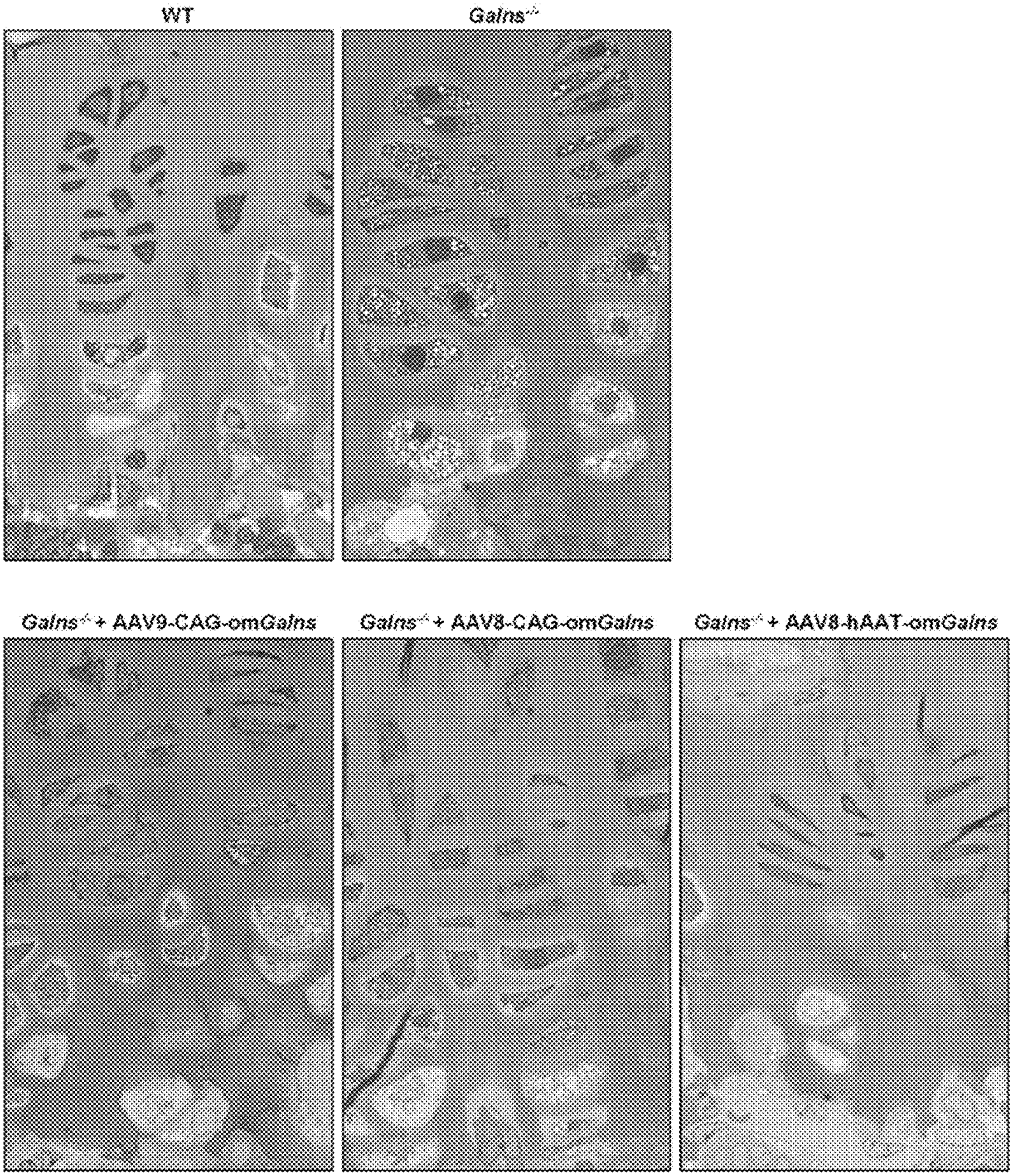

FIG. 11. Intravenous delivery of AAV9 and AAV8 vectors coding for optimized murine Galns (AAV9-CAG-omGalns. AAV8-CAG-omGalns and AAV8-hAATomGalns) to male mice. Quantification of keratan sulfate (KS) in (A) liver and (B) serum by LC-MS/MS analysis. ** P<0.0001, vs. Galns−/− male untreated mice FIG. 12**. Intravenous delivery of AAV9 and AAV8 vectors coding for optimized murine Galns (AAV9-CAG-omGalns. AAV8-CAG-omGalns and AAV8-hAATomGalns) to male mice. Histopathology of tibial epiphyseal growth plate in sections stained with toluidine blue. Original magnification 100×.

Figure 13:
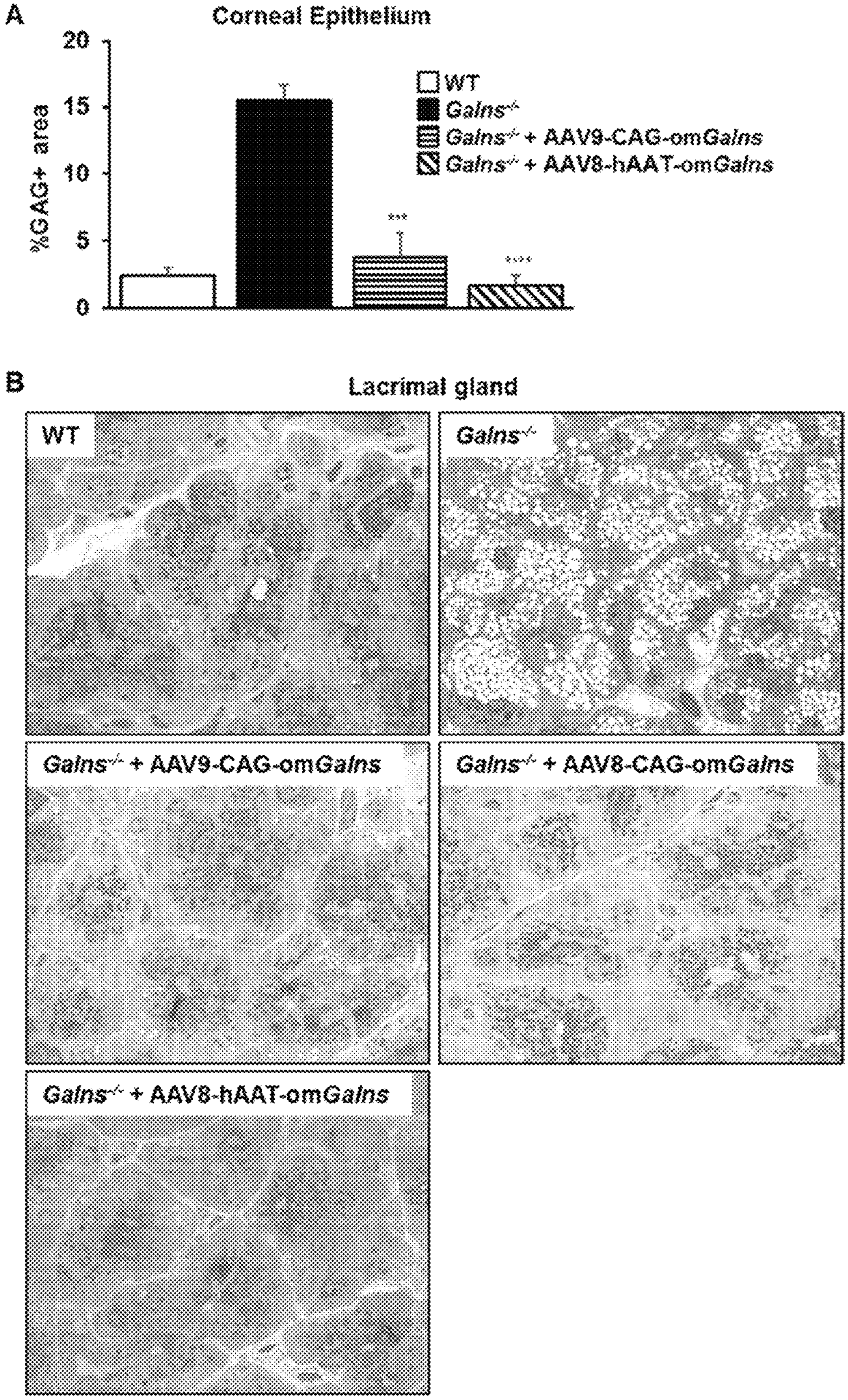

FIG. 13. Intravenous delivery of AAV9 and AAV8 vectors coding for optimized murine Galns (AAV9-CAG-omGalns. AAV8-CAG-omGalns and AAV8-hAATomGalns) to male Galns−/− mice. (A) Quantification of the staining intensity obtained in corneal epithelium following Mowry's staining for glycosaminoglycans. (B) Histopathology of lacrimal gland in sections stained with toluidine blue in wild-type (healthy) mice (WT), untreated Galns−/− mice and Galns−/− mice administered systemically, via intravenous (IV) injection. Original magnification 40×. * P<0.001. ** P<0.0001 vs. Galns−/− male untreated mice.

Figure 14:
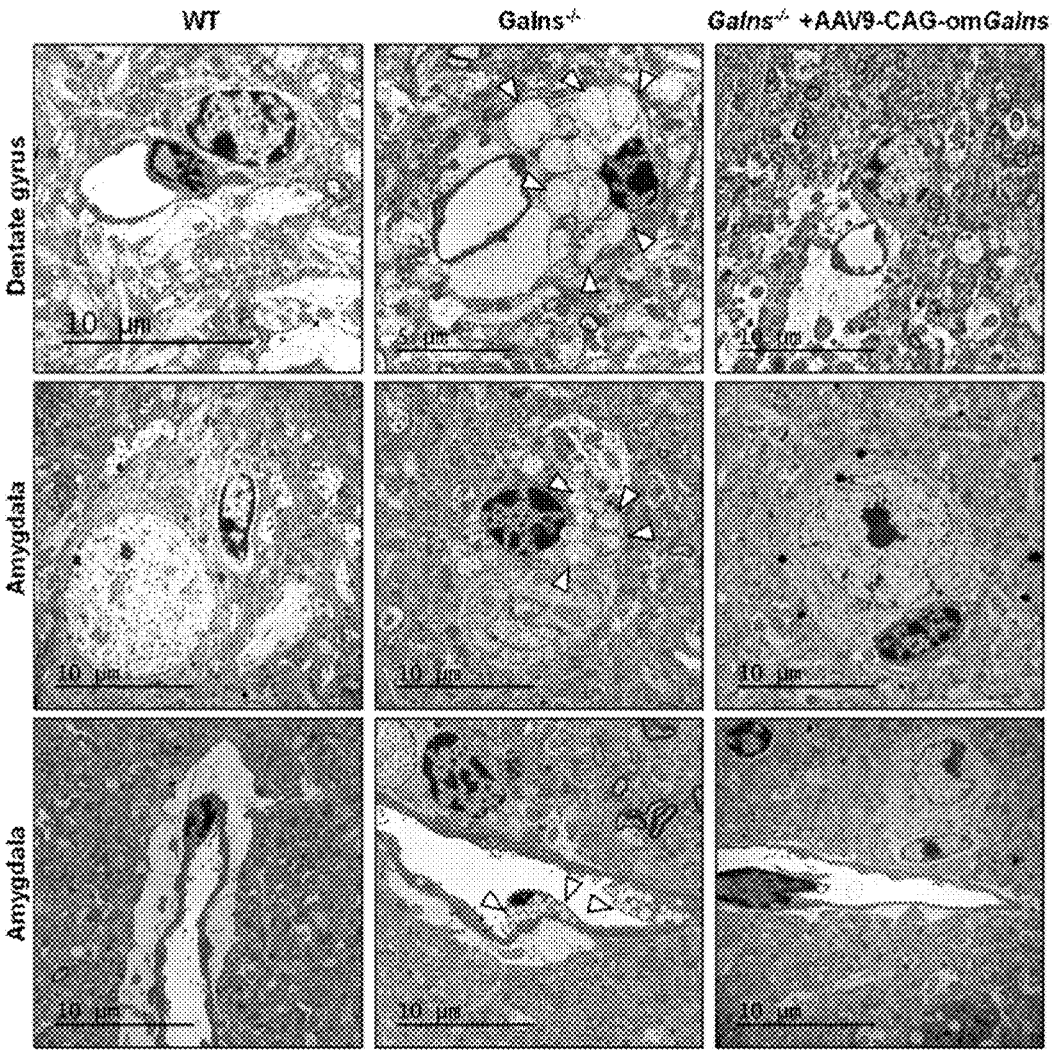

FIG. 14. Intravenous delivery of AAV9 vectors coding for optimized murine GALNS (AAV9-CAG-omGalns) to male mice. Analysis by transmission electron microscopy of the ultrastructure of dentate gyrus and amygdala harvested from 6-month-old healthy WT and Galns−/− males administered systemically with $1\times10^{12}$ vg of vectors coding for optimized murine Galns (AAV9-CAG-omGALNS). Enlarged lysosomes in perivascular macrophages (Dentate gyrus), perineuronal glial cells and endothelial cells (Amygdala) are indicated by arrowheads.

DEPOSIT OF MICROORGANISMS

The plasmids pAAV-CAG-hGALNS (SEQ ID NO: 2), PAAV-CAG-ohGALNS-v1 (SEQ ID NO: 4), pAAV-CAGohGALNS-v2 (SEQ ID NO: 6) and pAAV-CAG-ohGALNS-v3 (SEQ ID NO: 8) were deposited on April 19$^{th}$, 2018 under access numbers DSM 32791, DSM 32792, DSM 32793 and DSM 32794 respectively at the DSMZ—Deutsche Sammlung von Mikroorganismen und Zellkulturen, Inhoffenstraße 7 B, D-38124 Braunschweig, Federal Republic of Germany.

Definitions

The terms “nucleotide sequence” or “isolated nucleotide sequence” or “polynucleotide sequence” or “polynucleotide” or “isolated polynucleotide sequence” are interchangeably used herein and refer to a nucleic acid molecule, either DNA or RNA, containing deoxyribonucleotides or ribonucleotides respectively. The nucleic acid may be double stranded, single stranded, or contain portions of both double stranded or single stranded sequence.

The terms “% sequence identity”% identity” or “% sequence homology” refer to the percentage of nucleotides or amino acids of a candidate sequence that are identical to the nucleotides or amino acids in the sequence of reference, after aligning the sequences to achieve the maximum % sequence identity. In a preferred embodiment, sequence identity is calculated based on the full length of two given SEQ ID NO or on part thereof. The % sequence identity can be determined by any methods or algorithms established in the art, such as the ALIGN, BLAST and BLAST 2.0 algorithms. See Altschul S, et al., Nuc Acids Res. 1977; 25:3389-3402 and Altschul S, et al., J Mol Biol. 1990:215: 403-410.

Herein, the “% sequence identity”, “% identity” or “% sequence homology” is calculated dividing the number of nucleotides or amino acids that are identical after aligning the sequence of reference and the candidate sequence, by the total number of nucleotides or amino acids in the sequence of reference and multiplying the result by 100.

Optionally, in determining the degree of amino acid similarity, the skilled person may also take into account the so-called “conservative” amino acid substitutions, as would be clear to the skilled person. Conservative amino acid substitutions are based on the interchangeability of residues having similar side chains. For example, the group of amino acids having aliphatic side chains includes glycine, alanine, valine, leucine, and isoleucine; the group of amino acids having aliphatic-hydroxyl side chains includes serine and threonine; the group of amino acids having amide-containing side chains includes asparagine and glutamine; the group of amino acids having aromatic side chains includes phenylalanine, tyrosine, and tryptophan; the group of amino acids having basic side chains includes lysine, arginine, and histidine; and the group of amino acids having sulphur-containing side chains includes cysteine and methionine. Substitutional variants of the amino acid sequence disclosed herein are those in which at least one residue in the disclosed sequences has been removed and a different residue inserted in its place. Preferably, the amino acid change is conservative.

Preferred conservative substitutions for each of the naturally occurring amino acids are as follows: Ala to Ser; Arg to Lys; Asn to Gin or His; Asp to Glu; Cys to Ser or Ala; Gin to Asn; Glu to Asp: Gly to Pro; His to Asn or Gln: IIe to Leu or Val; Leu to IIe or Val; Lys to Arg: Gin to Glu; Met to Leu or IIe: Phe to Met, Leu or Tyr; Ser to Thr; Thr to Ser; Trp to Tyr; Tyr to Trp or Phe: and. Val to IIe or Leu.

The terms “codify” or “coding” refer to the genetic code that determines how a nucleotide sequence is translated into a polypeptide or a protein. The order of the nucleotides in a sequence determines the order of amino acids along a polypeptide or a protein.

The term “protein” refers to a macromolecule composed of one or more linear chains of amino acids or polypeptides. Proteins can suffer post-translational modifications, like the conversion of a cysteine residue to 3-oxoalanine, glycosylation or metal binding. Glycosilation of a protein is the addition of different carbohydrates that are linked covalently to the amino acid chain.

The term “transcriptional regulatory region”, as used herein, refers to a nucleic acid fragment capable of regulating the expression of one or more genes. The regulatory regions of the polynucleotides of the invention may include a promoter, plus response elements, activator and enhancer sequences for binding of transcription factors to aid RNA polymerase binding and promote expression, and operator or silencer sequences to which repressor proteins bind to block RNA polymerase attachment and prevent expression.

The term “promoter” must be understood as a nucleic acid fragment that functions to control the transcription of one or more polynucleotides e.g. coding sequences, which is placed 5' upstream of the polynucleotide sequence(s), and which is structurally identified by the presence of a binding site for DNA dependent RNA polymerase, transcription initiation sites and, but not limited to, binding sites for transcription factors, repressors, and any other nucleotide sequences known in the art to act directly or indirectly to regulate the amount of transcription from the promoter.

A promoter is said to be active or is said to drive the expression of a nucleotide sequence operatively linked to it when it can initiate transcription of said nucleotide sequence in an expression system using a gene construct comprising said promoter operably linked to a nucleotide sequence of interest using a suitable assay such a RT-qPCR or Northern blotting (detection of the transcript). The activity of said promoter may also be assessed at the protein level using a suitable assay for the encoded protein such as Western blotting or an ELISA. A promoter is said to be capable to initiate transcription if a transcript can be detected or if an increase in a transcript or protein level is found of at least 5%, 10%, 15%, 20%, 30%, 40%, 50%, 60%, 70%, 80%, 90%, 100%, 200%, 300%, 500%, 1000%, 1500% or 2000% as compared to transcription using a construct which only differs in that it is free of said promoter.

The term “constitutive” promoter refers to a promoter that is active under most physiological and developmental conditions. An “inducible” promoter is a promoter that is preferably regulated depending on physiological or developmental conditions. An inducible promoter may be active after drug delivery or light exposure. A “constitutive” promoter therefore is not regulated in the sense of an “inducible” promoter. A “tissue-specific” promoter is preferably active in specific types of cells/tissues. A ubiquitous promoter may be defined as a promoter that is active in many or in any different tissue(s). Usually, “many” in this context means more than 5 or at least 6, 10, 15, 20 or in 5, 6, 7, 8, 9, 10, 11, 12, 13, 14, 15, 16, 17, 18, 19, 20 different tissues.

The term “CAG” promoter refers to a promoter comprising the chicken β-actin promoter and cytomegalovirus enhancer (Alexopoulou A. et al. BMC Cell Biology 2008; 9(2): 1-11). More precisely, said CAG promoter comprises (i) the cytomegalovirus (CMV) early enhancer element, (ii) the chicken beta-actin promoter, (iii) the first intron of chicken beta-actin gene, and (iv) the intron 2/exon 3 of the rabbit beta-globin gene. The term “hAAT” promoter refers to a hybrid promoter comprising the human α1-antitrypsin promoter and three copies of the hepatocyte control region (HCR) enhancer from the apolipoprotein E.

The term "operably linked" refers to the functional relation and the location of the promoter sequence with respect to the gene of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The term "post-transcriptional regulatory region", as used herein, refers to any polynucleotide that facilitates the expression, stabilization, or localization of the sequences contained in the cassette or the resulting gene product.

The term "vector", as used herein, refers to a construct capable of delivering, and optionally expressing, one or more polynucleotides of interest into a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. There are no limitations regarding the type of vector that can be used. The vector can be a cloning vector, suitable for propagation and for obtaining polynucleotides, gene constructs or expression vectors incorporated to several heterologous organisms.

In a particular embodiment, said vector is an expression vector. The term "expression vector" as used herein refers to a vector designed for gene expression in cells, i.e. the vector is used to introduce a specific gene into a target cell to produce the protein encoded by the gene.

The vector according to the present invention can contain regulatory sequences that act as enhancer and/or promoter regions and lead to efficient transcription of the gene carried on the expression vector. Suitable vectors include prokaryotic expression vectors (e.g. pUC18, pUC19, Bluescript and their derivatives), mpl8, mpl9, pBR322, pMB9, ColEI, pCRI, RP4, phages and shuttle vectors (e.g. pSA3 and pAT28), and eukaryotic expression vectors based on viral vectors (e.g. adenoviruses, adeno-associated viruses as well as retroviruses and lentiviruses), as well as non-viral vectors such as pSilencer 4.1-CMV (Ambion®, Life Technologies Corp., Carsibad, CA, US), pcDNA3, pcDNA3.1/hyg pHCMV/Zeo, pCR3.1, pEFI/His, pIND/GS, pRc/HCMV2, pSV40/Zeo2, pTRACER-HCMV, PUB6/V5-His, pVAXI, pZeoSV2, pCI, pSVL and pKSV-10, pBPV-I, pML2d and pTDTI.

The term "recombinant plasmid" or "plasmid" refers to a small, circular, double-stranded, self-replicating DNA molecule obtained through genetic engineering techniques capable of transferring genetic material of interest to a cell, which results in production of the product encoded by that said genetic material (e.g. a protein polypeptide, peptide or functional RNA) in the target cell. Furthermore, the term "recombinant plasmid" or "plasmid" also refers to a small, circular, double-stranded, self-replicating DNA molecule obtained through genetic engineering techniques used during the manufacturing of viral vectors as carriers of the recombinant vector genome.

The term "recombinant viral vector" or "viral vector" refers to an agent obtained from a naturally-occurring virus through genetic engineering techniques capable of transferring genetic material (e.g. DNA or RNA) of interest to a cell, which results in production of the product encoded by that said genetic material (e.g. a protein polypeptide, peptide or functional RNA) in the target cell.

The terms "adeno-associated virus", "AAV virus", "AAV virion," "AAV viral particle" and "AAV particle", used as synonyms herein, refer to a viral particle composed of at least one capsid protein of AAV (preferably composed of all capsid proteins of a particular AAV serotype) and an encapsulated polynucleotide corresponding to the AAV genome. The wild-type AAV refers to a virus that belongs to the genus Dependovirus, family Parvoviridae. The wild-type AAV genome is approximately 4.7 Kb in length and consists of a single stranded deoxyribonucleic acid (ssDNA) that can be positive or negative-sensed. The wild-type genome includes inverted terminal repeats (ITR) at both ends of the DNA strand, and three open reading frames (ORFs). The ORF rep encodes for four Rep proteins necessary for AAV lifecycle. The ORF cap contains nucleotide sequences encoding capsid proteins: VP1, VP2 and VP3, which interact to form a capsid of icosahedral symmetry. Finally, the AAP ORF, which overlaps with the Cap ORF, encodes for the AAP protein that appears to promote capsid assembly. If the particle comprises a heterologous polynucleotide (i.e. a polynucleotide different from a wild-type AAV genome, such as a transgene to be delivered to a mammalian cell) flanked by AAV ITRs, then it is typically known as "AAV vector particle" or "AAV viral vector" or "AAV vector". The invention also encompasses the use of double stranded AAV also called dsAAV or scAAV.

The term "adeno-associated virus ITRs" or "AAV ITRs", as used herein, refers to the inverted terminal repeats present at both ends of the DNA strand of the genome of an AAV. The ITR sequences are required for efficient multiplication of the AAV genome. Another property of these sequences is their ability to form a hairpin. This characteristic contributes to their self-priming, which allows the primase-independent synthesis of the second DNA strand. The ITRs have also been shown to be required for both integration of the wild-type AAV DNA into the host cell genome (e.g. in the human $19^{th}$ chromosome for serotype 2 AAV) and rescue from it, as well as for efficient encapsidation of the AAV DNA into a fully assembled, deoxyribonuclease-resistant AAV particle. The ITR sequences are about 145 bp in length. Preferably, the entire sequences of the ITRs are used in the genome of the AAV viral vector, although some degree of minor modification of these sequences is permissible. A wild-type ITR sequence may be altered by insertion, deletion or truncation, as long as the ITR mediates the desired functions, e.g. replication, nicking, virus packaging, integration, and/or provirus rescue. Procedures for modifying these ITR sequences are well known in the art. The ITR may be from any wild-type AAV, including but not limited to serotypes 1, 2, 3, 4, 5, 6, 7, 8, 9, 10, 11 or 12 or any other AAV known or later discovered. The AAV comprises two ITRs, which may be the same or different. Further, the two AAV ITRs can be from the same AAV serotype as the AAV capsid, or can be different. In a preferred embodiment, the 5' and 3' AAV ITRs derive from AAV1, AAV2. AAV4, AAV5, AAV7, AAV8 and/or AAV9 Preferably ITRs are from AAV2, AAV8 and/or AAV9 being AAV2 the most preferred. In one embodiment, the AAV2 ITRs are selected to generate a pseudotyped AAV (i.e. an AAV having capsid and ITRs derived from different serotypes).

The expression "recombinant viral genome", as used herein, refers to an AAV genome in which at least one extraneous polynucleotide is inserted into the naturally occurring AAV genome. The genome of the AAV according to the invention typically comprises the cis-acting 5' and 3' inverted terminal repeat sequences (ITRs) and an expression cassette.

The term "gene therapy" refers to the transfer of genetic material (e.g. DNA or RNA) of interest into a cell to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

The term "transduce" or "transduction", as used herein, refers to the process whereby a foreign nucleotide sequence is introduced into a cell via a viral vector.

The term "transfection", as used herein, refers to the process of deliberately introducing purified nucleic acids by non-viral methods into eukaryotic cells.

The term "treat" or "treatment", as used herein, refers to the administration of a compound or composition of the invention to control the progression of a disease. Control of disease progression is understood as the achievement of the beneficial or desired clinical results that include, but are not limited to, reduction of the symptoms, reduction of the duration of the disease, stabilization of pathological states (specifically to avoid additional deterioration), delay of the progression of the disease, improvement in the pathological state, and remission (both partial and total). The control of progression of the disease also involves an extension of survival, compared with the expected survival if treatment is not applied.

The term "effective amount" refers to an amount of a substance sufficient to achieve the intended purpose. For example, an effective amount of an AAV vector to increase galactosamine (N-acetyl)-6-sulfatase (GALNS) activity is an amount sufficient to reduce glycosaminoglycan accumulation. A "therapeutically effective amount" of an expression vector to treat a disease or disorder is an amount of the expression vector sufficient to reduce or eradicate the signals and symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to a mammal, preferably human or non-human mammal, more preferably mouse, rat, other rodents, rabbit, dog, cat, pig, cow, horse or primate, further more preferably human.

DETAILED DESCRIPTION OF THE INVENTION

The present invention provides new polynucleotide sequences and vectors for the treatment of mucopolysaccharidoses, in particular mucopolysaccharidoses type IVA or Morquio A syndrome.

Thus, in a first aspect, the present invention relates to an isolated polynucleotide sequence (hereinafter referred to the "polynucleotide of the invention") having between 75% to 90% identity with the nucleotide sequence as set for in SEQ ID NO: 1 wherein said sequence encodes a functional human galactosamine (N-acetyl)-6-sulfatase.

As mentioned above, MPSIVA is caused by the deficiency in the activity of the enzyme galactosamine (N-acetyl)-6-sulfatase (GALNS). GALNS is a lysosomal enzyme which hydrolysis the sulfate ester group of N-acetylgalactosamine-6-sulfate at the non-reducing end of chondroitin-6-sulfate (C6S) and that of galactose-6-sulfate at the non-reducing end of keratan sulfate (KS). As a consequence of the sustained accumulation of non-degraded C6S and KS, progressive cellular damage occurs, resulting in multisystemic disease.

The inventors have shown that in vivo administration of vectors containing different versions of the human galactosamine (N-acetyl)-6-sulfatase (GALNS) expressing cassette, wherein said GALNS encoding sequence has between 75% to 90% identity with the wild type encoding GALNS nucleotide sequence, resulted in a substantial increase in GALNS activity over the levels measured in MPSIVA animals. Indeed, the levels of human GALNS activity reached with the expression vectors containing the sequences having between 75% to 90% identity with the wild type-were higher than those mediated by the vector containing the wild-type sequence.

The invention also contemplates polynucleotide sequences having between 75% to 90% identity with the nucleotide sequence encoding the wild type GALNS as set for in SEQ ID NO: 1 wherein said sequences encodes functional human GALNS variants and fragments known in the art. Thus, the invention should be construed to include DNA encoding functionally equivalent variants of GALNS.

The term "functionally equivalent variant", as used herein, relates to any enzyme substantially homologous to the enzyme encoded by the polypeptide sequence of GALNS and that preserves the biological activity of GALNS. The sequence of such functional equivalent variants can be obtained from the sequence of GALNS by means of insertion, substitution or deletion of one or more amino acids and which substantially preserves the biological activity of GALNS. Methods for determining whether a variant preserves the biological activity of the native GALNS are widely known to the skilled person and include any of the assays used in the experimental part of the present application. Particularly, functionally equivalent variants of GALNS encompassed by the present invention have at least one of the functions of GALNS such as, for example, normalize or reduce glycosaminoglycan (GAG) levels, in particular, C6S and KS levels.

In the Examples section of the present invention it is detailed a method suitable for determining the ability of a functional GALNS enzyme to reduce or normalize said GAG levels.

As shown in the Examples accompanying the present invention, the polynucleotide sequences of the present invention encodes functional GALNS enzymes. Said enzymes show enhanced activity when compared to the WT. The results show a restoration of GALNS activity after vector administration, which led to a substantial increase in galactosamine (N-acetyl)-6-sulfatase activity over the levels measured in MPSIVA animals. As it is shown in the Examples accompanying the present invention, GALNS activity levels ranged from 1500% to 2600% of WT levels in liver.

In a preferred embodiment, a polypeptide is considered a functionally equivalent variant of GALNS enzyme if it shows ability in the functions as mentioned above, particularly, if it is capable of degrading the glycosaminoglycans keratan sulfate (KS) and chondroitin-6-sulfate (C6S) with at least 10%, 20%, 30%, 40%, 50%, 60%, 70%, 80%, 90% or 100% of the ability of the GALNS wild type polypeptide, preferably with at least 50%, 60%, 70%, 80%, 90% or 100% of the ability of the GALNS wild type polypeptide.

The functionally equivalent variants of GALNS are polypeptides substantially homologous to the native GALNS. The expression "substantially homologous", relates to a protein sequence when said protein sequence has a degree of identity with respect to the GALNS wild type sequence of at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% o or at least 99%. The degree of identity between two polypeptides is determined using computer algorithms and methods that are widely known to the persons skilled in the art. The identity between two amino acid sequences is preferably determined by using the BLASTP algorithm [BLAST Manual, Altschul, S., et al, NCBI NLM NIH Bethesda, Md. 20894. Altschul, S., et al, J. Mol. Biol. 215: 403-410 (1990)], though other similar algorithms can also be used.

Functionally equivalent variants of GALNS may be obtained by replacing nucleotides within its coding polynucleotide, accounting for codon preference in the host cell that is to be used to produce the GALNS.

Functionally equivalent variants of GALNS may be generated by making conservative amino acid changes and testing the resulting variant in one of the functional assays described above or other functional assays known in the art. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine: a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

In a particular embodiment of the invention, the nucleotide sequence encoding the GALNS protein or a functionally equivalent variant thereof contained in the polynucleotide of the invention has between 75% to 90% identity with the nucleotide sequence as set for in SEQ ID NO: 1. In a more particular embodiment, said nucleotide sequence has between 80% to 85% identity with the nucleotide sequence as set for in SEQ ID NO: 1. In a more preferred embodiment, said sequence is selected from the group consisting of SEQ ID NO: 3, SEQ ID NO: 5, and SEQ ID NO: 7.

In another embodiment of the invention, the GALNS protein encoded by the polynucleotide of the invention is selected from the group consisting of human GALNS (hGALNS) and mouse GALNS (mGALNS), preferably human GALNS (hGALNS).

The polynucleotide of the invention may further comprise expression control sequences including, but not limited to, appropriate transcription regulatory sequences (i.e. initiation, termination, promoter, and enhancer), efficient RNA processing signals (e.g. splicing and polyadenylation (polyA) signals), sequences that stabilize cytoplasmic mRNA, sequences that enhance translation efficiency (i.e. Kozak consensus sequence), sequences that enhance protein stability, and when desired, sequences that enhance secretion of the encoded product. A great number of expression control sequences are known in the art and may be utilized according to the present invention.

Thus, according to the invention, in a particular embodiment the polynucleotide of the invention has a transcriptional regulatory region operatively linked to a nucleotide sequence encoding GALNS. In a particular embodiment of the invention, said transcriptional regulatory region comprises a promoter. In another particular embodiment of the invention, the transcriptional regulatory region of the polynucleotide of the invention further comprises an enhancer operatively linked to the promoter.

The polynucleotide of the invention could be incorporated into a vector. In a particular embodiment, said vector is an expression vector. Thus, in another aspect, the invention relates to an expression vector, herein referred to as "vector of the invention", containing the polynucleotide of the invention. In a particular embodiment, said vector is a plasmid. In another particular embodiment said vector is an AAV vector, said AAV vector containing a recombinant viral genome comprising a polynucleotide according to the invention.

All the embodiments disclosed in the context of the polynucleotide of the invention are also applicable to the vector of the invention.

In another embodiment, the polynucleotide sequence of the invention is flanked by AAV ITRs. In a more particular embodiment, said AAV ITRs are AAV2 ITRs.

In another embodiment, the polynucleotide of the invention further comprises a post-transcriptional regulatory region. The term "post-transcriptional regulatory region", as used herein, refers to any polynucleotide that facilitates the expression, stabilization, or localization of the sequences contained in the cassette or the resulting gene product. The post-transcriptional regulatory region may be, without limitation, the Woodchuck Hepatitis Virus post-transcriptional region (WPRE). The term "woodchuck hepatitis B virus post-regulatory element" or "WPRE", as used herein, refers to a DNA sequence that, when transcribed, creates a tertiary structure capable of enhancing the expression of a gene.

In another embodiment, the polynucleotide sequence of the invention further comprises a polyadenylation signal.

The term "polyadenylation signal", as used herein, relates to a nucleic acid sequence that mediates the attachment of a polyadenine tail to the 3' terminus of the mRNA. Suitable polyadenylation signals include, without limitation, the SV40 early polyadenylation signal, the SV40 late polyadenylation signal, the HSV thymidine kinase polyadenylation signal, the protamine gene polyadenylation signal, the adenovirus 5 Elb polyadenylation signal, the bovine growth hormone polyadenylation signal, the human variant growth hormone polyadenylation signal, the rabbit beta-globin poly A signal and the like. In a particular embodiment, the polyadenylation signal is the rabbit beta-globin poly A signal or functional variants and fragments thereof.

As mentioned above, in a particular embodiment of the invention, the polynucleotide of the invention is incorporated into a vector. In a particular embodiment, said vector is an expression vector. In a particular embodiment, said expression vector comprises a promoter sequence operatively linked to said polynucleotide sequence. Said promoter can be a constitutive promoter or a tissue specific promoter. In a particular embodiment, said promoter is selected from a CAG promoter, hAAT promoter or CMV promoter. In a preferred embodiment of the invention, said promoter is the CAG promoter. In another particular embodiment, said promoter is a hAAT promoter.

The polynucleotide of the invention comprises a nucleotide sequence encoding GALNS or a functionally equivalent variant thereof. In an embodiment, said nucleotide sequence is the nucleotide sequence encoding human GALNS, which corresponds to the sequence of the NCBI database with accession number NM_000512.4, more particularly it is SEQ ID NO: 1. In a preferred embodiment, the nucleotide sequence is a variant of the nucleotide sequence encoding human GALNS. More particularly, said sequence has between 75 to 90% identity with the nucleotide sequence as set for in SEQ ID NO: 1. More particularly, said sequence has between 80 to 85% identity with the nucleotide sequence as set for in SEQ ID NO: 1. Preferably, said sequence is a sequence selected from the group consisting of SEQ ID NO: 3, SEQ ID NO: 5, and SEQ ID NO: 7.

In a more particular embodiment, the expression vector according to the invention is selected from the group consisting of plasmid pAAV-CAG-ohGALNS-v1, with accession number DSM 32792, as set forth in SEQ ID NO: 4, plasmid pAAV-CAG-ohGALNS-v2 with accession number DSM 32793, as set forth in SEQ ID NO: 6, pAAV-CAG-ohGALNS-v3 with accession number DSM 32794, as set forth in SEQ ID NO: 8.

In another particular embodiment, the invention refers to an expression vector. More particularly, an adeno-associated viral vector or AAV vector, said AAV vector containing a recombinant viral genome wherein said recombinant viral genome comprises a polynucleotide comprising a transcriptional regulatory region operatively linked to a nucleotide sequence encoding GALNS or a functional equivalent variant thereof.

AAV according to the present invention include any serotype of the AAV known serotypes. In general, the different serotypes of AAV have genomic sequences with a significant homology, providing an identical series of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3A and 3B), AAV4, AAV5. AAV6, AAV7, AAV8. AAV9, AAV10, AAV11, avian AAV, bovine AAV, canine AAV, equine AAV, ovine AAV, and any other AAV. Examples of the sequences of the genome of the different AAV serotypes may be found in the literature or in public databases such as GenBank. See GenBank accession numbers AF028704.1 (AAV6), NC006260 (AAV7), NC006261 (AAV8), and AX753250.1 (AAV9). In a preferred embodiment, the AAV vector of the invention is of a serotype selected from the group consisting of the AAV2, AAV5, AAV7, AAV8, AAV9, AAV10 and AAVrh10 serotypes. In a preferred embodiment, said AAV vector of the invention is of serotype 9, AAV9 or serotype 8, AAV8.

In a particular embodiment said AAV vector contains a human or murine GALNS sequence. In an embodiment, said vector contains the nucleotide sequence encoding human GALNS, which corresponds to the sequence of the NCBI database with accession number NM_000512.4, more particularly it is SEQ ID NO: 1. In a preferred embodiment, said vector contains a nucleotide sequence which is a variant of the nucleotide sequence encoding human GALNS. More particularly, said sequence has between 75 to 90% identity with the nucleotide sequence as set for in SEQ ID NO: 1. More particularly, said sequence has between 80 to 85% identity with the nucleotide sequence as set for in SEQ ID NO: 1. Preferably, said sequence is a sequence selected from the group consisting of SEQ ID NO: 3, SEQ ID NO: 5, and SEQ ID NO: 7.

In another particular embodiment of the invention, the AAV vector is the AAV9-CAG-hGALNS, SEQ ID NO: 12, which contains the nucleotide sequence SEQ ID NO: 1 linked to the CAG promoter. In another embodiment, the AAV vector is the AAV9-CAG-ohGALNS-v1, SEQ ID NO: 13 containing the nucleotide sequence SEQ ID NO: 3 linked to the CAG promoter. In another embodiment, the AAV is the AAV9-CAG-ohGALNS-v2, SEQ ID NO: 14 containing the nucleotide sequence SEQ ID NO: 5 linked to the CAG promoter. In another embodiment, the AAV vector is the AAV9-CAG-ohGALNS-v3. SEQ ID NO: 15 containing the nucleotide sequence SEQ ID NO: 7 linked to the CAG promoter.

In a preferred embodiment, the AAV of the invention contains a recombinant viral genome comprising a polynucleotide sequence comprising in the 5' to 3' direction. (i) a 5' AAV2 ITR, (ii) a CMV immediate-early enhancer, (iii) a chicken beta-actin promoter, (iv) the first intron of chicken beta-actin gene, (v) the intron 2/exon 3 from the rabbit beta-globin gene, (vi) a GALNS cDNA or a functionally equivalent variant thereof, (vii) a poly A signal, such as the rabbit beta-globin poly A signal, and (viii) a 3' AAV2 ITR. Those skilled in the art will appreciate that the vector genome can comprise other sequences (e.g. intervening sequences between the sequences specifically described above). Components (i) to (v) have the meaning typically understood by the person skilled in the art.

In a preferred embodiment, the recombinant viral genome comprises the nucleotide sequence SEQ ID NO: 12. Specifically, the 5' AAV2 ITR comprises nucleotides 1-131, the CAG promoter comprises nucleotides 185-1707, the human GALNS cDNA comprises nucleotides 1918-3494, the rabbit beta-globin poly A signal comprises nucleotides 3520-4048, and the 3' AAV2 ITR comprises nucleotides 4107-4215 of SEQ ID NO: 12.

In another preferred embodiment, the recombinant viral genome comprises the nucleotide sequence SEQ ID NO: 13. Specifically, the 5' AAV2 ITR comprises nucleotides 1-131, the CAG promoter comprises nucleotides 185-1707, the human GALNS cDNA comprises nucleotides 1918-3494, the rabbit beta-globin poly A signal comprises nucleotides 3520-4048, and the 3' AAV2 ITR comprises nucleotides 4107-4215 of SEQ ID NO: 13.

In another preferred embodiment, the recombinant viral genome comprises the nucleotide sequence SEQ ID NO: 14. Specifically, the 5' AAV2 ITR comprises nucleotides 1-120, the CMV enhancer comprises nucleotides 194-557, the beta-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GALNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 14.

In another preferred embodiment, the recombinant viral genome comprises the nucleotide sequence SEQ ID NO: 15. Specifically, the 5' AAV2 ITR comprises nucleotides 1-120, the CMV enhancer comprises nucleotides 194-557, the beta-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GALNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 15.

Modified AAV sequences also can be used in the context of the present invention. Such modified sequences e.g.

include sequences having at least about 70%, at least about 75%, at least about 80%, at least about 85%, at least about 90%, at least about 95% or more nucleotide and/or amino acid sequence identity (e.g. a sequence having about 75-99% nucleotide or amino acid sequence identity) to an AAV ITR or VP of any of the serotypes known and that maintain the function of said components. Assays for determining the function of AAV ITR or VP are known in the art. Said modified sequences can be used in place of wild-type AAV ITR or VP sequences.

The AAV vector of the invention comprises a capsid from any serotype. In general, the different AAV serotypes have genomic sequences of significant homology at the amino acid and the nucleic acid levels, providing an identical set of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3 A and 3B), AAV4, AAV5, AAV6. AAV7. AAV8, AAV9, AAV10, AAV11, avian AAV, bovine AAV, canine AAV, equine AAV, ovine AAV, and any other AAV. Examples of the sequences of the genome of the different AAV serotypes may be found in the literature or in public databases such as GenBank. See GenBank accession numbers AF028704.1 (AAV6), NC006260 (AAV7), NC006261 (AAV8), and AX753250.1 (AAV9). In a preferred embodiment, the adeno-associated viral vector of the invention is of a serotype selected from the group consisting of the of AAV2, AAV5, AAV7, AAV8, AAV9, AAV10 and AAVrh10 serotypes. In a more preferred embodiment, said AAV is AAV serotype 9, AAV9 or AAV serotype 8. AAV8.

The genome of the AAV vector of the invention lacks the rep and cap open reading frames. Such AAV vectors can only be replicated and packaged into infectious viral particles in host cells that have been transfected with a vector encoding and expressing the rep and cap gene products (i.e. AAV Rep and Cap proteins), and wherein the host cells have been transfected with a vector which encodes and expresses a proteins from the adenovirus.

Pharmaceutical Compositions of the Invention

The polynucleotide o expression vector of the invention can be administered to the human or animal body by conventional methods, which require its formulation in a pharmaceutical composition. Thus, in a second aspect, the invention relates to a pharmaceutical composition (hereinafter referred to as “pharmaceutical composition of the invention”) comprising a therapeutically effective amount of the polynucleotide of the invention or the vector of the invention. The pharmaceutical composition may further include a pharmaceutically acceptable carrier.

All the embodiments disclosed in the context of the polynucleotide of the invention of the vector of the invention are also applicable to the pharmaceutical compositions of the invention.

The term “therapeutically effective amount” refers to the quantity of the polynucleotide, vector or AAV vector of the invention calculated to produce the desired effect and will generally be determined, among other reasons, by the own features of the polynucleotide, vector or AAV vector of the invention and the therapeutic effect to be obtained. Thus, said quantity that will be effective in the treatment of a disease can be determined by standard clinical techniques described herein or otherwise known in the art. The precise dose used in the formulation will depend on the administration route. The initial doses can be estimated from in vivo data (e.g. animal models) using techniques well known in the state of the art. Someone with normal experience in the state of the art can easily optimize administration to humans based on the data in animals.

In a particular embodiment, the dosage of the formulation can be measured or calculated as viral particles or as genome copies (“GC”)/viral genomes (“vg”).

Any method known in the art can be used to determine the genome copy (GC) number per milliliter of the viral compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting a specific region of the viral genome.

The terms “pharmaceutically acceptable carrier.” “pharmaceutically acceptable diluent.” “pharmaceutically acceptable excipient”, or “pharmaceutically acceptable vehicle”, used interchangeably herein, refer to a non-toxic solid, semisolid, or liquid filler, diluent, encapsulating material, or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art.

The pharmaceutical composition can be formulated in accordance with routine procedures as a pharmaceutical composition adapted for intravenous, subcutaneous, intramuscular, intra-cerebrospinal fluid (CSF) e.g. intracisternal or intra-cerebroventricular, administration to human beings. In a preferred embodiment, the pharmaceutical composition is for intravenous or intra-cerebrospinal fluid (CSF) administration. More preferably, the pharmaceutical composition is for intravenous administration.

The AAV vector may be formulated for parenteral administration by injection (e.g. by bolus injection or continuous infusion). Formulations for injection may be presented in unit dosage form (e.g. in ampoules or in mono or multi-dose containers) with an added preservative. The viral compositions may take such forms as suspensions, solutions, or emulsions in oily or aqueous vehicles, and may contain formulatory agents such as suspending, stabilizing, or dispersing agents. Liquid preparations of the AAV formulations may be prepared by conventional means with pharmaceutically acceptable additives such as suspending agents (e.g. sorbitol syrup, cellulose derivatives or hydrogenated edible fats), emulsifying agents (e.g. lecithin or acacia), non-aqueous vehicles (e.g. almond oil, oily esters, ethyl alcohol or fractionated vegetable oils), and preservatives (e.g. methyl or propyl-p-hydroxybenzoates or sorbic acid). The preparations may also contain buffer salts. Alternatively, the compositions may be in powder form for constitution with a suitable vehicle (e.g. sterile pyrogen-free water) before use. When necessary, the composition may also include a local anaesthetic such as lidocaine to relieve pain at the injection site. When the composition is going to be administered by infiltration, it can be dispensed with an infiltration bottle which contains water or saline solution of pharmaceutical quality. When the composition is administered by injection, a water vial can be provided for injection or sterile saline solution, so that the ingredients can be mixed before administration. Preferably, the pharmaceutically acceptable carrier is saline solution and a detergent such as polyethylene-polyoxypropylene block copolymer, Pluronic F66®.

Compositions of the invention may be formulated for delivery to animals for veterinary purposes (e.g. livestock (cattle, pigs, others)), and other non-human mammalian subjects, as well as to human subjects. The pharmaceutical composition of the Invention can be formulated with a physiologically acceptable carrier for use in gene transfer and gene therapy applications.

Also encompassed is the use of adjuvants in combination with or in admixture with the polynucleotide, vector or AAV vector of the invention. Adjuvants contemplated include. but are not limited to, mineral salt adjuvants or mineral salt gel adjuvants, particulate adjuvants, microparticulate adjuvants, mucosal adjuvants.

Adjuvants can be administered to a subject as a mixture with the polynucleotide, vector or AAV vector of the invention, or used in combination.

The pharmaceutical composition of the invention may be administered locally or systemically. In an embodiment, the pharmaceutical composition is administered near the tissue or organ whose cells are to be transduced. In a particular embodiment, the pharmaceutical composition of the invention is administered systemically.

The term "systemically administered" and "systemic administration", as used herein, means that the polynucleotide, vectors, AAV vectors or compositions of the invention may be administered to a subject in a non-localized manner. The systemic administration may reach several organs or tissues throughout the body of the subject or may reach specific organs or tissues of the subject. For example, the intravenous administration may result in the transduction of more than one tissue or organ in a subject. The pharmaceutical compositions of the invention may be administered in a single dose or, in particular embodiments of the invention, multiple doses (e.g. two, three, four, or more administrations) may be employed to achieve a therapeutic effect.

In a preferred embodiment of the invention, the pharmaceutical composition of the invention is administered in a single dose, i.e. it is administered once in life time.

Thus, in another aspect, the invention relates to a polynucleotide or a vector according to the invention or a pharmaceutical composition according to the invention for use in medicine.

In a further aspect, the invention relates to a polynucleotide or a vector according to the invention or a pharmaceutical composition according to the invention for use in the treatment of mucopolysaccharidosis type IVA or Morquio A syndrome.

As shown in the Examples accompanying the present invention, AAV vectors containing different versions of the human galactosamine (N-acetyl)-6-sulfatase expressing cassette were delivered intravenously to 2-month-old MPSIVA-affected mice via tail vein injection. GALNS activity analysis showed that transduction with all galactosamine (N-acetyl)-6-sulfatase-containing vectors resulted in a substantial increase in galactosamine (N-acetyl)-6-sulfatase activity over the levels measured in MPSIVA animals.

Thus, in another aspect, the invention relates to a polynucleotide or a vector according to the invention or a pharmaceutical composition according to the invention for increasing galactosamine (N-acetyl)-6-sulfatase activity.

In another aspect, the invention provides a method for the treatment and/or prevention of a mucopolysaccharidosis type IVA in a subject in need thereof which comprises the administration to said subject of a polynucleotide according to the invention or the vector according the invention or a pharmaceutical composition according to the invention.

The terms "prevent," "preventing," and "prevention", as used herein, refer to inhibiting the inception or decreasing the occurrence of a disease in a subject. Prevention may be complete (e.g. the total absence of pathological cells in a subject) or partial. Prevention also refers to a reduced susceptibility to a clinical condition. The term "treat" or "treatment", as used herein, refers to the administration of a polynucleotide, or vector or AAV vector or a pharmaceutical composition of the invention to control the progression of a disease after its clinical signs have appeared. Control of the disease progression is understood to mean the achievement of the beneficial or desired clinical results that include, but are not limited to, reduction of the symptoms, reduction of the duration of the disease, stabilization of pathological states (specifically to avoid additional deterioration), delay of the progression of the disease, improvement of the pathological state, and remission (both partial and total). The control of progression of the disease also involves an extension of survival, compared with the expected survival if treatment is not applied.

The term "subject", as used herein, refers to an individual or animal, such as a human being, a non-human primate (e.g. chimpanzees and other apes and monkey species), a farm animal (e.g. birds, fish, cattle, sheep, pigs, goats, and horses), a domestic mammal (e.g. dogs and cats), or a laboratory animal (e.g. rodents, such as mice, rats and guinea pigs). The term includes a subject of any age or sex. In a preferred embodiment the subject is a mammal, preferably a human being.

Methods for Obtaining the Aavs of the Invention

The invention also relates to a method for obtaining the AAV vectors of the invention. Said AAV vectors can be obtained by introducing the polynucleotides of the invention into cells that express the Rep and Cap proteins constitutively or wherein the Rep and Cap coding sequences are provided in plasmids or vectors.

Thus, in another aspect, the invention relates to a method for obtaining an AAV vector comprising the steps of:

(i) providing a cell comprising a polynucleotide of the invention, AAV cap proteins, AAV rep proteins and, optionally, viral proteins upon which AAV is dependent for replication,
(ii) maintaining the cell under conditions adequate for assembly of the AAV and
(i) purifying the adeno-associated viral vector produced by the cell.

Any cell capable of producing AAV vectors can be used in the present invention.

The polynucleotide of the invention used in this method has been described previously. Any of the embodiments disclosed in the context of the polynucleotides of the invention is applicable in the context of the methods for obtaining AAV of the invention.

The term "cap protein", as used herein, refers to a polypeptide having at least one functional activity of a native AAV cap protein (e.g. VP1, VP2, and VP3). Examples of functional activities of cap proteins include the ability to induce formation of a capsid, facilitate accumulation of single-stranded DNA, facilitate AAV DNA packaging into capsids (i.e. encapsidation), bind to cellular receptors, and facilitate entry of the virion into host cells. In principle, any cap protein can be used in the context of the present invention.

In a preferred embodiment, the cap proteins are derived from AAV8 or AAV9.

The term "capsid", as used herein, refers to the structure in which the viral genome is packaged. A capsid consists of several oligomeric structural subunits made of proteins. For instance, AAV have an icosahedral capsid formed by the interaction of three capsid proteins: VP1, VP2 and VP3.

The term "rep protein", as used herein, refers to a polypeptide having at least one functional activity of a native AAV rep protein. A "functional activity" of a rep protein is any activity associated with the physiological function of the protein, including facilitation of replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. In a particular embodiment. AAV rep genes derive from the serotype AAV2.

The expression "viral proteins upon which AAV is dependent for replication", as used herein, refers to polypeptides which perform functions upon which AAV is dependent for replication (i.e. "helper functions"). The helper functions include, without limitation, those functions required for activation of AAV gene transcription, stage specific AAV mRNA splicing, AAV DNA replication, synthesis of cap proteins, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus El, E2a, VA, and E4 or herpesvirus UL5, UL8, UL52, and UL29, and herpesvirus polymerase.

The polynucleotide of the invention, or the genes AAV rep. AAV cap and genes providing helper functions can be introduced into the cell by incorporating said genes into a vector such as, for example, a plasmid, and introducing said vector into the cell.

The genes can be incorporated into the same plasmid or into different plasmids. In a preferred embodiment, the polynucleotide of the invention is incorporated in one plasmid, the AAV rep and cap genes are incorporated into another plasmid and the genes providing helper functions are incorporated into another plasmid.

The plasmids containing the polynucleotide of the invention and or the AAV rep and cap genes or genes providing helper functions can be introduced into the cell by using any suitable method well known in the art. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In a particular embodiment, the transfection is carried out by means of co-precipitation with calcium phosphate. When the cell lacks the expression of any of the AAV rep and cap genes and genes providing adenoviral helper functions, said genes can be introduced into the cell simultaneously with the polynucleotide of the invention. Alternatively, said genes can be introduced in the cell before or after the introduction of the polynucleotide of the invention.

In a particular embodiment, the cells are transfected simultaneously with three plasmids, i) a plasmid comprising the polynucleotide of the invention, ii) a plasmid comprising the AAV rep and cap genes and ill) a plasmid comprising the genes providing the helper functions.

Step (ii) of the method of the invention involves maintaining the cell under conditions adequate for assembly of the AAV.

Methods of culturing cells and exemplary conditions which promote the release of AAV vector particles, such as the lysing of the cells, may be carried out as described in examples herein. Producer cells are grown for a suitable period of time in order to promote the assembly of the AAV and the release of viral vectors into the media. Generally, time of culture is measured from the point of viral production. For example, in the case of AAV, viral production generally begins upon supplying helper virus function in an appropriate producer cell as described herein.

Step (iii) of the method of the invention involves purifying the AAV vector produced by the cell.

Any method for the purification of the AAV from said cells or said culture medium can be used for obtaining the AAV of the invention. In a particular embodiment, the AAV of the invention are purified following an optimized method based on a polyethylene glycol precipitation step and two consecutive cesium chloride (CsCl) gradients.

Various naturally occurring and engineered AAV, their encoding nucleic acids, AAV cap and rep proteins, as well as methods for isolating or generating, propagating, and purifying such AAV, and in particular, their capsids, suitable for use in production of AAV are known in the art.

The present invention further provides an isolated cell comprising the polynucleotide sequence of the invention encoding the GALNS protein or a functionally equivalent variant thereof.

All the embodiments disclosed in the context of the polynucleotides, vectors or AAV vectors of the invention and the pharmaceutical compositions of the invention are applicable to the therapeutic methods of the invention.

General Procedures

1. Recombinant AAV Vectors

The AAV vectors described herein were obtained by triple transfection. The materials required for making the vectors were: HEK293 cells (expressing adenoviral E1 genes), helper plasmid providing adenovirus functions, plasmid providing AAV rep genes from serotype 2 and cap genes from serotypes 8 or 9 (AAV8 or AAV9) and, finally, the backbone plasmid with AAV2 ITRs and the construct of interest.

To generate galactosamine (N-acetyl)-6-sulfatase-expressing AAV vectors, the optimized or non-optimized coding sequences of human or murine galactosamine (N-acetyl)-6-sulfatase were cloned into an AAV backbone plasmid under the control of the ubiquitous hybrid CAG promoter or liver-specific hAAT promoter. Large-scale production of plasmids was done using an EndoFree Plasmid Megaprep Kit (Qiagen).

Vectors were generated by helper virus-free transfection of HEK293 cells using three plasmids with modifications (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by the viral ITRs of serotype 2 AAV (described above); 2) a plasmid carrying the AAV rep2 and the cap8 or cap9 genes; and 3) a plasmid carrying the adenovirus helper functions. Vectors were purified by two consecutives cesium chloride gradients using an optimized protocol as previously described (Ayuso et al., 2010). Vectors were dialyzed against PBS+0.001% Pluronic® F68, filtered, titered by qPCR and stored at −80° C. until use.

The vectors of the present invention were constructed according to molecular biology techniques well known in the art.

2. In Vitro Transfection Studies

HEK293 cells were transfected with 4 μg of pAAV-CAG-omGALNS, pAAV-hAAT-omGALNS, pAAV-CAG-hGALNS, pAAV-CAG-ohGALNS-v1, pAAV-CAG-ohGALNS-v2 or pAAV-CAG-ohGALNS-v3 using Lipofectamine® 2000 (Invitrogen, Thermo Fisher Scientific, CA, USA) following the manufacturer's instructions. After 48 hours, cells and culture media were harvested and processed for protein extraction.

Protein extracts were obtained by sonication of cells in 250 μl of Mili-Q water and protein content was quantified using Bradford protein assay (Bio-Rad, Hercules, CA, US). Galactosamine (N-acetyl)-6-sulfatase activity was determined in 1 μg of cell protein extracts and 5 μl of culture media and normalized by total amount of protein and volume, respectively, with a 4-methylumbelliferone-derived fluorogenic substrate (Toronto Rerearch Chemicals Inc, Ontario, Canada), as described previously (van Diggelen et al., 1990).

3. Animals

C57BL/6N-A/a embryonic stem cells carrying a reporter (LacZ) gene tagged insertion in the Galns gene available through the International Mouse Phenotyping Consortium (IMPC, www.mousephenotype.org) were obtained. Clones were microinjected in C57BL/6JOlaHsd blastocysts in the Transgenic Animal Unit of the Center of Animal Biotechnology and Gene Therapy (CBATEG) at Universitat Autònoma de Barcelona (UAB), and the resulting male chimeras were bred with C57Bl/6NTac females to generate Galns knock-out offspring (MPSIVA or $Galns^{-/-}$ mice). Genotype was determined on genomic DNA from tail-clipped samples with a PCR analysis that amplifies a sequence encompassing the targeted mutation. The sequences of the respective sense and antisense primers were: Sense primer: 5' CCA GGG AAT GTC CCA CCT ATT T 3' (SEQ ID NO: 20); Antisense primer: 5' GTC AGG TTG ACA CGA AGC TG 3' (SEQ ID NO: 21); and Antisense primer KO: 5' GGA ACT TCG GTT CCG GCG 3' (SEQ ID NO: 22). Sense and Antisense primers allow genotyping WT mice. Sense and Antisense primer KO allow genotyping $Galns^{-/-}$ mice.

Mice were fed ad libitum with a standard diet (Harlan. Tekland) and maintained under a light-dark cycle of 12 h (lights on at 9:00 A.M.).

Due to the lack of GALNS activity these animals show as early as one-month of age several pathological features characteristic of MPSIVA disease, including accumulation of glycosaminoglycans (GAGs) and enlargement of the lysosomal compartment in different regions of the epiphyseal plate from femur and tibia. Furthermore, many of these pathological findings are exacerbated when animals get older, suggesting worsening of the pathology as aged animals. Likewise, as animals get older GAG accumulation in peripheral organs such as liver, heart and spleen is also observed. However, no significant differences are observed in lifespan between Galns-' and WT littermates.

4. Vector Administration to Mice

For intravenous vector delivery of AAV8-hAAT-omGALNS vectors, a total dose of $1\times10^{11}$ vg were injected to mice in a total volume of 200 μl through tail vein of 3-4 week-old $Galns^{-/-}$ animals. A similar cohort of animals was injected with $1\times10^{11}$ vg control non-coding (AAV8-hAAT-null) vector.

For intravenous vector delivery of AAV8-CAG-omGALNS vectors to mice, a total dose of $1\times10^{12}$ vg were injected to mice in a total volume of 200 μl through tail vein of 3-4 week-old $Galns^{-/-}$ animals. A similar cohort of animals was injected with $1\times10^{12}$ vg control non-coding (AAV8-CAG-null) vector.

For intravenous vector delivery of AAV9-CAG-omGALNS vectors to mice, a total dose of $1\times10^{12}$ vg were injected to mice in a total volume of 200 μl through tail vein of 3-4 week-old $Galns^{-/-}$ animals. A similar cohort of animals was injected with $1\times10^{12}$ vg control non-coding (AAV9-CAG-null) vector.

At 7 months of age, 6 months post vector administration, mice were sacrificed and tissues were harvested.

For intravenous vector delivery, $5\times10^{10}$ vector genomes of AAV9 vectors baring different versions of the human galactosamine (N-acetyl)-6-sulfatase coding sequence were delivered to mice in a total volume of 200 μl through tail vein injection of 2-month-old $Galns^{-/-}$ animals. WT and non-treated $Galns^{-/-}$ animals were used as controls.

At 2.5 months of age, 15 days post vector administration, mice were sacrificed and tissues were harvested.

5. Sample Collection

At sacrifice, animals were deeply anesthetized and then transcardially perfused with 50 ml of PBS to completely clear blood from tissues. The entire brain and multiple somatic tissues (including liver, spleen, kidney, lung, heart, adipose tissue, eye, lacrimal gland and bones) were collected and either frozen in liquid nitrogen and stored at −80° C. or immersed in formalin for subsequent histological analyses.

6. Galactosamine (N-Acetyl)-6-Sulfatase Activity and Glycosaminoglycan Quantification Liver and adipose tissue samples were sonicated in Mili-Q water and femur samples were homogenized in homogenization buffer consisting of 25 mmol/l Tris-HCl, pH 7.2, and 1 mmol/l phenylmethylsulfonyl fluoride. Galactosamine (N-acetyl)-6-sulfatase activity was determined with a 4-methylumbelliferone-derived fluorogenic substrate (Toronto Rerearch Chemicals Inc, Ontario, Canada), as described previously (van Diggelen et al., 1990). Liver, adipose tissue and femur GALNS activity levels were normalized against the total amount of protein, quantified using Bradford protein assay (Bio-Rad, Hercules, CA, US).

For GAG quantification, tissue samples were weighted and then digested with proteinase K and extracts were clarified by centrifugation and filtration. GAG levels were determined by liquid chromatography-mass spectrometry (LC-MS/MS) in tissue extracts and serum. The levels of GAG were normalized to wet tissue weight or to total volume of digested samples.

7. Histological Analysis

Tissues were fixed for 12-24 h in formalin, embedded in paraffin and sectioned.

For GAG storage detection in corneal epithelium, paraffin sections were subjected to Mowry's colloidal staining, which reveals GAGs in blue color. For GAG storage detection in lacrimal gland and tibial epiphyseal growth plate, resin sections were subjected to toluidine blue staining which reveals GAG storage in white color.

The NIS Elements Advanced Research 2.20 software was used to quantify % of GAG+ area in 15-20 images of each eye (original magnification, ×40) per animal, using the same signal threshold settings for all animals. Then, the percentage of positive area was calculated, i.e., the area, in pixels, with a positive signal over the total tissue area in the region of interest from the image.

8. Transmission Electron Microscopy Analysis

Mice were sacrificed by an overdose of isoflurane (Isoflo, Labs. Esteve, Barcelona, ES) and perfused via inferior vena cava with 1 ml of 2.5% glutaraldehyde and 2% paraformaldehyde. A small portion (approximately 1 $mm^3$) of the dentate gyrus and amygdala were sectioned and incubated for 2 hours at 4° C. in the same fixative. After washing in cold cacodylate buffer, the specimens were post-fixed in 1% osmium tetroxide, stained in aqueous uranyl acetate, and then dehydrated through a graded ethanol series and embedded in epoxy resin. Ultrathin sections (600-800 A) from the resin blocks were stained using lead citrate and examined in a transmission electron microscope (H-7000; Hitachi, Tokyo, JP).

9. Statistical Analysis

All results are expressed as mean±SEM. Statistical comparisons were made using one-way ANOVA. Multiple comparisons between control and treatment groups were made using Dunnett's post-test, and between all groups using Tukey's post-test. Statistical significance was considered if P<0.05.

EXAMPLES

Example 1: Construction of pAAV-CAG-hGALNS

The CDS for human galactosamine (N-acetyl)-6-sulfatase (NCBI Reference Sequence: NM_000512.4) was used as starting material and was chemically synthetized for this purpose (GeneArt; Life Technologies). The CDS SEQ ID NO: 1 was received cloned inside the plasmid pMK-RQ (KanR) flanked by Mlul and EcoRI restriction sites at 5' and 3', respectively.

Figure 1:
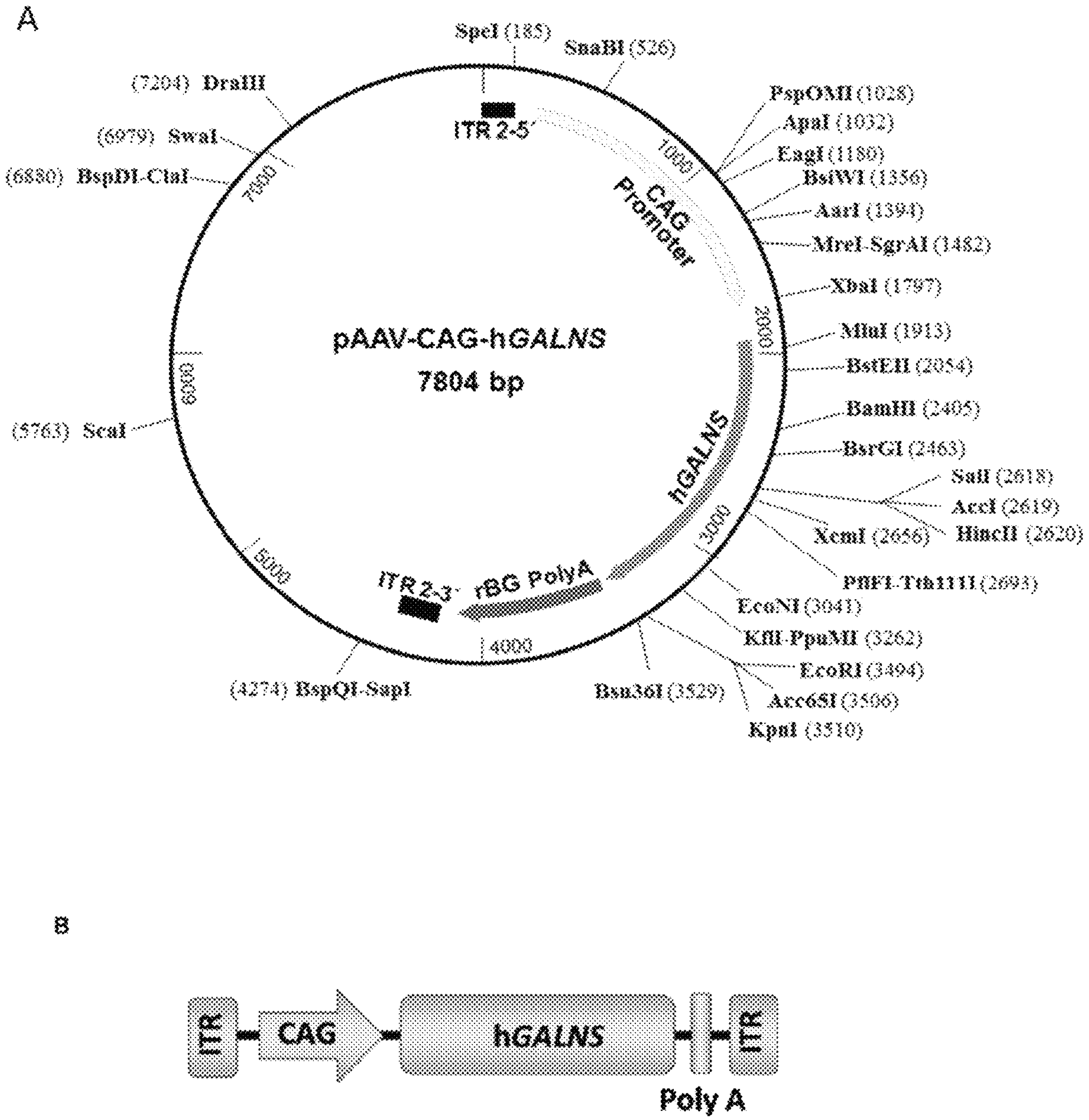
FIG. 1. Generation of pAAV-CAG-hGALNS and AAV9-CAG-hGALNS. (A) Schematic representation of the plasmid pAAV-CAG-hGALNS and its components. (B) Schematic representation of the genome of an Adeno-associated vector containing the hGALNS coding sequence.

The Mlul/EcoRI human galactosamine (N-acetyl)-6-sulfatase CDS fragment was excised from the pMK-RQ plasmid and subsequently cloned between the Mlul and EcoRI restrictions sites of the AAV backbone plasmid pAAV-CAG. The resulting plasmid was named pAAV-CAG-hGALNS (accession number DSM 32791). See FIG. 1A and SEQ ID NO: 2.

The AAV backbone plasmid pAAV-CAG used herein had been previously generated and contained the ITRs from the AAV2 genome, the CAG promoter, and the polyA signal from rabbit β-globin, as well as a multicloning site for cloning of CDSs of interest. The CAG promoter is a hybrid promoter composed of the CMV early/intermediate enhancer and the chicken β-actin promoter. This promoter is able to drive a potent expression ubiquitously.

Example 2: Construction of pAAV-CAG-ohGALNS-v1

Expression cassettes including an optimized version of galactosamine (N-acetyl)-6-sulfatase cDNA sequence (ohGALNS) were designed and obtained. The sequence optimization was performed to maximize the efficiency of galactosamine (N-acetyl)-6-sulfatase protein production in human beings through elimination of cryptic splice sites and RNA destabilizing sequence elements for increased RNA stability, addition of RNA stabilizing sequence elements, codon optimization and G/C content adaptation, avoidance of stable RNA secondary structures amongst others changes. The CDS for human galactosamine (N-acetyl)-6-sulfatase (NCBI Reference Sequence: NM_000512.4) was used as starting point for sequence optimization.

The optimized CDS SEQ ID NO: 3 (GeneArt: Life Technologies) was received cloned inside the plasmid pMK-RQ (KanR) flanked by Mlul and EcoRI restriction sites at 5' and 3', respectively.

Figure 2:
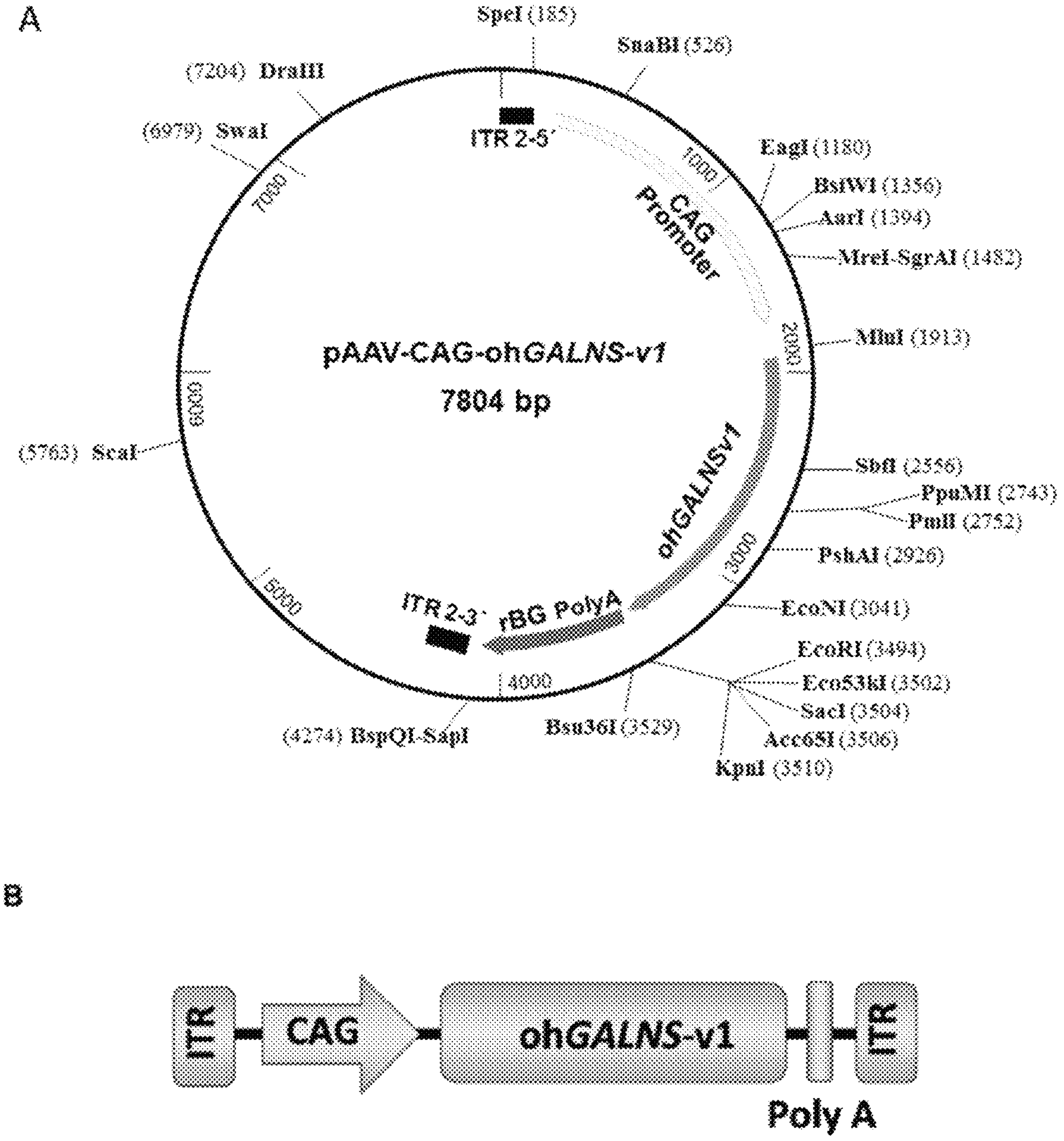
FIG. 2. Generation of pAAV-CAG-ohGALNS-v1 and AAV9-CAG-ohGALNS-v1. (A) Schematic representation of the plasmid pAAV-CAG-ohGALNS-v1 and its components. (B) Schematic representation of the genome of an Adeno-associated vector containing the ohGALNS-v1 coding sequence.

The Mlul/EcoRI optimized human galactosamine (N-acetyl)-6-sulfatase CDS fragment was excised from the pMK-RQ plasmid and subsequently cloned between the Mlul and EcoRI restrictions sites of the AAV backbone plasmid pAAV-CAG. The resulting plasmid was named pAAV-CAG-ohGALNS-v1 (accession number DSM 32792). See FIG. 2A and SEQ ID NO: 4.

Example 3: Construction of pAAV-CAG-ohGALNS-v2

The CDS for human galactosamine (N-acetyl)-6-sulfatase (NCBI Reference Sequence: NM_000512.4) was subjected to sequence optimization (GenSript, Inc). The optimized CDS SEQ ID NO: 5 was received cloned inside the plasmid pUC57 (AmpR) flanked by Mlul and EcoRI restriction sites at 5' and 3', respectively.

Figure 3:
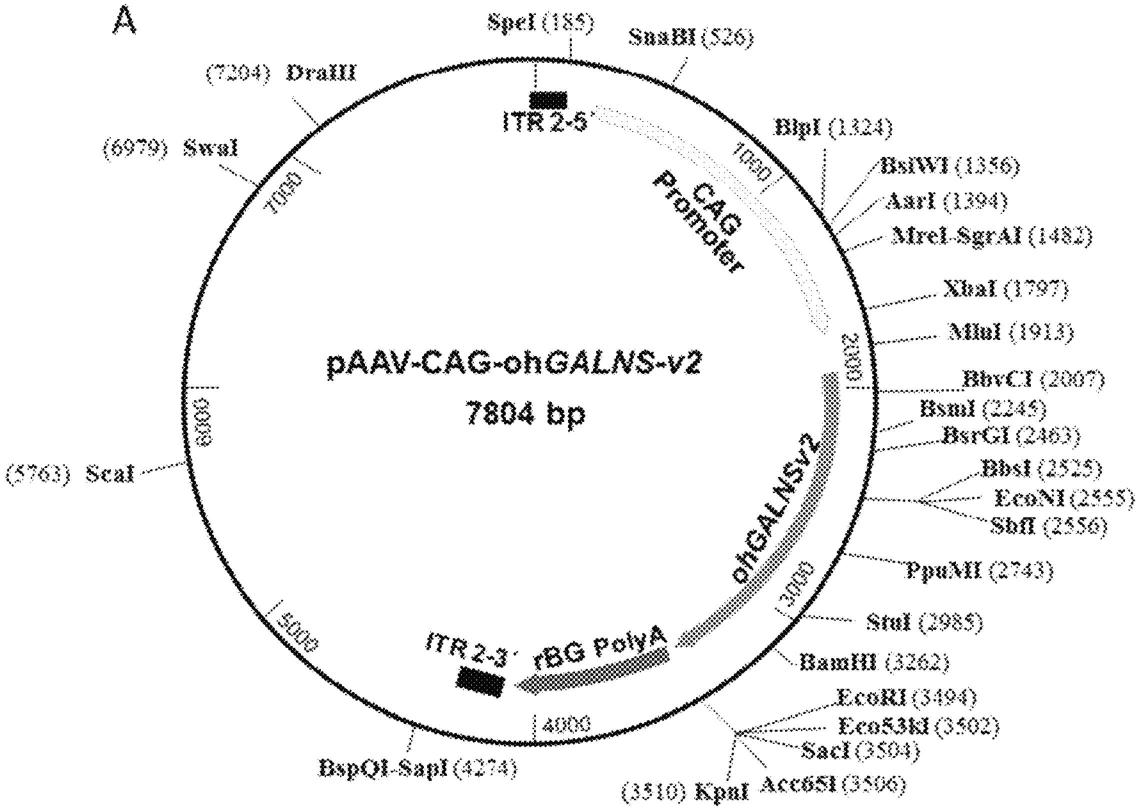
FIG. 3. Generation of pAAV-CAG-ohGALNS-v2 and AAV9-CAG-ohGALNS-v2. (A) Schematic representation of the plasmid pAAV-CAG-ohGALNS-v2 and its components. (B) Schematic representation of the genome of an Adeno-associated vector containing the ohGALNS-v2 coding sequence.
Figure 3:
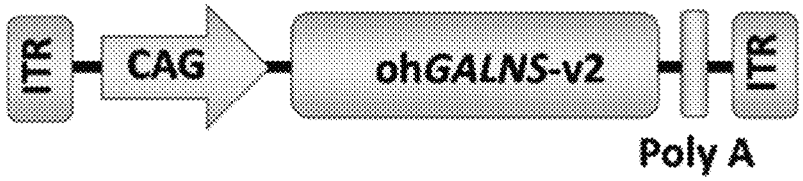

The Mlul/EcoRI optimized human galactosamine (N-acetyl)-6-sulfatase CDS fragment was excised from the pUC57 plasmid and subsequently cloned between the Mlul and EcoRI restrictions sites of the AAV backbone plasmid pAAV-CAG. The resulting plasmid was named pAAV-CAG-ohGALNS-v2 (accession number DSM 32793). See FIG. 3A and SEQ ID NO: 6.

Example 4: Construction of pAAV-CAG-ohGALNS-v3

The CDS for human galactosamine (N-acetyl)-6-sulfatase (NCBI Reference Sequence: NM_000512.4) was subjected to sequence optimization (DNA 2.0 Inc). The optimized CDS SEQ ID NO: 7 was received cloned inside the plasmid pj201 (KanR) flanked by Mlul and EcoRI restriction sites at 5' and 3', respectively.

Figure 4:
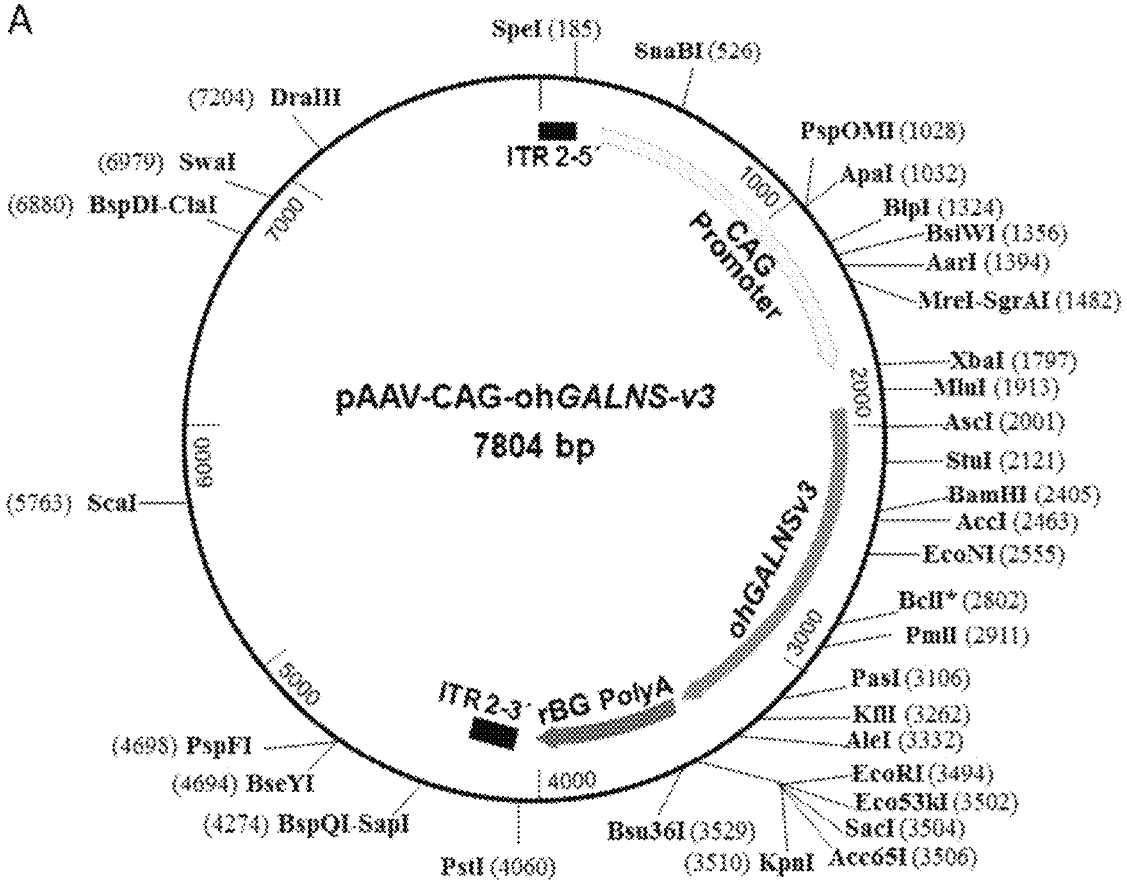
FIG. 4. Generation of pAAV-CAG-ohGALNS-v3 and AAV9-CAG-ohGALNS-v3. (A) Schematic representation of the plasmid pAAV-CAG-ohGALNS-v3 and its components. (B) Schematic representation of the genome of an Adeno-associated vector containing the ohGALNS-v3 coding sequence.
Figure 4:

The Mlul/EcoRI optimized human galactosamine (N-acetyl)-6-sulfatase CDS fragment was excised from the pj201 plasmid and subsequently cloned between the Mlul and EcoRI restrictions sites of the AAV backbone plasmid pAAV-CAG. The resulting plasmid was named pAAV-CAG-ohGALNS-v3 (accession number DSM 32794). See FIG. 4A and SEQ ID NO: 8.

Example 5: Construction of pAAV-CAG-omGALNS

The CDS for murine galactosamine (N-acetyl)-6-sulfatase (NCBI Reference Sequence: NM_016722.4) was subjected to sequence optimization (GeneArt; Life Technologies). The optimized CDS SEQ ID NO: 9, was received cloned inside the plasmid pMA-RQ-Bb (AmpR) flanked by Mlul and EcoRI restriction sites at 5' and 3', respectively.

Figure 5:
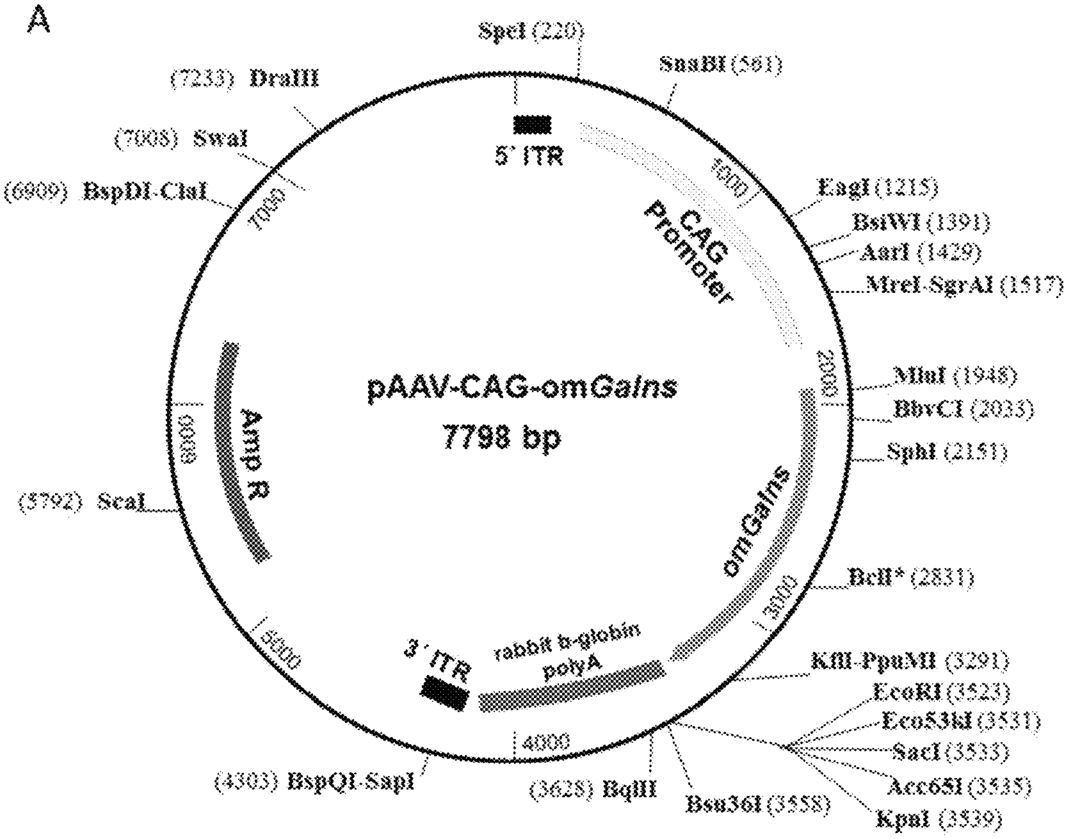
FIG. 5. Generation of pAAV-CAG-omGalns, AAV9-CAG-omGalns and AAV8-CAG-omGalns. (A) Schematic representation of the plasmid pAAV-CAG-omGalns and its components. (B) Schematic representation of the genome of an Adeno-associated vector containing the omGalns coding sequence.
Figure 5:
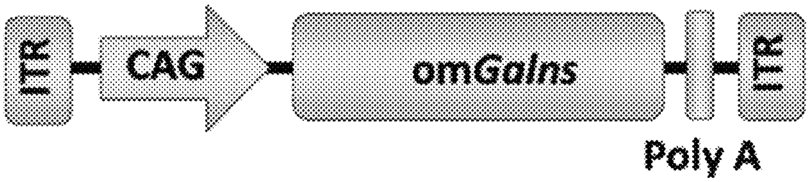

The Mlul/EcoRI optimized murine galactosamine (N-acetyl)-6-sulfatase CDS fragment was excised from the pMA-RQ-Bb plasmid and subsequently cloned between the Mlul and EcoRI restrictions sites of the AAV backbone plasmid pAAV-CAG. The resulting plasmid was named pAAV-CAG-omGALNS. See FIG. 5A and SEQ ID NO: 10.

Example 6: Construction of pAAV-hAAT-omGALNS

The CDS for murine galactosamine (N-acetyl)-6-sulfatase (NCBI Reference Sequence: NM_016722.4) was subjected to sequence optimization (GeneArt; Life Technologies) SEQ ID NO: 9.

The hAAT promoter (SEQ ID NO: 19) was received cloned inside the plasmid pGG2-hAAT (AmpR) flanked by BglII and Mlul restriction sites at 5' and 3', respectively.

Figure 6:
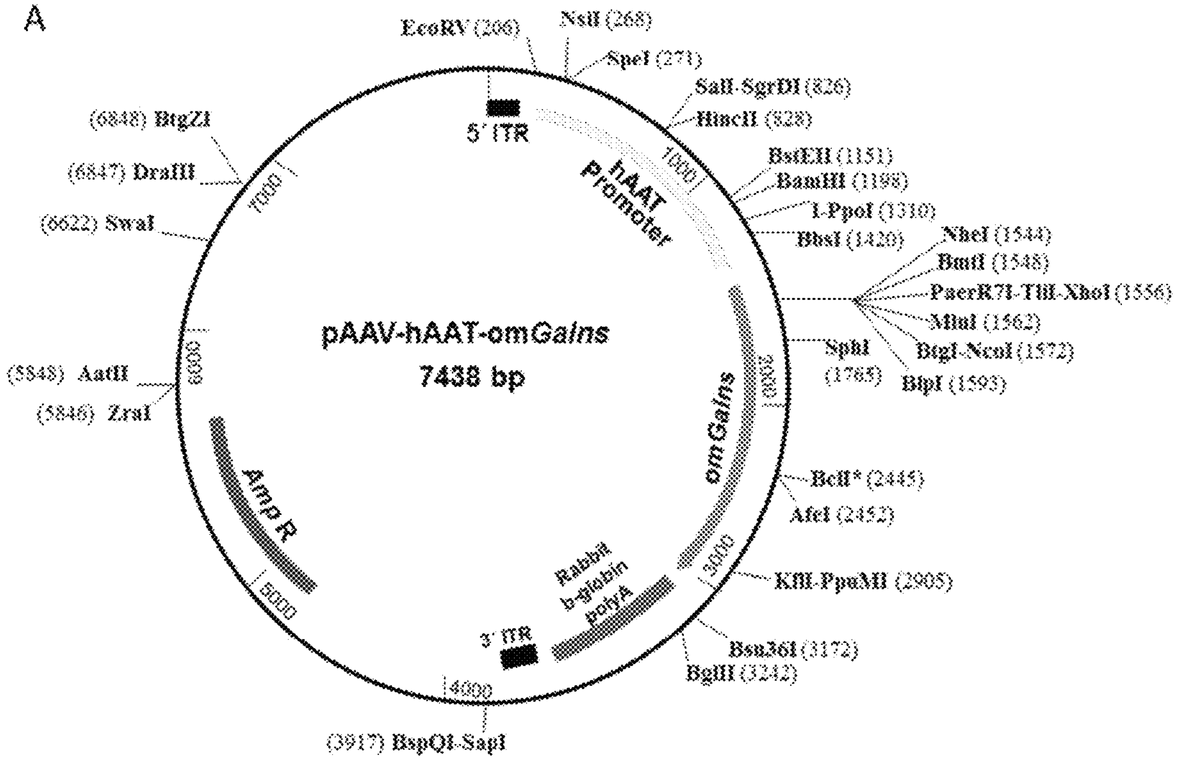
FIG. 6. Generation of pAAV-hAAT-omGalns and AAV8-hAAT-omGalns. (A) Schematic representation of the plasmid pAAV-hAAT-omGalns and its components.
Figure 6:

The CAG promoter (SEQ ID NO: 18) was excised from the pAAV-CAG-omGALNS plasmid and subsequently replaced by hAAT promoter. The resulting plasmid was named pAAV-hAAT-omGALNS. See FIG. 6A and SEQ ID NO: 11.

The hAAT promoter is a hybrid promoter composed of the human α1-antitrypsin promoter and three copies of the hepatocyte control region (HCR) enhancer from the apolipoprotein E. This promoter is able to drive a potent expression liver-specific.

Example 7: Production of AAV9-CAG-hGALNS

Vectors AAV9-CAG-hGALNS (SEQ ID NO: 12) were generated by helper virus-free transfection of HEK293 cells using three plasmids with modifications (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-CAG-hGALNS; SEQ ID NO: 2); 2) a plasmid carrying the AAV2 rep and the AAV9 cap genes (pREP2CAP9); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 1B.

Example 8: Production of AAV9-CAG-ohGALNS-v1

Vectors AAV9-CAG-ohGALNS-v1 (SEQ ID NO: 13) were generated by helper virus-free transfection of HEK293 cells using three plasmids with modifications. (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-CAG-ohGALNS-v1; SEQ ID NO: 4); 2) a plasmid carrying the AAV2 rep and the AAV9 cap genes (pREP2CAP9); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic®: F68, filtered, titered by qPCR and stored at −80° C. until use. See FIG. 2B.

Example 9: Production of AAV9-CAG-ohGALNS-v2

Vectors AAV9-CAG-ohGALNS-v2 (SEQ ID NO: 14) were generated by helper virus-free transfection of HEK293 cells using three plasmids with modifications. (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-CAG-ohGALNS-v2; SEQ ID NO: 6): 2) a plasmid carrying the AAV2 rep and the AAV9 cap genes (pREP2CAP9); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 3B.

Example 10: Production of AAV9-CAG-ohGALNS-v3

Vectors AAV9-CAG-ohGALNS-v3 (SEQ ID NO: 15) were generated by helper virus-free transfection of HEK293 cells using three plasmids with modifications. (Matsushita et al., 1998: Wright et al., 2005). Cells were cultured to 70% confluence in roller bottles (RB) (Corning. Corning, NY, US) in DMEM supplemented with 10% FBS and then co-transfected with: 1) a plasmid carrying the expression cassette flanked by AAV2 ITRs (pAAV-CAG-ohGALNS-v3; SEQ ID NO: 7); 2) a plasmid carrying the AAV2 rep and the AAV9 cap genes (pREP2CAP9): and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 4B.

Example 11: Production of AAV9-CAG-omGALNS

Vectors AAV9-CAG-omGALNS (SEQ ID NO: 16) were generated by helper virus-free transfection of HEK293 cells using three plasmids with modifications. See (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-CAG-omGALNS; SEQ ID NO: 10); 2) a plasmid carrying the AAV2 rep and the AAV9 cap genes (pREP2CAP9); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 5B and SEQ ID NO: 16.

Example 12: Production of AAV8-CAG-omGALNS

Vectors AAV8-CAG-omGALNS (SEQ ID NO: 16) were generated by helper virus-free transfection of HEK293 cells using three plasmids with modifications. See (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-CAG-omGALNS; SEQ ID NO: 10); 2) a plasmid carrying the AAV2 rep and the AAV8 cap genes (pREP2CAP8); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 5B and SEQ ID NO: 16.

Example 13: Production of AAVB-hAAT-omGALNS

Vectors AAV8-hAAT-omGALNS (SEQ ID NO: 17) were generated by helper virus-free transfection of HEK293 cells using three plasmids with modifications. See (Matsushita et al., 1998; Wright et al., 2005). Cells were cultured to 70% confluence in roller bottles (RB) (Corning, Corning, NY, US) in DMEM supplemented with 10% FBS and then co-transfected with: 1) a plasmid carrying the expression cassette flanked by AAV2 ITRs (pAAV-hAAT-omGALNS: SEQ ID NO: 11); 2) a plasmid carrying the AAV2 rep and the AAV8 cap genes (pREP2CAP8); and 3) a plasmid carrying the adenovirus helper functions. Vectors were purified by two consecutives caesium chloride gradients using an optimized protocol as previously described (Ayuso et al., 2010). Vectors were dialyzed against PBS+0.001% Pluronic® F68, filtered, titered by qPCR and stored at −80° C. until use. See FIG. 6B and SEQ ID NO: 17.

Example 14: Intravenous Injection of AAV9-CAG-hGALNS, AAV9-CAG-Oh GALNS-v1, AAV9-CAG-ohGALNS-v2 or AAV9-CAG-ohGALNS-v3 to MPSIVA Mice A total dose of $5\times10^{10}$ vector genomes of AAV9-CAG-hGALNS, AAV9-CAG-onGALNS-v1, AAV9-CAG-ohGALNS-v2 or AAV9-CAG-ohGALNS-v3 containing different versions of the human galactosamine (N-acetyl)-6-sulfatase expressing cassette were delivered intravenously to 2-month-old MPSIVA-affected mice via tail vein injection.

GALNS activity analysis was performed 2 weeks after vector delivery. Transduction with all four galactosamine (N-acetyl)-6-sulfatase-containing vectors resulted in a substantial increase in galactosamine (N-acetyl)-6-sulfatase activity over the levels measured in MPSIVA animals. Galactosamine (N-acetyl)-6-sulfatase activity levels ranged from 1500% to 2600% of WT levels in liver and 55% to 99% of WT in serum. See FIGS. 7A and 7B. In the liver, the levels of activity reached with the expression cassette containing both version 2 and version 3 of human galactosamine (N-acetyl)-6-sulfatase were higher than those mediated by the vector containing the wild-type sequence. See FIG. 7A. In serum, both version 2 and version 3 of human galactosamine (N-acetyl)-6-sulfatase led to higher increases in enzymatic activity than wild-type and version 1. See FIG. 7B.

Example 15: Intravenous Delivery of AAV9-CAG-omGALNS, AAV8-CAG-omGALNS or AAV8-hAAT-omGALNS to MPSIVA Mice A total dose of $1\times10^{12}$ vector genomes of AAV9-CAG-omGALNS, $1\times10^{12}$ vector genomes of AAV8-CAG-omGALNS or $1\times10^{11}$ vector genomes of AAV8-hAAT-omGALNS vectors were injected through tail vein of 3-4-week-old MPSIVA animals in a total volume of 200 μl. Four and six months after vector administration, the animals were sacrificed and samples collected for further analysis.

Six months after AAV treatment, enzymatic activity of GALNS in the liver, femur, adipose tissue and serum of MPSIVA treated animals was normalized, reaching similar or even higher values that those observed in healthy animals. See FIGS. 8, 9 and 10. The restoration of GALNS activity led to a complete normalization of the substrate accumulation characteristic of the disease in liver and serum, as indicated by similar concentrations of keratan sulfate in wild-type controls and treated Galns$^{-/-}$ mice. See FIG. 11.

The intravenous administrations of the different vectors to the bloodstream transduces mainly the liver among other tissues and organs (Ruzo et al., 2012). Accordingly, GALNS activity in the liver of MPSIVA male mice treated with the different vectors was approximately 25-fold higher than that observed in healthy animals. See FIG. 8A, 9A and 10A.

When overexpressed in the liver, soluble lysosomal proteins are efficiently secreted to the bloodstream, turning this organ into a source of circulating enzyme (Ruzo et al., 2012). In the serum of treated MPSIVA mice, GALNS activity reached a peak around month 3-post injection and afterwards was long-term stabilized with values ranging from 20 to 50 fold higher than in wild-type littermates. See FIGS. 8D, 9D and 10D. When the somatic efficacy of the therapy was evaluated through quantification of the GAG content in serum and liver, a full normalization of circulating and hepatic KS levels was observed See FIG. 11.

Four months after AAV delivery, tibial epiphyseal growth plates from MPSIVA treated mice showed a distinctly reduction of intracellular GAG accumulation indicated by the presence of multiple intracellular GAG depots. See FIG. 12.

AAV-treated animals also showed a complete normalization of the GAG accumulation in lacrimal glands indicated by the absence of intracellular GAG depots See FIG. 13B. Likewise, the quantification of the signal intensity of GAG positive area in corneal epithelium sections stained with Mowry's colloidal staining, revealed a reduction in % of GAG deposition over the surface of the corneal epithelium in Galns$^{-/-}$ mice treated with AAV9-CAG-omGALNS or AAV8-hAAT-omGALNS over values documented in GALNS-deficient mice. See FIG. 13A.

The ultrastructural analysis by transmission electron microscopy of the dentate gyrus and amygdala of 7-month-old male mice revealed the presence of large vacuoles containing electrolucent substance in the cytoplasm of cells from non-treated GALNS-deficient mice. These cells were identified as perivascular macrophages in the dentate gyrus or perineuronal glial cells and endothelial cells in the amygdala. These vesicles, which appeared to be lysosomes filled with storage material, were completely absent in samples from healthy wild-type or Galns$^{-/-}$ animals treated with AAV9-CAG-omGALNS, confirming the restoration of the normal size of the lysosomal compartment following gene transfer. See FIG. 14.

The invention claimed is:

1. An isolated polynucleotide having a nucleotide sequence selected from the group consisting of SEQ ID NO: 3, SEQ ID NO: 5, and SEQ ID NO: 7, wherein the polynucleotide encodes a functional human galactosamine (N-acetyl)-6-sulfatase.

2. An expression vector comprising a polynucleotide of claim 1.

3. The expression vector of claim 2, wherein the expression vector comprises a promoter element operatively linked to the polynucleotide, wherein the promoter is selected from a CAG promoter, a hAAT promoter and a CMV promoter.

4. The expression vector of claim 3, wherein the promoter is a CAG promoter.

5. The expression vector of claim 2, wherein the vector is a recombinant Adeno-associated virus (AAV) vector.

6. The expression vector of claim 5, wherein the recombinant AAV vector is selected from AAV2, AAV5, AAV7, AAV8, AAV9, AAV10 and AAVrh10.

7. The expression vector of claim 2, wherein the vector is selected from the group consisting of the plasmid pAAV-CAG-ohGALNS-version1 as set forth in SEQ ID NO: 4, the plasmid pAAV-CAG-ohGALNS-version2 as set forth in SEQ ID NO: 6, and the plasmid pAAV-CAG-ohGALNS-version3 as set forth in SEQ ID NO: 8.

8. A pharmaceutical composition comprising a therapeutically effective amount of the expression vector of claim 2.

9. The pharmaceutical composition of claim 8, wherein the pharmaceutical composition is in a form for intravenous administration.

10. A method of treating mucopolysaccharidosis type IVA or Morquio A syndrome in a subject in need thereof, comprising administering the expression vector of claim 5, alone or in combination with one or more pharmaceutically acceptable excipients.

11. The method of claim 10, wherein the expression vector is administered intravenously.

12. A method for obtaining a recombinant expression vector comprising the steps of:

(i) providing a cell comprising a polynucleotide of claim 1, AAV cap proteins, AAV rep proteins and, viral proteins upon which AAV is dependent for replication, (ii) maintaining the cell under conditions adequate for assembly of the AAV; and (iii) purifying the adeno-associated viral vector produced by the cell.

* * * * *